(12) United States Patent
Machii et al.

(10) Patent No.: US 10,557,706 B2
(45) Date of Patent: Feb. 11, 2020

(54) MEASUREMENT PROCESSING DEVICE, X-RAY INSPECTION APPARATUS, METHOD FOR MANUFACTURING STRUCTURE, MEASUREMENT PROCESSING METHOD, X-RAY INSPECTION METHOD, MEASUREMENT PROCESSING PROGRAM, AND X-RAY INSPECTION PROGRAM

(71) Applicant: NIKON CORPORATION, Tokyo (JP)

(72) Inventors: Nobukatsu Machii, Yokohama (JP); Fuminori Hayano, Tokyo (JP); Akitoshi Kawai, Yokohama (JP)

(73) Assignee: Nikon Corporation, Tokyo (JP)

( * ) Notice: Subject to any disclaimer, the term of this patent is extended or adjusted under 35 U.S.C. 154(b) by 342 days.

(21) Appl. No.: 15/446,455

(22) Filed: Mar. 1, 2017

(65) Prior Publication Data

US 2017/0176181 A1   Jun. 22, 2017

Related U.S. Application Data

(63) Continuation of application No. PCT/JP2014/073097, filed on Sep. 2, 2014.

(51) Int. Cl.
*G01B 15/02* (2006.01)
*G01B 15/04* (2006.01)
(Continued)

(52) U.S. Cl.
CPC ............. *G01B 15/04* (2013.01); *G01N 23/04* (2013.01); *G01N 23/046* (2013.01); *G01N 2223/304* (2013.01); *G01N 2223/401* (2013.01)

(58) Field of Classification Search
CPC .. G01B 15/04; G01N 23/04; G01N 2223/304; G01N 2223/401; G01N 23/046
See application file for complete search history.

(56) References Cited

U.S. PATENT DOCUMENTS 3,514,606 A   5/1970   Rabey
4,614,430 A   9/1986   Hara et al.
(Continued)

FOREIGN PATENT DOCUMENTS

CN   103940835 A   7/2014
EP   2 801 815 A1   11/2014
(Continued)

OTHER PUBLICATIONS

European Search Report issued by the European Patent Office in corresponding European Application No. 14901042.3, dated Jan. 31, 2018.
(Continued)

*Primary Examiner* — Kiho Kim
(74) *Attorney, Agent, or Firm* — Finnegan, Henderson, Farabow, Garrett & Dunner, L.L.P.

(57) ABSTRACT

A measurement processing device used for an x-ray inspection apparatus that detects an x-ray passing through a predetermined region of a specimen placed on a placement unit to perform an inspection on the shape of the predetermined region of the specimen includes: a setting unit that sets a three-dimensional region to be detected on the specimen; and a sliced-region selection unit that sets a plurality of sliced regions on the region to be detected, calculates, for each of the plurality of sliced regions, an amount of displacement of the predetermined region that is required to detect the region to be detected when the plurality of sliced regions is regarded as the predetermined region, and selects a sliced region for the inspection from among the plurality of sliced regions on the basis of each of the calculated amounts of displacement.

34 Claims, 37 Drawing Sheets

(51) Int. Cl.
G01N 23/046 (2018.01)
G01N 23/04 (2018.01)

(56) References Cited

U.S. PATENT DOCUMENTS

| | | | |
|---|---|---|---|
| 4,803,639 A | | 2/1989 | Steele et al. |
| 5,291,535 A | | 3/1994 | Baker et al. |
| 5,796,802 A | * | 8/1998 | Gordon ................. G01T 1/2985 378/8 |
| 6,047,041 A | | 4/2000 | Ellinger |
| 6,341,153 B1 | | 1/2002 | Rivera et al. |
| 7,151,817 B1 | * | 12/2006 | Abraham ............. G01N 23/046 378/57 |
| 9,256,930 B2 | | 2/2016 | Suzuki |
| 9,476,844 B2 | | 10/2016 | Tagawa |
| 9,597,041 B2 | | 3/2017 | Claus et al. |
| 9,739,729 B2 | * | 8/2017 | Feser ................. G01N 23/2206 |
| 2002/0080913 A1 | | 6/2002 | Roder |
| 2005/0008214 A1 | | 1/2005 | Willis |
| 2006/0093082 A1 | | 5/2006 | Numata et al. |
| 2007/0081624 A1 | | 4/2007 | Nabatame |
| 2007/0116177 A1 | * | 5/2007 | Chen ....................... G01N 23/04 378/57 |
| 2007/0237293 A1 | * | 10/2007 | Singh ................... G01N 23/046 378/57 |
| 2007/0286339 A1 | * | 12/2007 | Rothschild ........... G01N 23/046 378/57 |
| 2008/0056443 A1 | * | 3/2008 | Hu ......................... G01N 23/10 378/54 |
| 2009/0168949 A1 | * | 7/2009 | Bendahan ............ G01N 23/046 378/5 |
| 2011/0085636 A1 | | 4/2011 | Dennerlein |
| 2011/0211671 A1 | * | 9/2011 | Chen ..................... G01N 23/046 378/53 |
| 2013/0108017 A1 | | 5/2013 | Golubovic et al. |
| 2013/0308747 A1 | * | 11/2013 | Abraham ................. A61B 6/03 378/16 |
| 2014/0003573 A1 | | 1/2014 | Sadaoka et al. |
| 2015/0078518 A1 | | 3/2015 | Tziazas et al. |
| 2015/0221077 A1 | | 8/2015 | Kawabata et al. |
| 2016/0334345 A1 | * | 11/2016 | Freeman ............. G01N 23/046 |
| 2017/0241919 A1 | | 8/2017 | Machii et al. |

FOREIGN PATENT DOCUMENTS

| | | |
|---|---|---|
| JP | 2000-033082 A | 2/2000 |
| JP | 2005-249426 A | 9/2005 |
| JP | 2006-105794 | 4/2006 |
| JP | 2006-125960 A | 5/2006 |
| JP | 2007-114150 A | 5/2007 |
| JP | 2007-285973 A | 11/2007 |
| JP | 4131400 | 8/2008 |
| JP | 2009-125795 | 6/2009 |
| JP | 2013-096992 A | 5/2013 |
| JP | 2013-140090 A | 7/2013 |
| JP | 2013-217773 | 10/2013 |
| JP | 2013-217797 A | 10/2013 |
| JP | 2013-257155 A | 12/2013 |
| WO | WO 2007/122770 | 11/2007 |
| WO | WO 2016/035147 A1 | 3/2016 |

OTHER PUBLICATIONS

International Search Report issued in International Application No. PCT/JP2014/073097, dated Dec. 16, 2014 (2 pages).

Miyake, Tomofumi, et al., "Introduction of X-Ray CT Scanner and Application Examples", Mazda Technical Review, No. 22, pp. 167-172 (2004).
Office Action dated Feb. 7, 2019 issued in U.S. Appl. No. 15/507,999.
Office Action issued by Japanese Patent Office dated Aug. 28, 2018 in counterpart Application No. 2016-546226, and English translation thereof.
International Search Report issued in corresponding International Application No. PCT/JP2014/073096, dated Dec. 16, 2014.
Partial Supplementary European Search Report issued by the European Patent Office in corresponding European Application No. 14901232.0, dated Jan. 31, 2018.
Extended European Search Report issued by the European Patent Office in corresponding European Application No. 14901232.0, dated Mar. 13, 2018.
Pending U.S. Appl. No. 16/118,296, "Measurement Processing Device, X-Ray Inspection Apparatus, Method for Manufacturing Structure, Measurement Processing Method, X-Ray Inspection Method, Measurement Processing Program, and X-Ray Inspection Program", filed Aug. 30, 2018.
Pending U.S. Appl. No. 16/149,423, "Measurement Processing Device, Measurement Processing Method, Measurement Processing Program, and Method for Manufacturing Structure", filed Oct. 2, 2018.
Pending U.S. Appl. No. 15/507,999, "Measurement Processing Device, Measurement Processing Method, Measurement Processing Program, and Method for Manufacturing Structure", filed Mar. 1, 2017.
Siwek, Elizabeth M., "Application of the X-ray measurement model to image processing of X-ray radiographs", Iowa State University Digital Repository, Retrospective Theses and Dissertations 255 (1994).
European Search Report issued by the European Patent Office in corresponding European Application No. 14901042.3, dated Apr. 30, 2018.
Schmitt, R., et al., "Improving the Production using X-Ray Computed Tomography-Potentials and Challenges" National Conference on CT Scanning—Application of CT Scanning Industry, Danish Technological Institute Taastrup, May 31, 2011.
De Chifre, L., et al., "Industrial applications of computed tomography", CIRP Annals—Manufacturing Technology, 63:655-677 (2014).
Office Action issued by the State Intellectual Property Office of the People's Republic of China (SIPO) dated Apr. 1, 2019 in counterpart Application No. 201480083003.4, and English translation thereof.
Office Action issued by the Japanese Patent Office dated Jun. 25, 2019 in counterpart Japanese Patent Application No. 2018-153882, and English Translation thereof.
Office Action issued by the Japanese Patent Office dated Aug. 6, 2019 in counterpart Japanese Patent Application No. 2018-176484, and English Translation thereof.
Office Action issued by the U.S. Patent Office dated Sep. 9, 2019 in counterpart U.S. Appl. No. 16/118,296.
Office Action issued by the U.S. Patent Office dated Sep. 13, 2019 in counterpart U.S. Appl. No. 15/507,999.
Communication from the European Patent Office enclosing the European Official Action for Application No. 14 901 042.3, dated Oct. 23, 2019, 5 pages.
Communication pursuant to Article 94(3) EPC (EPO Office Action) dated Oct. 25, 2019, issued by the European Patent Office in counterpart European Patent Application No. 14 901 232.0.
Notification of Reasons for Refusal of the counterpart Japanese Patent Application No. 2013-546226 dated Dec. 3, 2019.
Notification of Reasons for Refusal of the counterpart Japanese Patent Application No. 2016-546226 dated Dec. 3, 2019.

* cited by examiner

| EVALUATION REGION | INDIVIDUAL | | ALIGNMENT | |
|---|---|---|---|---|
| | DIRECTION OF THICKNESS AND THICKNESS | DIRECTION OF LENGTH AND LENGTH | ALIGNMENT PLANE AND NUMBER OF REGIONS IN ALIGNMENT PLANE | ARRANGEMENT DIRECTION OF ALIGNMENT PLANE AND NUMBER ARRANGED |
| CRANKSHAFT JOURNAL (EVALUATION REGION 601) | 2 mm IN V | 70 mm IN U | 1 IN WU | 4 IN V |
| CAST PULL PIN | 70 mm IN U | 2 mm IN V | 4 IN VW | NONE (1) |
| (EVALUATION REGION 602) | 10 mm DIAMETER IN U (V) | 100 mm IN W | 2 IN WU | 4 IN V |
| | 10 mm DIAMETER IN U (V) | 100 mm IN W | 4 IN VW | 2 IN U |
| LINER (EVALUATION REGION 603) | 2 mm IN V | 100 mm IN W | 2 IN WU | 3 IN V |
| | 20 mm IN U | 100 mm IN W | 3 IN VW | 2 IN U |
| COOLING CHANNEL (EVALUATION REGION 604) | 10 mm DIAMETER IN U (V) | 300 mm IN V | 2 IN UV | NONE (1) |
| | 10 mm DIAMETER IN U (V) | 300 mm IN V | 1 IN VW | 2 IN U |

FIG. 15

NON-DEFECT LEVEL

| | | SIMPLE VOLUME RATIO NON-DEFECT LEVEL | | | | |
|---|---|---|---|---|---|---|
| | | 0 | 1 | 2 | 3 | 4 |
| THICKNESS NON-DEFECT LEVEL | 0 | 0 | 0 | 1 | 1 | 2 |
| | 1 | 0 | 1 | 1 | 2 | 3 |
| | 2 | 1 | 1 | 2 | 3 | 4 |

FIG. 29

MEASUREMENT PROCESSING DEVICE, X-RAY INSPECTION APPARATUS, METHOD FOR MANUFACTURING STRUCTURE, MEASUREMENT PROCESSING METHOD, X-RAY INSPECTION METHOD, MEASUREMENT PROCESSING PROGRAM, AND X-RAY INSPECTION PROGRAM

INCORPORATION BY REFERENCE

This application is a continuation of international application No. PCT/JP2014/073097 filed Sep. 2, 2014.

The disclosures of the following priority applications are herein incorporated by reference: International application No. PCT/JP2014/073097 filed Sep. 2, 2014.

BACKGROUND ART

1. Technical Field

The present invention relates to a measurement processing device, an x-ray inspection apparatus, a method for manufacturing structure, a measurement processing method, an x-ray inspection method, a measurement processing program, and an x-ray inspection program.

2. Description of Related Art

Conventionally, as disclosed in Japanese Patent No. 4131400B, a technique is known for performing a comparison with three-dimensional design data for a specimen and an evaluation of the thickness and internal defects of a specimen using an x-ray measurement apparatus for the purpose of non-destructive internal inspection.

SUMMARY

Shortening the time necessary for inspection of a specimen is desired. Also, shortening the time to make a performance evaluation of the production process of the specimen from the results of the inspection of the specimen is desired.

According to a first aspect of the present invention, a measurement processing device used for an x-ray inspection apparatus that detects an x-ray passing through a predetermined region of a specimen placed on a placement unit to perform an inspection on the shape of the predetermined region of the specimen comprises: a setting unit that sets a three-dimensional region to be detected on the specimen; and a sliced-region selection unit that sets a plurality of sliced regions on the region to be detected, calculates, for each of the plurality of sliced regions, an amount of displacement of the predetermined region that is required to detect the region to be detected when the plurality of sliced regions are regarded as the predetermined region, and selects a sliced region for the inspection from the plurality of sliced regions on the basis of each of the calculated amounts of displacement.

According to a second aspect of the present invention, an x-ray inspection apparatus that detects an x-ray passing through a predetermined region of a specimen to inspect the shape of the predetermined region of the specimen comprised: a setting unit that sets a plurality of three-dimensional regions to be detected on the specimen, a grouping unit that divides the plurality of regions to be detected into a first group detected at a first magnification and a second group detected at a second magnification, and a control unit that performs x-ray detection at a first magnification for each of the regions to be detected belonging to the first group, and thereafter performs x-ray detection at a second magnification for each of the regions to be detected belonging to the second group.

According to a third aspect of the present invention, a manufacturing method for a structure comprises: creating design information regarding the shape of a structure; creating the structure on the basis of the design information; acquiring shape information by measuring the shape of the created structure by using the measurement processing device according to the first aspect or the x-ray inspection apparatus according to the second aspect; and comparing the acquired shape information and the design information.

According to a fourth aspect of the present invention, a measurement processing method comprises: setting a three-dimensional region to be detected on the specimen to perform an inspection on the shape of a predetermined region of the specimen by detecting an x-ray passing through the predetermined region of the specimen placed on a placement unit; and setting a plurality of sliced regions for the region to be detected, calculating, for each of the plurality of sliced region, an amount of displacement of the predetermined region that is required to detect the region to be detected when the plurality of sliced regions are regarded as the predetermined region, and selecting a sliced region for the inspection from among the plurality of sliced regions on the basis of each of the calculated amounts of displacement.

According to a fifth aspect of the present invention, an x-ray inspection method that detects an x-ray passing through a predetermined region of a specimen to inspect the shape of the predetermined region of the specimen comprises: setting each of a plurality of three-dimensional regions to be detected on the specimen; dividing the plurality of regions to be detected into a first group detected at a first magnification and a second group detected at a second magnification; and performing x-ray detection at the first magnification for each of the regions to be detected belonging to the first group, and thereafter performing x-ray detection at the second magnification for each of the regions to be detected belonging to the second group.

According to a sixth aspect of the present invention, a measurement processing program for causing a computer to execute comprises: setting processing for setting a three-dimensional region to be detected on a specimen to perform an inspection on the shape of a predetermined region of the specimen by detecting an x-ray passing through the predetermined region of the specimen placed on a placement unit; and selection processing for setting a plurality of sliced regions for the region to be detected, calculating, for each of the plurality of sliced regions, an amount of displacement of the predetermined region that is required to detect the region to be detect when the plurality of sliced regions are regarded as the predetermined region, and selecting a sliced region for the inspection from among the plurality of sliced regions on the basis of each of the calculated amounts of displacement.

According to a seventh aspect of the present invention, an x-ray inspection program for causing a computer to execute comprises: inspection processing for inspecting the shape of a predetermined region of a specimen by detecting an x-ray passing through the predetermined region of the specimen; setting processing for setting each of a plurality of three-dimensional regions to be detected on the specimen; division processing for dividing the plurality of regions to be detected into a first group detected at a first magnification and a second group detected at a second magnification; and measurement processing for performing x-ray detection at the first magnification for each of the regions to be detected belonging to the first group, and thereafter performing x-ray detection at the second magnification for each of the regions to be detected belonging to the second group.

According to the present invention, the time necessary for inspection of a specimen can be shortened.

BRIEF DESCRIPTION OF THE DRAWINGS

FIG. 15 is a figure illustrating an example of classification according to cluster analysis.

FIG. 29 is a figure illustrating an example of non-defect levels selected from volume ratio non-defect levels and thickness non-defect levels.

DESCRIPTION OF EMBODIMENTS

An x-ray inspection apparatus and an inspection processing device for an x-ray inspection apparatus will be described according to one embodiment of the present invention with reference to the drawings. The x-ray inspection apparatus non-destructively acquires internal information (for example, the internal configuration) of a specimen by emitting an x-ray at the specimen and detecting the transmitted x-ray passing through the specimen. The present embodiment will be described giving an example wherein the x-ray inspection apparatus is used as an internal inspection device to acquire internal information about a cast item such as an engine block and perform non-defect management or the like therefor.

Note that the x-ray inspection apparatus 100 is not limited to a cast item such as an engine block, and may also acquire shape information for the internal structure of a joint part for an item formed of plastic when respective members have been joined using adhesive or welding, and may perform inspection therefor.

Furthermore the present embodiment is for describing the meaning of the invention in detail for understanding, and does not limit the present invention as long as it is not specifically designated.

Figure 1:
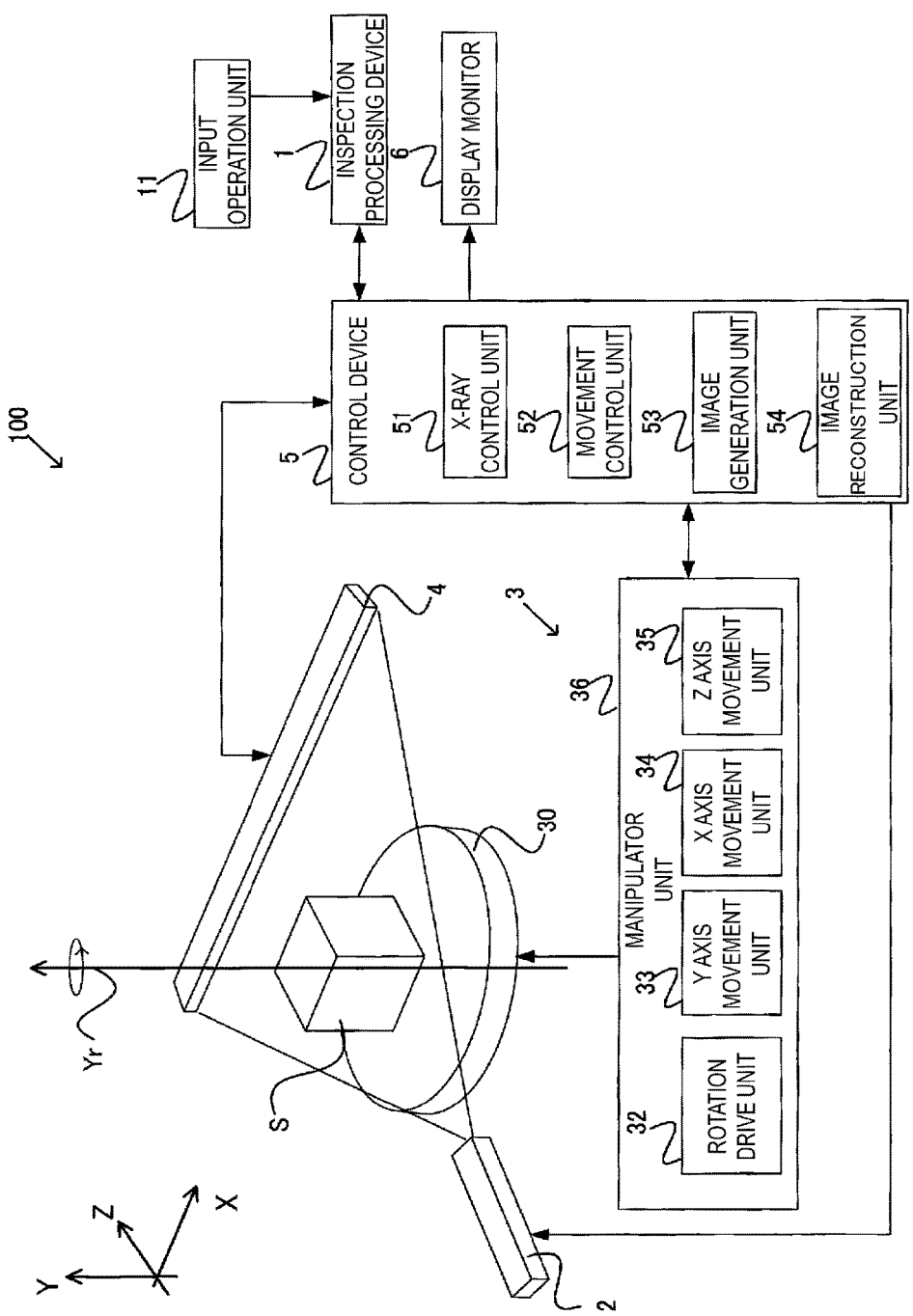
FIG. 1 is a figure illustrating the configuration of an x-ray inspection apparatus and its inspection processing device according to an embodiment of the present invention.

FIG. 1 is a drawing schematically illustrating an example of a configuration of an x-ray inspection apparatus 100 according to the present embodiment. Note that for convenience of description, a coordinate system composed of an X axis, a Y axis, and a Z axis is set as is illustrated in the drawing.

The x-ray inspection apparatus 100 is provided with an inspection processing device 1, an x-ray source 2, a placement unit 3, a detector 4, a control device 5, a display monitor 6, and an input operation unit 11. Note that the inspection processing device 1 being configured separately from the x-ray inspection apparatus 100 is included in one aspect of the present invention. The x-ray source 2, placement unit 3, and detector 4 are stored inside a chassis (not illustrated in the drawing) disposed so as to be substantially horizontal in the XZ plane on top of the floor of a factory or the like. The chassis includes lead as a material so that x-rays do not leak to the outside.

The x-ray source 2 emits x-rays in a fan shape (a so-called "fan beam") in the Z axis+direction along an optical axis Zr parallel to the Z axis with the emission point Q illustrated in FIG. 1 as the vertex, in accordance with control by the control device 5. The emission point Q corresponds to the focal point of the x-ray source 2. That is, the optical axis Zr connects the emission point Q, which is the focal point of the x-ray source 2, with the center of the image capturing region of the detector 4 described hereinafter. Note that for the x-ray source 2, instead of one emitting x-rays in a fan shape, one emitting x-rays in a cone shape (a so-called "cone beam") is also included in one aspect of the present invention. The x-ray source 2 can emit, for example, at least one of: an approximately 50 eV ultrasoft x-ray, an approximately 0.2-2 keV soft x-ray, an approximately 2-20 keV x-ray, and an approximately 20-100 keV hard x-ray, and additionally, an x-ray having an energy of 100 keV or greater.

The placement unit 3 is provided with a placement stage 30 on which a specimen S is placed, and a manipulator unit 36 made from a rotation drive unit 32, a Y axis movement unit 33, an X axis movement unit 34, and a Z axis movement unit 35, provided further in the Z axis+side than the x-ray generation unit 2. The placement stage 30 is provided so as to be rotatable by the rotation drive unit 32, and when the rotation axis Yr moves in the X axis, Y axis, or Z axis directions due to the rotation drive unit 32, it also moves therewith.

The rotation drive unit 32 is, for example, configured by an electric motor or the like, is parallel to the Y axis and rotates the placement stage 30 with an axis passing through the center of the placement unit 30 as a rotational axis Yr via the rotational force generated by an electric motor controlled and driven by a control device 5, described hereinafter. The Y axis movement unit 33, the X axis movement unit 34, and the Z axis movement unit 35 are controlled by the control device 5, and each move the placement stage 30 in the X axis direction, the Y axis direction, and the Z axis direction respectively so that the specimen S is positioned in the emission range of the x-rays emitted by the x-ray generation unit 2. In addition, the Z axis movement unit 35 is controlled by the control unit 5, and moves the placement stage 30 in the Z axis direction so that the distance from the x-ray source 2 to the specimen S is a distance wherein the specimen S in the captured image is at the desired magnification ratio.

The detector 4 is provided further in the Z direction+side than the x-ray source 2 and the placement stage 30. That is, the placement stage 30 is provided between the x-ray source 2 and the detector 4 in the Z direction. The detector 4 is a so-called line sensor, which has an incident surface 41 extending along the X direction on a plane parallel to the XY plane; x-rays including the transmission x-rays passing through the specimen S placed on the placement stage 30 emitted from the x-ray source 2 are incident upon the incident surface 41. The detector 4 is configured by a scintillator unit including a publicly known scintillating substance, a photomultiplier tube, a light receiving unit, and the like; it converts the energy of x-rays incident on the incident surface 41 of the scintillator unit to light energy such as visible light or ultraviolet light, amplifies it with the photomultiplier tube, converts the amplified light energy to electric energy with the aforementioned light receiving unit, and outputs it as an electric signal to the control device 5.

Note that the detector 4 may convert the energy of incident x-rays to electric energy and output it as an electric signal without converting it to light energy. The detector 4 has a composition wherein the scintillator unit, the photomultiplier tube, and the light receiving unit are each divided into a plurality of pixels. Thus, it can acquire an intensity distribution for the x-rays which have been emitted from the x-ray source 2 and have passed through the specimen S. Note that as the detector 4, a composition may be had wherein the scintillator unit is directly formed on the light receiving unit (photoelectric conversion unit) without providing a photomultiplier tube.

Note that the detector 4 is not limited to a line sensor, and may be a two-dimensional planar detector. That is, in the present embodiment, the line sensor for the detector 4 has an incident surface 41 extending in the X direction on a plane parallel to the XY plane, but only one incident surface 41 is disposed in the Y direction. Furthermore, in the XY plane, a plurality of incident surfaces 41 are disposed in the X direction. Also, each of the plurality of incident surfaces 41 can independently detect the intensity of an x-ray. In the present embodiment, a plurality of the incident surfaces 41 may be aligned in the Y direction. For example in the XY plane in FIG. 1, it may be a two-dimensional planar detector wherein a plurality of incident surfaces 41 are disposed in the X direction and the Y direction. Also, in a case where a two-dimensional planar detector is used, it may be used as a line sensor, wherein only the incident surfaces 41 in the X direction at a predetermined location in the Y direction are used from among the plurality of incident surfaces 41 aligned in the Y direction. In this case, an intensity distribution of the x-rays on the incident surfaces 41 at the predetermined position in the Y direction may be acquired, and the shape information for the specimen S may be analyzed from the intensity distribution of the x-rays acquired at the predetermined position in the Y direction. Also, in this case, when acquiring an intensity distribution of the x-rays on the incident surfaces 41 in the X direction at a plurality of positions in the Y direction, an intensity distribution for x-rays on the incident surfaces 41 in the X direction at positions that are mutually separated in the Y direction may be acquired.

The x-ray source 2, the placement stage 3, and the detector 4 are supported by a frame (not illustrated in the drawings). The frame is constructed having sufficient rigidity. Thus, it is possible to stably support the x-ray source 2, the placement stage 3, and the detector 4 while acquiring a projected image of the specimen S. Further, the frame is supported by an anti-vibration mechanism (not illustrated in the drawings) to prevent vibration generated on the outside from being transmitted as is to the frame.

The input operation unit 11 is configured by a keyboard, various buttons, a mouse, and the like and is operated when the position of the region to be inspected is input at the time of the inspection of the specimen S, as will be described hereinafter, or updating the region to be inspected and the like by an operator. When the input operation unit 11 is operated by an operator, an operation signal corresponding to the operation is output to the inspection processing device 1.

The control device 5 has a microprocessor and its peripheral circuits and the like, and controls various units of the x-ray inspection apparatus 100 by reading in and executing a control program stored beforehand on a storage medium not illustrated in the drawings (for example, flash memory or the like). The control device 5 is provided with an x-ray control unit 51, a movement control unit 52, an image generation unit 53, and an image reconstruction unit 54. The x-ray control unit 51 controls the behavior of the x-ray source 2, and the movement control unit 52 controls the movement behavior of the manipulator 36. The image generation unit 53 generates x-ray projected image data for the specimen S based on an electric signal output from the detector 4, and the image reconstruction unit 54 performs per se known image reconstruction processing, and generates a reconstructed image based on the projected image data for the specimen S from each different projection direction while controlling the manipulator unit 36. This reconstructed image is an image illustrating the structure of the interior of the portion of the specimen S positioned in between the x-ray source 2 and the detector 4, and is output as voxel data. The voxel data is an absorption coefficient distribution of the specimen S. Further, in the present embodiment, three-dimensional shape information, which is the internal structure of the specimen S, is generated by a surface model construction unit provided inside the image reconstruction unit 54 based on the reconstructed image acquired at different positions in the Y direction. In this case, back projection, filtered back projection, iterative reconstruction, and the like may exist as image reconstruction processing.

As illustrated in the block diagram in FIG. 2, the inspection processing device 1 has a microprocessor and its peripheral circuits and the like, and performs various processing when inspecting a portion of the specimen S, described hereinafter, by reading in and executing a control program stored beforehand on a storage medium not illustrated in the drawings (for example, flash memory or the like). The inspection processing device 1 is provided with a configuration information acquisition unit 55, an inspection control unit 56, an inspection analysis unit 57, and a data accumulation unit 58. The configuration information acquisition unit 55 acquires design information such as a three-dimensional CAD regarding the specimen S, and information regarding internal defects and the like of the specimen S obtained from a simulation. The inspection control unit 56 performs processing for shortening the inspection time (hereinafter inspection time shortening processing) when inspecting a region to be inspected of one part of the specimen S, as is described hereinafter. The inspection analysis unit 57 analyzes shape information for the specimen S generated based on transmission images, which are the inspection result for the specimen S, and performs change, addition, deletion, and the like of regions of the specimen to be inspected in a following inspection. The data accumulation unit 58 is a non-volatile storage medium for storing various data generated by processing by the inspection control unit 56 and the inspection analysis unit 57. Note that the details of the inspection control unit 56 and the inspection analysis unit 57 will be described hereinafter.

The x-ray inspection apparatus 100 moves the placement stage 30 in each of the XYZ directions to position the specimen S in an inspection position when performing an inspection of the internal structure of the specimen S. Then, the x-ray inspection apparatus 100 emits a slit beam having a predetermined width in the Y direction from the x-ray source 2 at the specimen S being rotated with the rotation driving of the placement stage 30. The detector 4 receives the transmission x-rays, including x-rays passing through the specimen S, and obtains shape information for the cross-section of the specimen S corresponding to the width (for example, approximately 1 mm) in the Y direction of the slit beam. The x-ray inspection apparatus 100 repeatedly performs the emission of the slit beam toward the specimen S during rotation driving and the movement of the placement stage 30 in the Y direction, that is, the movement of the specimen S in the Y direction. When the slit beam is performed in a range extending to the entire region along the length in the Y direction of the specimen S placed on the placement stage 30, it can generate shape information for the entire specimen S (hereinafter called a full scan). In the case that the emission of the slit beam is performed in a range of a portion of the length in the Y direction of the specimen S placed on the placement stage 30, it can generate shape information for a portion of the specimen S based on the transmission image (hereinafter called a partial scan).

Note that in the present specification, in the following description, the region in which the slit beam overlaps with the specimen S is called the sliced plane. In the present embodiment, when the specimen S is disposed in the region prescribed by the emission point Q and the incident surface 41 of the detector 4, an x-ray passing through the specimen S can be detected. In this case, the detectable region for the x-ray passing through the specimen S is called the sliced plane. The sliced plane is a region having a predetermined width. Note that in the present embodiment, the region in which the region prescribed by the incident surface 41 of the detector 4 and the emission point Q and the specimen S are superimposed is the sliced plane. Of course, the sliced plane may, for example, be a region connecting the emission point Q and the center of the detector 4. In the present specification, the width of the sliced plane corresponds to a region for generating voxel data, and corresponds to one where the voxel is one level, that is, the aligned number of voxels in the Y direction is one. Furthermore, the sliced region corresponds to a region for generating voxel data, and corresponds to one where the voxel is one level or plural level, that is, the aligned number of voxels in the Y direction is one or a plurality. Hereinafter, description of the embodiment in the present specification will be carried out assuming that the region from which a voxel is generated from a transmission image acquired with one rotation driving of the placement stage 30 is a sliced plane with a one-level voxel. However, the assumption that the width of the sliced place is a one-level voxel has the object of facilitating understanding of the invention, and the width of the sliced plane in the present invention is not limited to that above. The position of the slit plane relative to the specimen S on the placement stage 30 moves in the Y direction with the movement of the placement stage 30 in the Y direction. In the description below, this movement of the sliced plane relative to the specimen S is called displacement, and the amount of movement at this time is called the amount of displacement. Note that in the present embodiment, when the placement stage 30 is moved in the Y direction after detecting a predetermined region in a predetermined location, the predetermined region detected prior to the movement and the predetermined region detected subsequent to the movement are not superimposed. Of course, they may be partially superimposed.

The x-ray inspection apparatus 100 in the present embodiment performs an inspection by performing a full scan or a partial scan of several of the specimen S having similar shapes, for example, as in a cast item. A full scan means a measurement operation to generate a reconstruction image at a predetermined interval in the Y direction to acquire the interior structure of the entire specimen S. It is performed at an opportunity where a relatively large amount of time can be allocated to inspection time, when volume production manufacturing isn't being performed, such as after maintenance on the cast for the specimen S. A partial scan means a measurement operation to generate a reconstruction image for only one portion, including an evaluation region described hereinafter from within the specimen S. Besides the timing for performing a full scan described above, several portions of the specimen S with a high likelihood of an internal defect occurring (hereinafter called evaluation regions) are selected as regions to be inspected and are performed when inspected.

An inspection time T for the specimen S according to the x-ray inspection apparatus 100 is determined with the following Form. (1).

$$\text{Inspection time } T = Tr \times Nr \times Ns \qquad \text{Form. (1)}$$

Nr is the frequency at which the transmission image data is acquired in the detector 4 while the specimen S performs one rotation centered on the rotation axis Yr. The greater the value of Nr, in other words the acquisition frequency of the transmission image data, becomes, the thinner in angle slice taking data becomes. Tr is the time required to acquire one rotation of data, and corresponds to the time required to generate transmission image data from transmission x-rays received by the detector 4. Ns is the sum of the number of sliced planes, that is, it is a value dividing the sum of the amount of movement of the specimen S in the Y direction (amount of displacement) by the thickness of one sliced plane. From the aforementioned Form. (1), the inspection time T for the specimen S can be understood to increase compared to the number of sliced planes.

If the width of the sliced plane is approximately 1 mm and the time required to inspect one sliced plane is 2 minutes, in a case where a full scan is performed on a specimen S whose size in the Y direction is 400 mm, the inspection time would be 400 mm/1 mm×2 min=13 hours, so it can be understood that an extremely long time is required.

Note that the resolving power for three-dimensional data for the specimen S constructed from inspection data is related to the angular resolving power and the distance from the center of rotation. Thus, even if the slices of the rotation angle at the time of the inspection are made thinner than necessary, only the measurement time will increase; in particular, the resolving power in the region close to the center of rotation will not improve. In order to increase the resolving power, it is effective to move the specimen S closer to the x-ray source 2 and raise the enlargement ratio.

In the present embodiment, the inspection control unit 56 performs inspection time shortening processing for shortening the inspection time T when performing a partial scan on the specimen S by performing a selection of an appropriate sliced plane. Below a detailed description will be performed regarding inspection time shortening processing.

Figure 2:
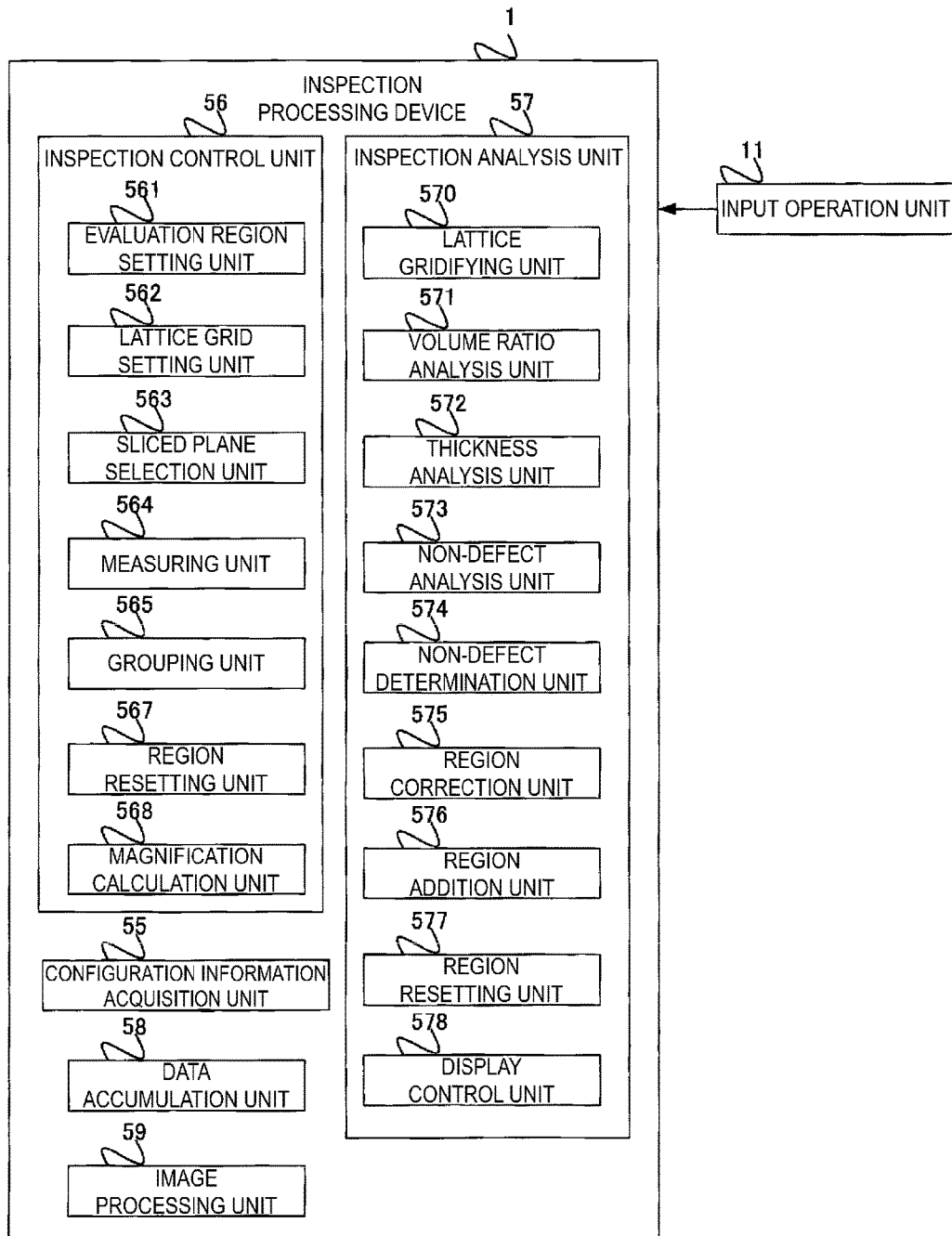
FIG. 2 is a block diagram illustrating a primary element configuration of an x-ray inspection apparatus and an inspection processing device according to an embodiment.

As illustrated in the block diagram in FIG. 2, the inspection control unit 56 is provided with an evaluation region setting unit 561, a lattice grid setting unit 562, a sliced plane selection unit 563, an inspection unit 564, a grouping unit 565, and a magnification calculation unit 568.

The evaluation region setting unit 561 performs evaluation region setting processing for setting an evaluation region on which to have an inspection performed at the time of a partial scan on the specimen S using information and the like based on design information acquired by the composition information acquisition unit 55 or simulations. The lattice grid setting unit 562 divides a region including the set evaluation region into three-dimensional lattice units and turns it into a lattice grid, which reduces the processing load of selecting a sliced plane, described hereinafter. The sliced plane selection unit 563 performs sliced plane and reference plane selection processing for selecting an appropriate emission direction of the x-rays from the viewpoint of inspection time shortening, that is, the sliced plane, when performing a partial scan.

The inspection unit 564 performs x-ray CT inspection processing for controlling the x-ray source 2, the detector 4, the manipulator unit 36, and the like via the control device 5 so that the specimen S is inspected in the sliced plane selected by the sliced plane selection unit 563. Here, shape information can be generated for a specimen S including the internal structure for each sliced plane. The grouping unit 565 classifies (groups) the plurality of evaluation regions into a plurality of groups based on their shape characteristics so that selection can be performed for an appropriate sliced plane by the sliced plane selection unit 563. A region resetting unit 575 resets the position of the evaluation region set by the region setting unit 561 within a settable range based on a settable range included in the evaluation region described hereinafter, when performing selection of an appropriate sliced plane by the sliced plane selection unit 563. The magnification calculation unit 568 performs position matching when inspecting a set evaluation region, and calculation of the magnification when acquiring a transmission image to generate a reconstruction image of the evaluation region.

Below, a detailed description will be given of each processing performed by the inspection control unit 56, the evaluation region setting unit 561, the lattice grid setting unit 562, the sliced plane selection unit 563, the inspection unit 564, the grouping unit 565, and the magnification calculation unit 568. First, a definition of the terms on which the description of each processing is presupposed will be performed.

1. Definition of Terms 1.1. Evaluation Region

The evaluation region is a site in which the occurrence of internal defects or the like in the specimen S are expected caused by the structure of the specimen S or the manufacturing method, and is a region for evaluating its condition from an investigation result using x-rays as is described hereinafter. In the present embodiment, the evaluation region is spatially specified as an initial value by an operator, and change or deletion of the spatial position is performed according to the operator's determination. In a case where the specimen S is the cylinder block for an engine, the following examples exist.

Regions Needing Management of Product Functionality

The cast iron liner encasting the bore portion of a cylinder, the cast iron bearing cap encasting the crankshaft journal portion of the cylinder block or rudder frame, the vicinity of the cooling channel, the fastening portion of bolt fasteners and the like, and the locations of the oil pan and the mission case are given.

The degree of adhesion between the iron material and the aluminum material in locations where an encasting technique is used when manufacturing the specimen S is an important item to be managed; when adhesion of the liner portion is bad, the bearing force of the bore at the time of precision work drops, which has an influence on the circularity of the bore; also, when the engine is running, deformation due to heat generation is uneven, which increases the sliding resistance of the piston ring. In either case, this brings about a drop in output and a worsening of fuel efficiency. For the bearing gap, the degree of adhesion is, if course, important, but in a case where there are many blowholes, since this portion has a large load placed thereon, this becomes a problem for the mechanism's strength. An increase in load from the crankshaft due to engine running can ultimately be connected to crank occurrence.

In a case where cavities occur in succession in the thin portion in the vicinity of the cooling channel, the risk of a cooling water leak increases. Thus, it is desirable that an evaluation region be set in a direction where the particularly thin portion in the vicinity of the cooling channel extends. All engine blocks are tested with a leak tester after rough machining of the cooling channel, but it is desirable that the risk of a leak is known at an early stage before rough machining. Since the fastening portion of bolt fasteners and the like is a portion on which a load is placed, there is a need to check the presence of a crack and the possibility of blowholes extending to become the crack. Normally, a method of impregnation inspection is used; x-ray inspection is effective for an inspection of this portion. An inspection of limited sites alone is effective for the oil pan, mission case, and the like.

Regions Derived from the Necessity of Dimension Management

In casting, the shape of the formed item changes depending on the combining accuracy of the mold. Thus, an evaluation region is set based on the mold structure and the management structure of the core. In particular, there is a need for inspection immediately after maintenance of the mold.

Because the engine block is made increasingly thinner to decrease weight, there is a need to manage whether the thickness is within tolerances. Because thickness tolerances are prescribed for each portion, a stipulated site is set as an evaluation region, and the smallest thickness within that evaluation region is measured and output.

Regions Decided by Empirical Values

The region of the engine block corresponding to the vicinity of the gate and vicinity of cast pull pin on the mold is set as an evaluation region. There is a possibility that the cast pull pin on the mold, which has an extreme temperature cycle, will become worn, will have the pin bent, or will not completely cool; furthermore, the possibility of wearing in the vicinity of the gate through which hot liquid solution flows at high speed is higher than in other places. For this reason, the region of the engine block corresponding to these portions on the mold should have an inspection performed thereon at a high frequency. Setting of the evaluation region and evaluation timing can be standardized based on knowledge obtained through experience.

Region Decided by Simulation

There is also a need to make portions wherein the possibility that a defect may occur is predicted in a simulation into evaluation regions. There is also a need to make misrun at the confluence of hot liquid solution and drawn cavities in portions where the thickness greatly changes into evaluation regions.

Regions in the Vicinity of Machining Surfaces

The vicinity of machining surfaces assumed to be post-machined after casting are set as evaluation regions. This is because there is a problem in that cavities that do not appear on the surface in the casted state will appear after post-machining.

Figure 3:
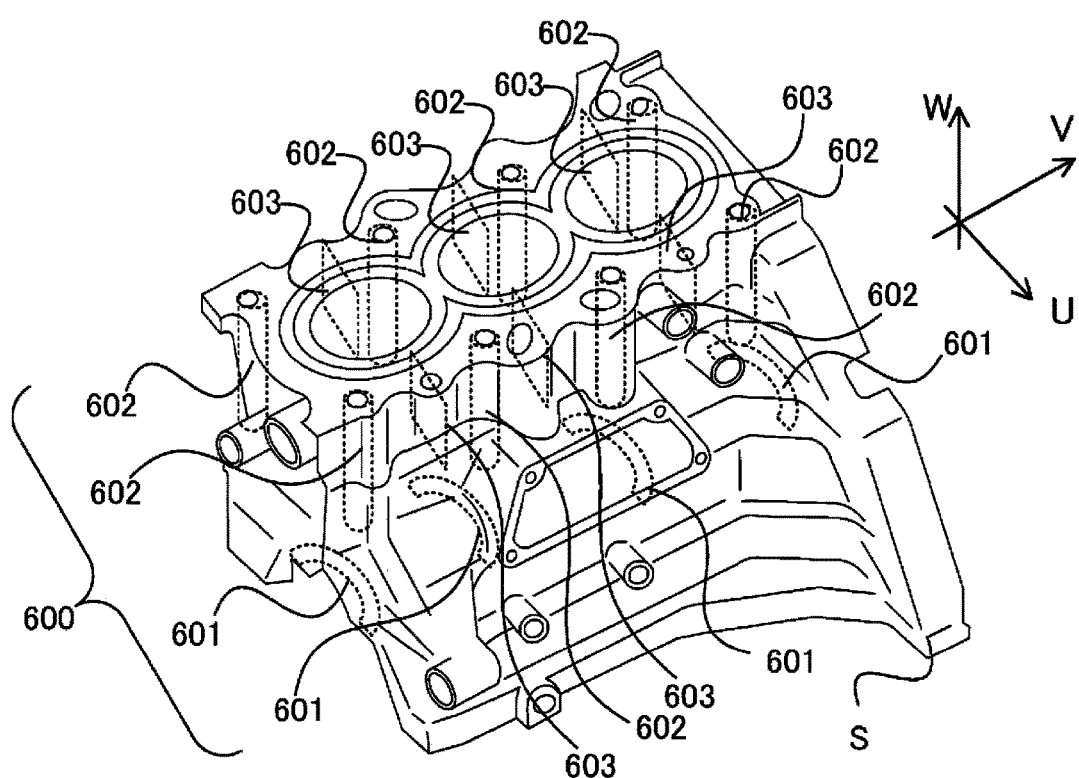
FIG. 3 is a figure illustrating an example of an evaluation region set when inspecting a cylinder block of an engine as a specimen.

In FIG. 3, one example of an evaluation region 600 in a case where a cylinder block of an engine is the specimen S is illustrated. In the evaluation region 600, various three-dimensional shapes are included. Inside the engine block, an evaluation region 601 in the vicinity of the crankshaft journal portion is a semi-circular arc shape with thickness. An evaluation region 602 in the vicinity of the cast pull pin is a cylinder shape enclosing the cast pull pin. Also, an evaluation region 603 managing the dimensions of thickness and the like is a shape including the dimension measurement target. An evaluation region of a portion in which drawn cavities are predicted to occur in a simulation is an indefinite shape described hereinafter.

Note that in the description below, an orthogonal coordinate system made from a U axis, a V axis, and a W axis is set with regards to the specimen S.

1.2. Lattice Grid

Figure 4:
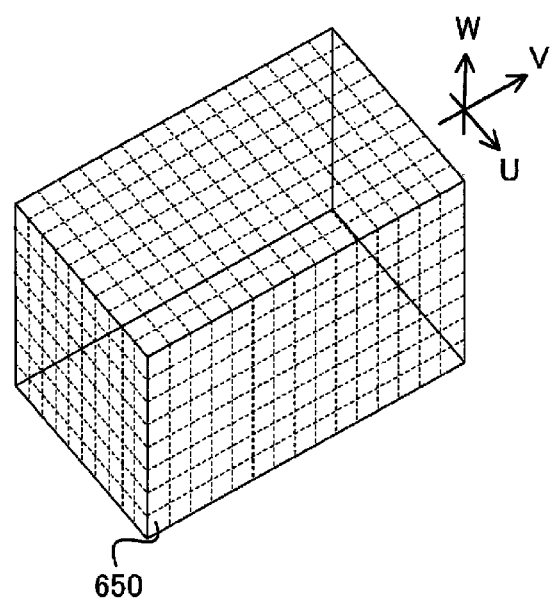
FIG. 4 is a figure illustrating a lattice grid.

One example of a lattice grid 650 is illustrated in FIG. 4. The lattice grid 650 is provided in a three-dimensional shape along each of the UVW directions. A plurality of lattice grids 650 are applied to the evaluation regions 600 interspersed within the specimen S having various shapes, and are provided to calculate the relationship of the orientation of the specimen S when placed on the placement stage 30 and the radiation direction of the x-rays to shorten the inspection time for the evaluation regions. Each of the plurality of evaluation regions 600 are shown by the plurality of lattice grid 650 being applied to the evaluation regions 600 having various three-dimensional shapes and sizes, as will be described hereinafter. That is, by dividing the evaluation regions 600 using a plurality of lattice grids 650, it can simplify from which UVW direction a partial scan is performed on a region including the evaluation regions 600 of the specimen S based on the lattice grids 650, that is, processing when performing sliced plane selection, described hereinafter. Furthermore, the volume of cavities per unit volume of lattice grid (the volume ratio) can be calculated by handling the investigation results in lattice grid 650 units when analyzing the investigation results for the specimen S in the investigation analysis unit 57.

The lattice grids 650 are set so as to include a plurality of so-called voxel data. Voxel data is the smallest unit configuring three-dimensional data generated by the image reconstruction unit 54. The size of the lattice grids 650 (grid size) is set to, for example, 1/10 or 1/5 the size of the evaluation region 6, smaller than the size of the evaluation regions 600. That is, size relationship of the size of the voxel size, the grid size, and the evaluation region is set so as to be the voxel size < the grid size < the size of the evaluation region.

Note that for the aforementioned voxel data, the closer the specimen S is to the x-ray source 2, the finer the three-dimensional pitch of the voxel data of the specimen S can be obtained. The coarseness of the voxel data depends on the positional relationship of the x-ray source 2, the specimen S, and the detector 4, and the scanning pitch of the specimen S in the Y axis direction (that is, on the thickness of the sliced plane). Meanwhile, the evaluation regions 600 exist in various places on the specimen S in various sizes, and in various shapes. Thus, by applying the lattice grids 650 to the evaluation regions 600, the processing for selecting a sliced plane can be performed efficiently.

2. Inspection Time Shortening Processing

Hereinafter, setting processing for an evaluation region, setting processing for a lattice grid, sliced plane and reference plane selection processing, and x-ray CT inspection processing included in inspection time shortening processing when performing a partial scan will each be described in detail.

2.1. Setting Processing for an Evaluation Region

The evaluation region setting unit 561 of the inspection control unit 56 sets the position and range (size) of the evaluation regions 600 of the specimen S. The evaluation region setting unit 561 sets the position and range of the evaluation regions 600 based on information input manually by an operator based on design information from three-dimensional CAD or the like, information from simulation results, described hereinafter, information based on measurement data performed in the past, and the like. That is, the evaluation region setting unit 561 sets three-dimensional coordinate data representing the position and range of the evaluation regions 600 in a three-dimensional coordinate system in the design information, and stores it in the data accumulation unit 58.

In a simulation a perfect prediction is impossible, but information such as regions in which there is a possibility that drawn cavities or the like will occur is effectively utilized. The input information necessary for a simulation is three-dimensional data representing the shape of the specimen S; from this three-dimensional data a mesh for calculation is created, and a pouring and solidifying simulation is performed. The simulation results are quantitative data representing the degree and place in which there is a possibility of drawn cavities or the like occurring. Regarding drawn cavities, there is a publicly-known evaluation index called the Niyama parameter; using the Niyama parameter, the places in which drawn cavities occur can be predicted to a degree.

2.2. Setting Processing for a Lattice Grid

The lattice grid setting unit 562 sets the lattice grids 650 so that the size is larger than a voxel, and smaller than the size of the evaluation regions 600, as described above. When the lattice grids 650 are set, the lattice grid setting unit 562 makes the evaluation region 600 into a lattice grid and sets a gridified evaluation region 610 by dividing the region including the evaluation regions 600 using the lattice grids 650.

Note that the lattice grid setting unit 562 can also set the lattice grids 650 according to the operation of an operator. For example, in a case where an investigation result is analyzed for a small evaluation region 600, high accuracy analysis results can be obtained by providing a lattice grid 650 more densely by setting the size of the lattice grid 650 smaller than normal.

Figure 5A:
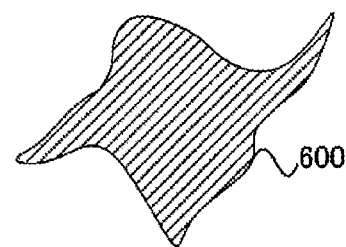
FIGS. 5A to 5D are figures schematically illustrating in two dimensions the setting of a gridified evaluation region.
Figure 5B:
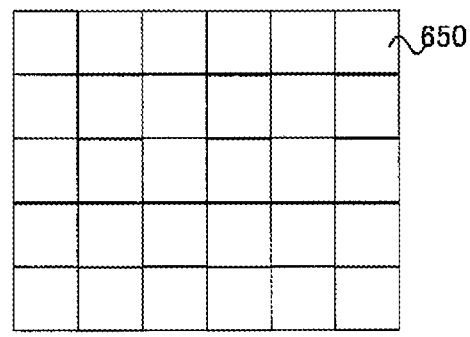
Figure 5C:
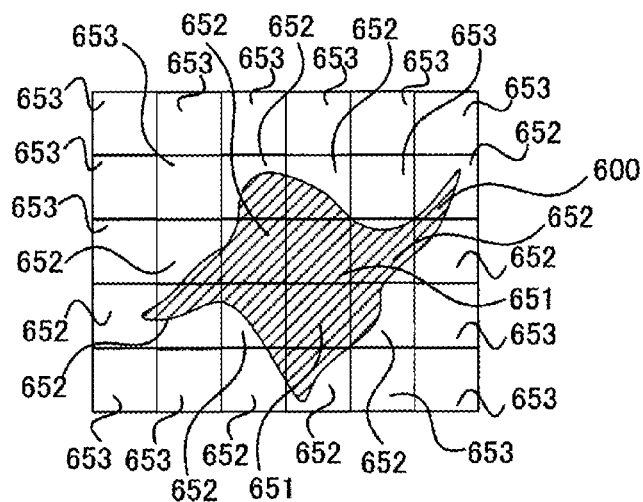
Figure 5D:
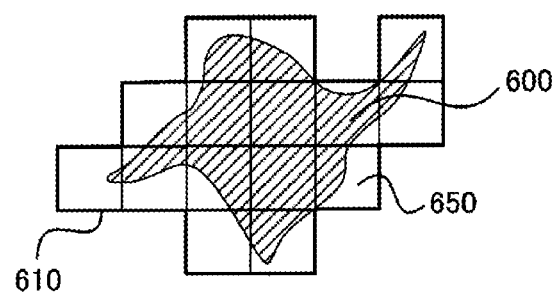

A concept for setting the gridified evaluation region 610 is schematically illustrated in FIGS. 5A to 5D. Note the FIGS. 5A to 5D illustrate the evaluation region 600, the lattice grid 650, and the gridified evaluation region 610, which have three-dimensional shapes, in a two-dimensional shape with the object of facilitating understanding. FIG. 5A illustrates one evaluation region 600, and FIG. 5B a plurality of set lattice grids 650. The lattice grid setting unit 562 applies (overlays) the lattice grids 650 to the evaluation region 600. As described above, the individual lattice grids 650 have a size smaller than the size of the evaluation region 600. Thus, as illustrated in FIG. 5C, a lattice grid 651 superimposing the evaluation region 600 in the entire region, a lattice grid 652 superimposing in one portion of the region, and a lattice grid 653 in which no superimposing region exists are formed among the plurality of lattice grids 650. The lattice grid setting unit 562 combines the lattice grid 651 superimposing the evaluation region 600 in the entire region, and the lattice grid 652 superimposing in a portion of the region together. As a result, as illustrated in FIG. 5D, the gridified evaluation region 610, which makes the evaluation region 600 into a lattice grid, is set by the lattice grid setting unit 562.

Figure 6A:
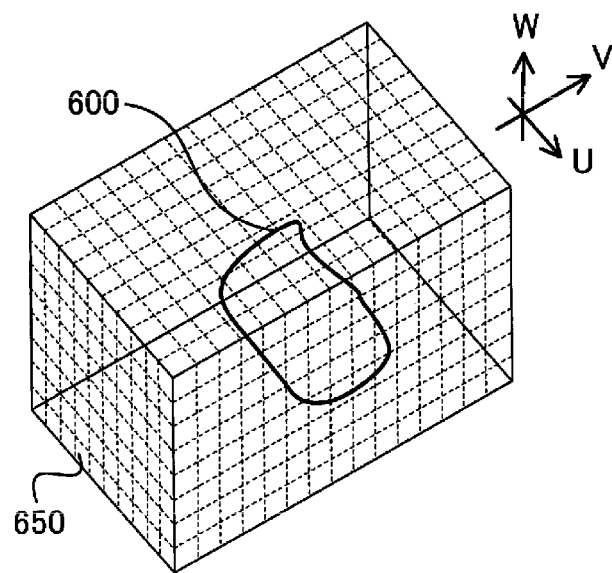
FIGS. 6A and 6B are figures illustrating a gridified evaluation region set in three dimensions.
Figure 6B:
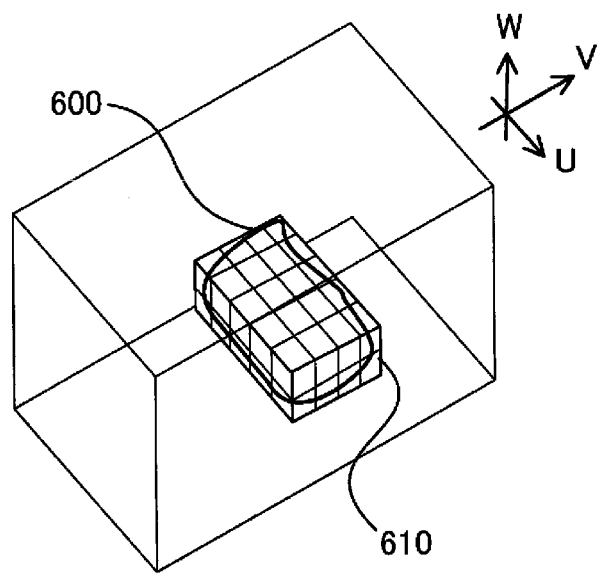

An example in a case where setting of the gridified evaluation region 610 is performed on a three-dimensional evaluation region 600 is schematically illustrated in FIGS. 6A and 6B. Note that in FIGS. 6A and 6B, the specimen S is omitted from the drawing. FIG. 6A illustrates a case where, for example, one evaluation region 600 is set. FIG. 6B illustrates a gridified evaluation region 610 generated by making this evaluation region 600 into a lattice grid. Note that FIG. 6B is drawn omitting the lattice grid 650 except the lattice grid 650 included in the gridified evaluation region 610 for convenience of drawing.

When the lattice grid setting unit 562 makes the three-dimensional evaluation region 600 into a lattice grid, as described above, data transformed from the three-dimensional coordinate data of the evaluation region 600 stored in the data accumulation unit 58 to coordinate values in a UVW coordinate system represented by the units of the lattice grid 650 is also stored in the data accumulation unit 58.

2.3. Sliced Plane and Reference Plane Setting Processing

The sliced plane setting unit 561 sets a reference plane and a sliced plane when partially scanning the specimen S. The sliced plane setting unit 561 sets a reference plane so that it is configured from a plane and points including reference positions in design information from, for example, three-dimensional CAD data or the like. This reference plane is used to match a reference plane in design information from three-dimensional CAD data or the like and a reference plane when placing and inspecting the specimen S on the placement stage 30. Furthermore, three-dimensional shape information for the region including the reference plane acquired using a partial scan or a full scan can also be used in position matching the lattice grid 650 and shape information for the specimen S.

The sliced plane selection unit 563 selects a sliced plane to measure the gridified evaluation region 610 according to the procedure of sliced plane selection described hereinafter. Below, a description of sliced plane selection will be performed by dividing it into the following (1) through (7).

Figure 7A:
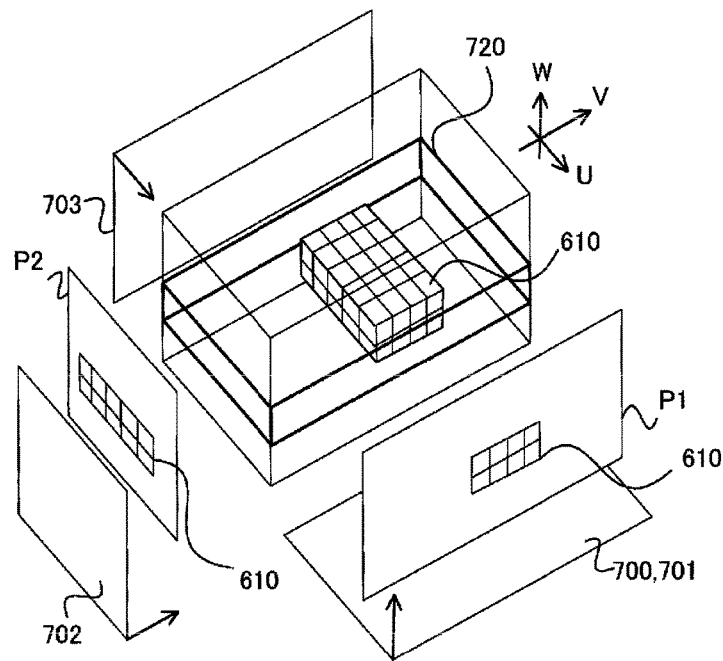
FIGS. 7A and 7B are figures schematically illustrating the selection of a sliced plane for the gridified evaluation region.

(1) A case where there is one gridified evaluation region (2) A case where there are a plurality of gridified evaluation regions (3) A case where a plurality of gridified evaluation regions can be seen as one evaluation region (4) A case where an evaluation region has a settable range (5) A case where evaluation regions are grouped according to the direction of extension of the evaluation region (6) A case where evaluation regions are grouped according to the magnification of the transmission image (7) A case based on simulation results (1) A Case where there is One Gridified Evaluation Region FIG. 7A schematically illustrates projection planes P1, P2 each projecting the gridified evaluation region 610 illustrated in FIG. 6B in the VW plane and the WU plane. By using the projection plane P1 parallel to the VW plane, a sliced plane candidate 701 displacing in the W direction and a sliced plane candidate 702 displacing in the V direction can be compared. Further, by using the projection plane P2 onto a plane parallel to the WU plane, a sliced plane candidate 702 displacing in the V direction and a sliced plane candidate 703 displacing in the U direction can be compared. Note that in FIG. 7A, an arrow facing the direction of displacement is given illustrating the displacement direction for each of the sliced plane candidates 701, 702, and 703. Note that in the present embodiment, the sliced plane candidate 703 selects sliced planes mutually intersecting as candidates. Note that in the present embodiment, the VW plane, the WU plane, and the UV plane are used, and each mutually differ by 90°. The angle formed by each plane is not limited to 90°, and may, for example, be 80°, 70°, 60°, 50°, 40°, 30°, 20°, 10°, or 5°. Further, the sliced plane candidate 703 may have a predetermined region having a predetermined width in a direction orthogonal to the VW plane rather than the VW plane. In a case where the sliced candidate plane 703 is selected from a plurality of predetermined regions, each of the plurality of predetermined regions may intersect. For example, the normal lines for surface for a plurality of predetermined regions may each intersect.

Note that in the present specification, the sliced plane candidates 701, 702, 703 are used for descriptive purposes to describe the procedure of sliced plane selection, and are not actually used for processing for selecting a sliced plane.

A sliced plane candidate with the smallest amount of displacement is set as the sliced plane 700 when performing a partial scan from among the amounts of displacement when each of the sliced plane candidates 701 through 703 is displaced in a state intersecting with the gridified evaluation region 610. Next, a description will be performed using the projection plane P1 parallel to the VW plane.

Figure 7B:
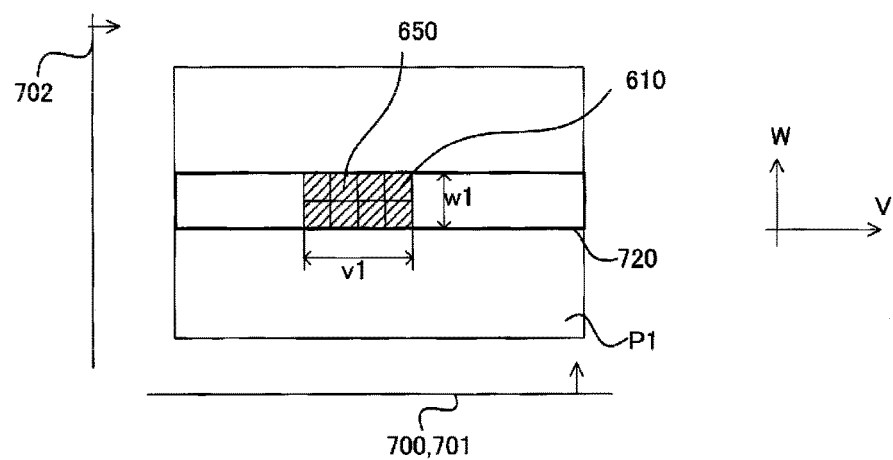

FIG. 7B schematically illustrates the projection plane P1, the gridified evaluation region 610VW on the projection plane P1, and the sliced plane candidates 701, 702. The gridified evaluation region 610VW is configured by lattice grids 650, four in the V direction and two in the W direction. Note that in FIG. 7B, the displacement direction of the sliced plane candidates 701 and 702 are each illustrated with arrows. In a case where the gridified evaluation region 610 is inspected through the sliced plane candidate 701, a length w1 in the W direction, which is the displacement direction for the sliced plane candidate 701, that is, the number of lattice grids 650 aligned along the W direction (in the example in FIG. 7B, two) will be the amount of displacement for the sliced plane candidate 701 with regard to the grid evaluation region 610. The amount of displacement is proportional to the inspection time required when inspecting the gridified evaluation region 610 along the W direction.

When scanning the gridified evaluation region 610 through the sliced plane candidate 702, a length v1 in the V direction, which is the displacement direction of the sliced plane candidate 702, that is, the number of lattice grids 650 aligned along the V direction (in the example in FIG. 7B, four) will be the amount of displacement for the sliced plane candidate 702 with regard to the grid evaluation region 610. In the example illustrated in FIG. 7B, the amount of displacement of the sliced plane candidate 701 in the W direction (corresponding to the two lattice grids 650) is small in comparison with the amount of displacement of the sliced plane candidate 702 in the V direction (corresponding to the four lattice grids 650). As described above, because the inspection time for the specimen S is proportional to the amount of displacement of the sliced plane 700, according to the evaluation by the projection plane P1, it can be understood that in a case where it is inspected through the sliced plane candidate 701, the inspection time would be shorter compared to a case where it is inspected through the sliced plane candidate 702.

Similarly, by using the projection plane P2 onto the WU plane, an amount of displacement for the sliced plane candidate 703 is similarly sought, is compared with the amount of displacement of the aforementioned sliced plane candidate 701, and sliced plane candidate with the smaller amount of displacement is selected as the sliced plane. In a case where the amount of displacement of the sliced plane candidate 701 is small compared to the sliced plane candidate 703, the sliced plane candidate 701 is selected as the sliced plane 700 for the gridified evaluation region 610. In other words, the sliced plane candidate that displaces along the direction in which the length of the gridified evaluation region 610 (that is, the direction in which the lattice blocks 650 are aligned) is short is selected as the sliced plane 700. By the sliced plane 700 being selected as described above, as illustrated in FIGS. 7A and 7B, a region 720 enclosed by a thick frame is the region that will be scanned when inspecting the gridified evaluation region 610 through the sliced plane 700 (hereinafter called the scan region).

(2) A Case where there are a Plurality of Gridified Evaluation Regions

Figure 8A:
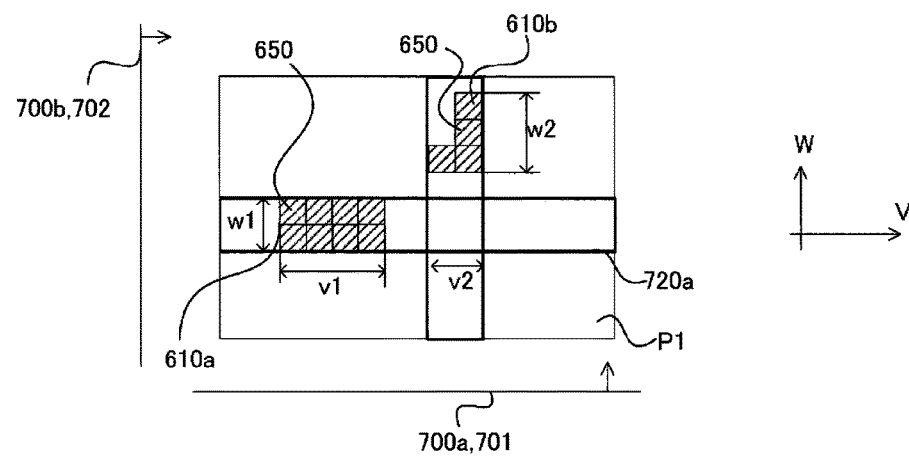
FIGS. 8A and 8B are figures schematically illustrating the selection of a sliced plane for a plurality of gridified evaluation regions.

The principles of selection for the sliced plane 700 in a case where a plurality of gridified evaluation regions are selected will be described with reference to FIGS. 8A and 8B. FIG. 8A illustrates a state where two gridified evaluation regions, a first gridified evaluation region 610a and a second gridified evaluation region 610b are set, with each projected onto a projection plane P1 parallel to the VW plane. The first gridified evaluation region 601a is configured by lattice grids 650, four in the V direction and two in the W direction, and the second gridified evaluation region 610b is configured by lattice grids 650, two in the V direction and three in the W direction. That is, in the first gridified evaluation region 610a, the length v1 in the V direction is greater than the length w1 in the W direction, and in the second gridified evaluation region 610b, the length v2 in the V direction is shorter than the length w2 in the W direction.

For the first gridified evaluation region 601a, the amount of displacement of the sliced plane candidate 701 and the amount of displacement of the sliced plane candidate 702 are compared, similarly to the case in FIGS. 7A and 7B. Because the first gridified evaluation region 601a has fewer lattice grids 650 aligned in the W direction, the sliced plane candidate 701, which displaces in the W direction, is selected as the first sliced plane 700a for the first gridified evaluation region 601a. Thus, for the first gridified evaluation region 601a, it will be scanned in the range of the first scan region 720a.

For the second gridified evaluation region 601b, as well, the amount of displacement of the sliced plane candidate 701 and the amount of displacement of the sliced plane candidate 702 are similarly compared. Because the second gridified evaluation region 601b has fewer lattice grids 650 aligned in the V direction, the sliced plane candidate 702, which displaces in the V direction, is selected as the second sliced plane 700b for the second gridified evaluation region 601b. Thus, for the second gridified evaluation region 601b, it will be scanned in the range of the second scan region 720b. That is, in a case where a plurality of gridified evaluation regions 610 are set, for each gridified evaluation region 610, the sliced plane candidate that displaces along the direction with the shortest length is selected as the sliced plane 700.

Thus, in a case where a plurality of sliced planes 700 with different directions of displacement are selected, there is a need to change the placement orientation of the specimen S on the placement stage 30, as is described hereinafter, when performing an actual inspection.

Figure 8B:
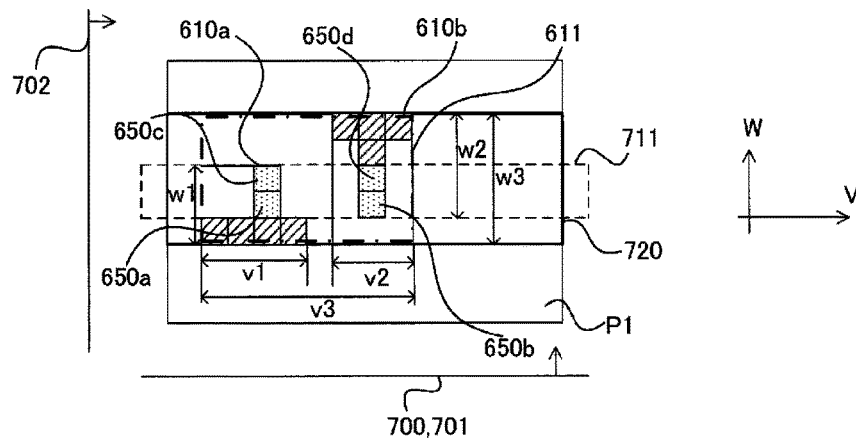

(3) A Case where a Plurality of Gridified Evaluation Regions can be Seen as One Evaluation Region In a case where a plurality of gridified evaluation regions 610 are set as is illustrated in FIGS. 8A and 8B, a sliced plane 700 is selected with the plurality of gridified evaluation regions 610 seen as one gridified evaluation region. FIG. 8B illustrates a state in which a first gridified evaluation region 610a and a second gridified evaluation region 610b are set, with each projected onto the projection plane P1 parallel to the VW plane. The length v1 of the first gridified evaluation region 601a in the V direction corresponds to four lattice grids 650, and the length w1 in the W direction corresponds to three lattice grids 650. The length v2 of the second gridified evaluation region 610b in the V direction corresponds to three lattice grids 650, and the length w2 in the W direction corresponds to four lattice grids 650. That is, in the first gridified evaluation region 610a, the length v1 in the V direction is longer than the length w1 in the W direction, and in the second gridified evaluation region 610b, the length v2 in the V direction is shorter than the length w2 in the W direction.

In this case, if the procedure described using FIG. 8A is followed, the sliced plane candidate 701 whose amount of displacement along the W direction is w1 for the first gridified evaluation region 610 and the sliced plane candidate 702 whose amount of displacement along the V direction is v2 for the second gridified region 610b are each selected as the sliced planes 700. However, in a case where the sliced plane candidate 701 displaces a region 711 enclosed in a dashed line in FIGS. 8A and 8B, it will create a state in which a portion of the first gridified evaluation region 610a and a portion of the second gridified evaluation region 610b exist together on the sliced plane candidate 701. That is, a lattice grid 650a for the first gridified evaluation region 610a and a lattice grid 650b for the second gridified evaluation region 610b, as illustrated in FIG. 8B illustrated with dots, exist in an identical sliced plane orthogonal with the W axis. Further, a lattice grid 650c for the gridified evaluation region 610a and a lattice grid 650d for the gridified evaluation region 610b, illustrated with dots, exist in an identical sliced plane orthogonal to the W axis.

In a case wherein the sliced plane candidate 701 is used to scan the projection plane P1, the lattice grids 650a and 650b from among the gridified evaluation region 610a and 610b can be scanned with identical timing, and the lattice grids 650c and 650d can be scanned with identical timing. In such a case, the possibility is determined of the first gridified evaluation region 610a and the second gridified evaluation region 610b being combined and seen as one gridified evaluation region 611, selecting the sliced plane 700 based on the amount of displacement of the sliced plane candidate 701 in the V direction and the amount of displacement of the sliced plane candidate 702 in the W direction. In the example in FIG. 8B, the length v3 of the gridified evaluation region 611 in the V direction corresponds to seven or more lattice blocks 650, and the length w3 in the W direction corresponds to five lattice blocks 650. Thus, the first gridified evaluation region 610a and the second gridified evaluation region 610b are combined and seen as one gridified evaluation region 611, it is determined that selecting the sliced plane candidate 701, whose amount of displacement in the W direction is smaller, as the sliced plane 700 will lead to a shorter inspection time, and the gridified evaluation region 611 including the first gridified evaluation region 610a and the second gridified evaluation region 610b is inspected in a scan range 720.

Based on the principles described above, the sliced plane selection unit 563 selects a sliced plane 700 for the evaluation region 600 set on the specimen S. The sliced plane selection unit 563 reads three-dimensional coordinate data for the gridified evaluation region 610 in the UVW coordinate system for each lattice grid 650 out from the data accumulation unit 58. The sliced plane selection unit 563 calculates an amount of displacement using three-dimensional coordinate data for the length of the gridified evaluation region 610 in the U direction, the V direction, and the W direction, and selects the sliced plane 700 that displaces in the direction with the shortest length.

In a case where a plurality of gridified evaluation regions 610 are set, the sliced plane selection unit 563 determines if there are planes on which a portion of a gridified evaluation region 610 and a portion of another gridified evaluation region 610 simultaneously exist among the different gridified evaluation regions 610. That is, the sliced plane selection unit 563 determines whether at least one coordinate data from among the U coordinate value, the V coordinate value, and the W coordinate value matches in the different gridified evaluation regions 610. In the different gridified evaluation regions 610, in a case where at least one coordinate data matches, the sliced plane selection unit 563 selects the sliced plane 700 that displaces in the direction with the shortest length for one gridified evaluation region 611 generated by combining the gridified evaluation regions 601. In a case where the different gridified evaluation regions 610 in which at least one coordinate value matches do not exist, the sliced plane selection unit 563 selects the sliced plane 700 that displaces in the direction with the shortest length for individual gridified evaluation regions 610.

Note that even in a state where a portion of a plurality of gridified evaluation regions exist together on one sliced plane candidate, it may not always be able to shorten the inspection time by combining the plurality of gridified evaluation regions and by seeing them as one evaluation region. A determination of whether to combine a plurality of gridified evaluation regions and see them as one evaluation region is decided based on a comparison of the total of the amounts of displacement of the sliced planes in a case where a plurality of gridified evaluation regions are separately inspected with the amounts of displacement of the sliced planes in a case where a plurality of gridified evaluation regions are combined.

The setting processing for the sliced plane 700 in a case where a cylinder block for an engine is the specimen S, and an evaluation region 600 is set will be described with reference to FIGS. 9A and 9B. As described about using FIG. 3, three types are set as the evaluation region 600: an evaluation region 601 of the crankshaft journal portion, an evaluation region 602 of the cast pull pin, and an evaluation region 603 of the liner portion. Four places are set as the evaluation region 601 of the crankshaft journal portion, which is a mechanically important site, eight places as the evaluation region 602 of the cast pull pin, which is a site where the temperature cycle is intense, and six places as the evaluation region 603 of the liner portion. Note that the shape of the liner portion is cylindrical, but since the degree of adhesion can also be determined in a partial inspection rather than the full circumference of the cylinder, two places interposing each cylinder shape are set, for a total of six places.

The sliced plane selection unit 563 sets the sliced plane 700 according to the procedure described above based on what direction the alignment of the individual evaluation region 600 and evaluation region 600 extend. As illustrated in FIG. 9A, the amount of displacement of the sliced plane 700 in a case where a sliced plane 700 that is parallel to the WU plane and displaces in the V direction is set is smaller compared to cases where sliced planes 700 in the VW plane or the UV plane are set. FIG. 9B illustrates sliced ranges 720a, 720b, 720c for inspecting each of the evaluation regions 601, 602, 603 for the crankshaft journal, the cast pull pin, and the liner portion decided according to the set sliced plane 700. In a case where a partial scan is performed on the specimen S, irradiation of x-ray in the sliced ranges 720a, 720b, 720c is performed as is described hereinafter; irradiation in a range beyond these sliced ranges is not performed.

Note that the selected sliced plane 700 and sliced range 720 are displayed on the display monitor 6, and one configured so that the selection state of the sliced plane 720 and the sliced range 720 are observable by the operator is included in one aspect of the present invention.

The sliced plane 700 is selected based on the procedure described above, but the sliced plane selection unit 563 can take into consideration the settable range of the evaluation region 600 and perform selection of the sliced plane 700 by resetting the position and the like of the evaluation region 600 set by the evaluation region setting unit 561. The settable range is a range in which a little deviation in the position and size is allowed, even if the position and size of the evaluation region 600 are not necessarily exactly the input values. For example, because the crankshaft journal portion on the cylinder block of the engine has a degree of thickness in the crankshaft axis direction (V direction), the impact on the evaluation region 601 is small if it deviates within this range. In other words, the evaluation region 600 having a settable range can displace (move) a position inside the settable range. By displacing the evaluation region 600 inside the settable range, the amount of displacement of the sliced plane 700, that is, the width of the sliced range 720 can be shortened, making possible shortening the inspection time. Note that the evaluation region 602 of the cast pull pin in the cylinder block of the engine must be in the position set in the V direction. That is, it is a fixed evaluation region 600 that does not have a settable range and whose position cannot be displaced.

Note that when the evaluation region 600 described above is set, the settable range may also be configured to be able to be input.

(4) A Case where an Evaluation Region has a Settable Range

The selection of the sliced plane 700 in a case taking into consideration the settable range will be described with reference to FIGS. 10A and 10B and FIGS. 11A to 11C.

Figure 10A:
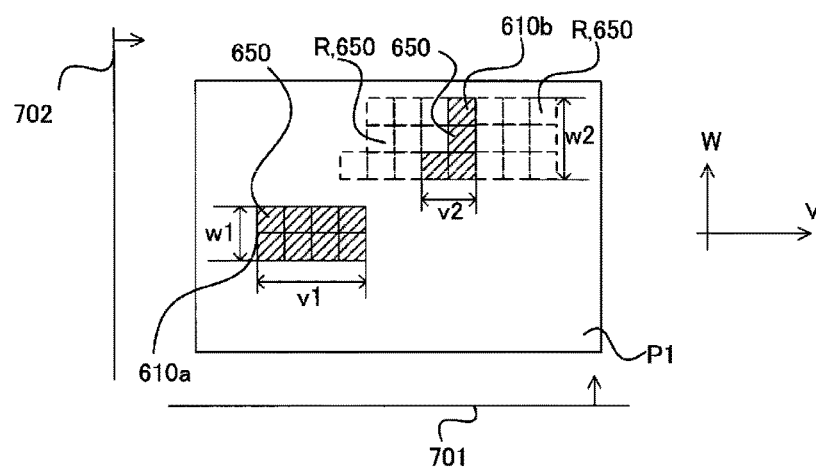
FIGS. 10A and 10B are figures schematically illustrating the selection of a sliced plane in a case where the evaluation region has a settable range.

FIG. 10A illustrates a state where a first gridified evaluation region 610a and a second gridified evaluation region 610b are set, and are each projected on the projection plane P1 parallel to the VW plane, similarly to the case in FIG. 8A. The length v1 of the first gridified evaluation region 601a in the V direction corresponds to four lattice grids 650, and the length in the W direction to two; the length v2 of the second gridified evaluation region 610b in the V direction corresponds to two lattice grids 650, and the length w2 in the W direction to three. It is assumed that the second gridified evaluation region 610b has a settable range R corresponding to three lattice blocks 650 each on the +side and the—side along the V direction, and the first gridified evaluation region 610a does not have a settable range. Note that in FIG. 10A, the lattice block 650 corresponding to the settable range R is illustrated with a dashed line.

In the present embodiment, a case where the settable range R is set in the V direction is described in an example. In FIG. 10A, an amount of displacement V1 with regard to the first gridified evaluation region 610a and an amount of displacement V2 with regard to the second gridified evaluation region 610b in the V direction are set. In this case, if a settable range R is not set in the V direction, the amount of displacement of the sliced plane in the V direction will be V1+V2. Meanwhile, in the present embodiment, settable ranges R of three on the +side, three on the—side in the V direction are set for the second gridified evaluation region 610b. In this case, in a case where the second gridified evaluation region 610b is moved by three to the V direction+side from the state illustrated in FIG. 10A, the amount of displacement of the set sliced plane in the V direction of the first gridified evaluation region 610a and the second gridified evaluation region 610b will be V1 and V2. Meanwhile, in a case where it is moved by three to the V direction—side from the state illustrated in FIG. 10A, in a case where the sliced plane set by the first gridified evaluation region 610a is displaced in the V direction, are region is set where, not only the first gridified evaluation region 610a is detected, a portion of the second gridified evaluation region 610b is detected. In the case stated in FIG. 10B, the lattice block disposed furthest to the +side among the four lattice block region set in the V direction of the first gridified evaluation region 610a and the lattice block disposed furthest to the—side of the second gridified evaluation region 610b overlap in the V direction. Thus, in FIG. 10B, the first gridified evaluation region 610a and the second gridified evaluation region 610b are combined together and seen as one gridified evaluation region 611, and the sliced plane 700 is selected based on the amount of displacement of the sliced plane candidate 701 in the V direction and the amount of displacement of the sliced plane candidate 702 in the W direction.

Figure 10B:
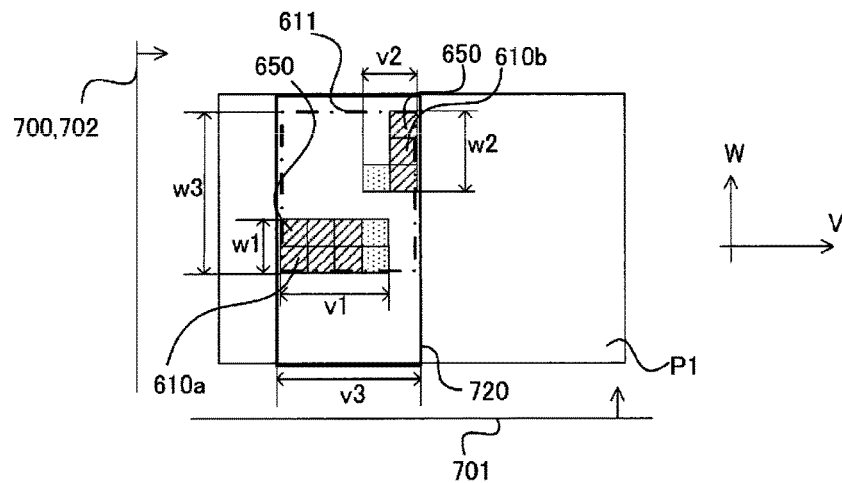

In the example of FIG. 10B, the length v3 of the gridified evaluation region 611 in the V direction corresponds to five lattice blocks 650. Thus, the amount of displacement in the V direction can be made small compare to prior to displacement of the settable range R of the second gridified evaluation region 610b. That is, in a case where another gridified evaluation region 610 is set in the settable range R of the gridified evaluation region 610 having a settable range R, the gridified evaluation region 610 having a settable range R can be displaced, and setting of the sliced plane 700 viewing them as one gridified evaluation region 611.

Figure 11A:
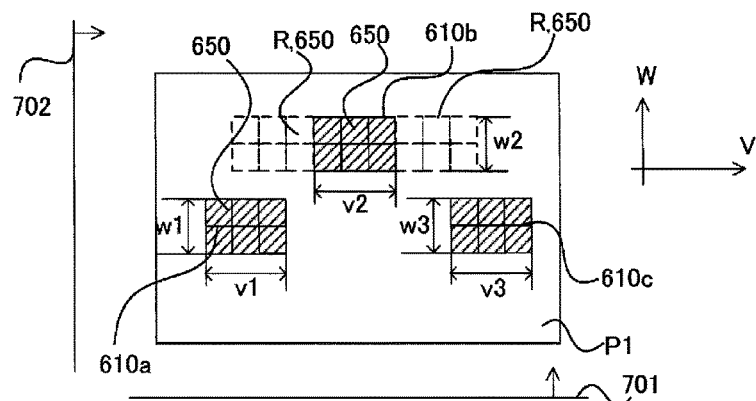
FIGS. 11A to 11C are figures schematically illustrating the selection of a sliced plane in a case where the evaluation region has a settable range.

The procedure for selecting a sliced plane 700 in a case where a plurality of gridified evaluation regions 610 are set inside the settable range R of a gridified evaluation region 610 having a settable range R will be described with reference to FIGS. 11A to 11C. In FIG. 11A, the second gridified evaluation region 610b has a settable range R, whereas the first gridified evaluation region 610a and a third gridified evaluation region 610c do not have a settable range. The second gridified evaluation region 610b is displacable by three lattice grids 650 each to the V direction+side and—side as the settable range R.

Figure 11B:
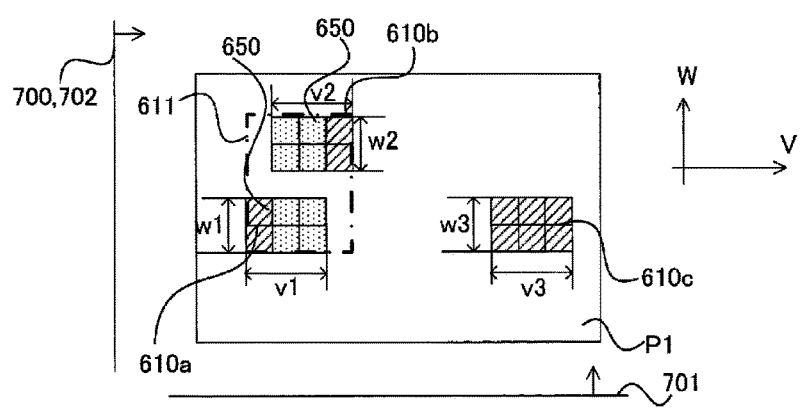

FIG. 11B illustrates a case where the second gridified evaluation region 610b is only displaced by three lattice grids 650 corresponding to the settable range R to the V direction—side. In this case, the lattice grid 650 for the first gridified evaluation region 610a and the lattice grid 650 for the second gridified evaluation 610b illustrated with dots exist on an identical sliced plane candidate 702. That is, as is illustrated in the drawing, in each of the first gridified evaluation region 610a and the second gridified evaluation region 610b, two lattice grids 650 aligned in the V direction can be inspected with similar timing by the displacement of the sliced candidate plane 702. Thus, in the gridified evaluation region 611 combining the first gridified evaluation region 610a and the second gridified evaluation region 610b after displacement, the amount of displacement of the sliced plane candidate 702 along the V direction corresponds to four lattice grids.

Figure 11C:
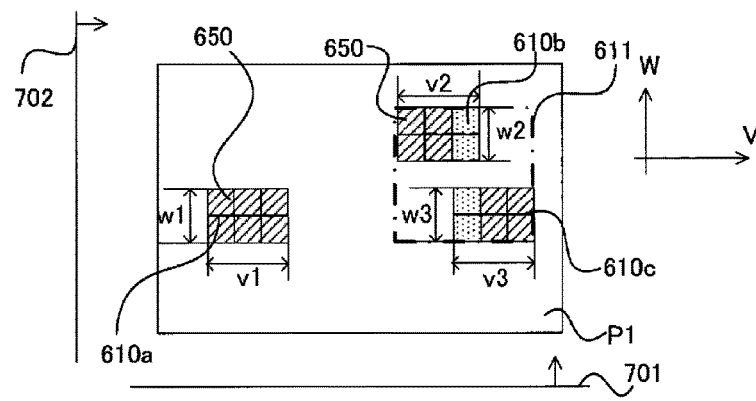

FIG. 11C illustrates a case where the second gridified evaluation region 610b is displaced by three lattice grids 650 corresponding to the settable range R to the V direction+side. In this case, the lattice grid 650 for the first gridified evaluation region 610a and the lattice grid 650 for the second gridified evaluation 610b illustrated with dots exist on an identical sliced plane candidate 702. That is, as is illustrated in the drawing, in each of the third gridified evaluation region 610a and the second gridified evaluation region 610b, one lattice grid 650 aligned in the V direction can be inspected with similar timing by the displacement of the sliced candidate plane 702. Thus, in the gridified evaluation region 611 combining the third gridified evaluation region 610c and the second gridified evaluation region 610b after displacement, the amount of displacement of the sliced plane candidate 702 along the V direction corresponds to five lattice grids.

This in the case illustrated in FIGS. 11A to 11C, as is illustrated in FIG. 11B, the second gridified evaluation region 610b is displaced in the direction of the first gridified evaluation region 610a, and the sliced plane candidate 702 to be displaced in the V direction is selected as the sliced plane 700. That is, by displacing the second gridified evaluation region 610b having a settable range R so that the length of the gridified evaluation region 611 combined into one becomes shorter, the amount of displacement of the sliced plane 700 can be made smaller.

Based on the procedure described above, the region resetting unit 567 resets the gridified evaluation region 610, taking into consideration the settable range R of the evaluation region 600 having a settable range R set by the specimen S, and the sliced plane selection unit 563 selects the sliced plane 700 using the reset gridified evaluation region 610. The region resetting unit 567 reads coordinate values for the gridified evaluation region 610 in the UVW coordinate system in lattice grid 650 units out from the data accumulation unit 58. In a case where a settable range R is set for the gridified evaluation region 610, the region resetting unit 567 determines whether another gridified evaluation region 610 exists in the settable range R using the coordinate values that were read out. That is, the region resetting unit 567 determines whether the difference between the coordinate values for the edge portion of a gridified evaluation region 610 having a settable range R and the coordinate values for the edge portion of another gridified evaluation region 610 that is fixed in the UVW directions is smaller than the settable range R.

In a case where the difference is smaller than the settable range R, the region resetting unit 567 determines that another gridified evaluation region 610 exists in the settable range R, displaces the gridified evaluation region 610 having a settable range R and resets the gridified evaluation region 610 so that the size that is shareable in the direction of the settable range R (a number of the lattice grids 650) is as large as possible. The sliced plane selection unit 563 calculates the length of the gridified evaluation region 610 reset by the region resetting unit 567 in the U direction, the V direction, and the W direction in UVW coordinates, and selects the sliced plane 700 whose amount of displacement in the direction of the shortest length is as small as possible.

Note that in the description above, a case in which a gridified evaluation region 610 having a settable range R was displaced towards a gridified evaluation region 610 not having a settable range R was given as an example, but a case in which gridified evaluation regions 610 having settable ranges R are both displaced is also included in one aspect of the present invention.

Figure 12A:
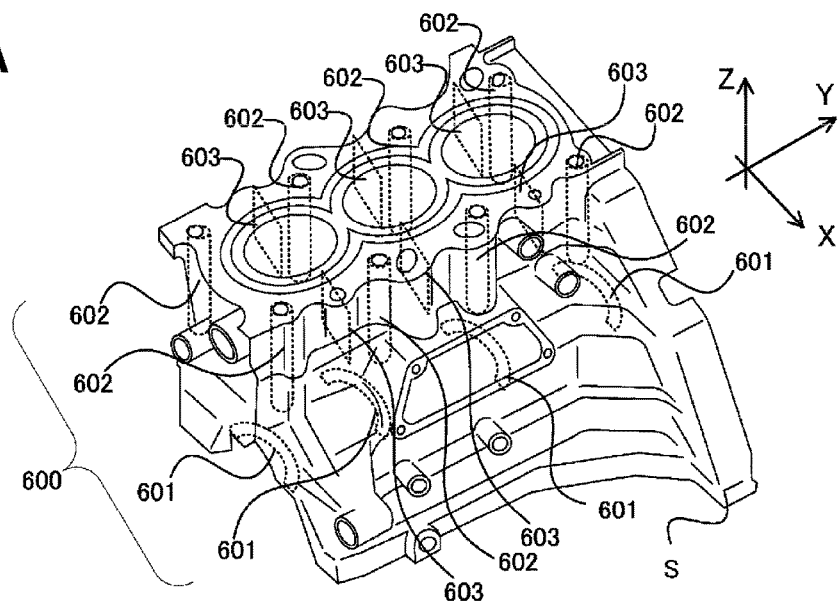
FIGS. 12A and 12B are figures illustrating an example of a sliced plane and a sliced range selected after taking into consideration the settable range of the evaluation region when inspecting a cylinder block for an engine as the specimen.
Figure 12B:
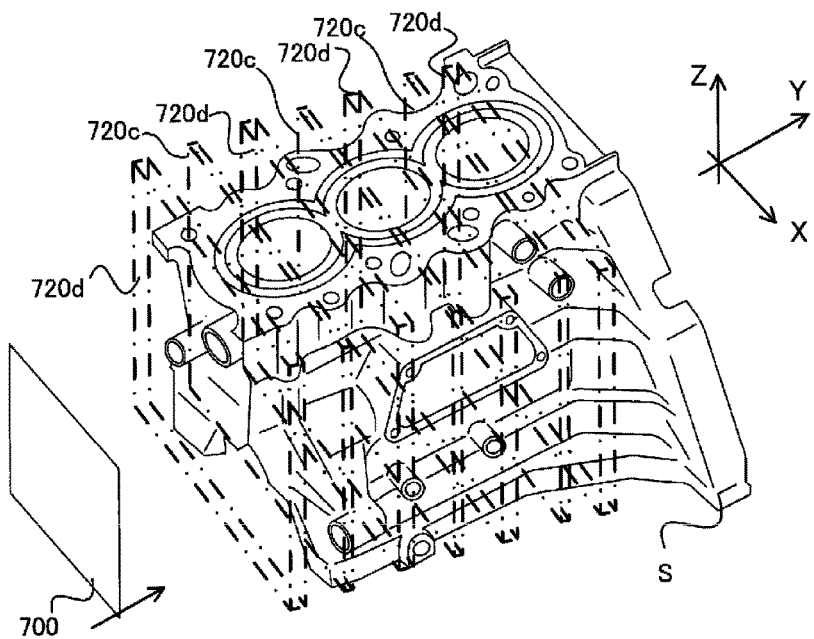

The setting processing for the sliced plane 700 in a case where a cylinder block for an engine is the specimen S, and an evaluation region 600 is set will be described with reference to FIGS. 12A and 12B. FIG. 12A illustrates evaluation regions 601, 602, 603 set on a specimen S similarly to the case illustrated in FIG. 3. As is described above, the evaluation region 601 for the crankshaft journal portion on the cylinder block of the engine can be displaced inside the settable range R along the V direction, but the evaluation region 602 for the cast pull pin cannot be displaced along the V direction. The region resetting unit 567 displaces the gridified evaluation region 610 corresponding to the evaluation region 601 in the V direction, and makes the position in the V direction shared between the gridified evaluation region 610 corresponding to the evaluation region 601 and the gridified evaluation region 610 corresponding to the evaluation region 602. Thus, as is illustrated in FIG. 12B, the sliced plane selection unit 563, as substitute for setting the sliced range 720a (see FIG. 9B) for the evaluation region 601 and the sliced range 720b (see FIG. 9B) for the evaluation region 602, sets a shared sliced range 720d for the evaluation region 601 and the evaluation region 602. Then, in a case where a partial scan is performed on the specimen S, irradiation of the sliced ranges 720c, 720d is performed by x-rays as is described hereinafter; irradiation is not performed in a range beyond the sliced ranges 720c, 720d with x-rays.

Figure 13A:
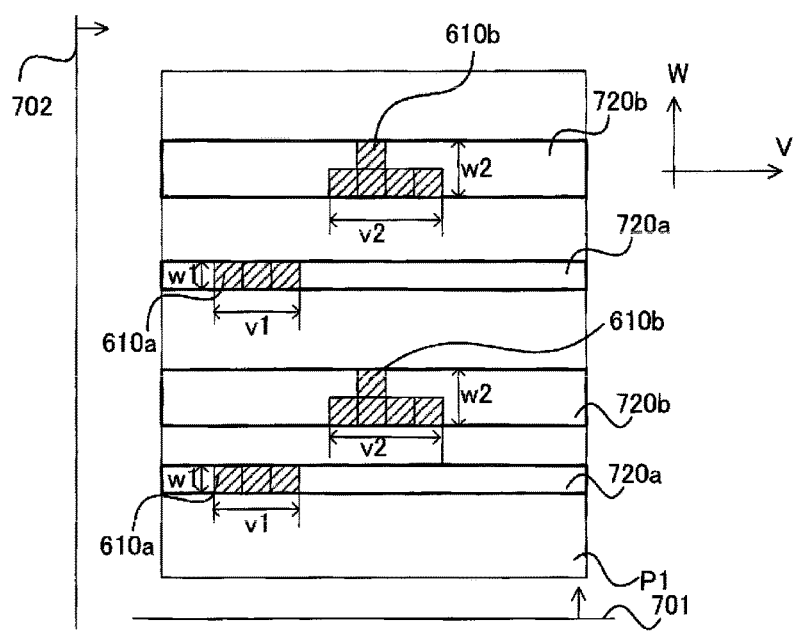
FIGS. 13A and 13B are figures schematically illustrating a case wherein a plurality of gridified evaluation regions are grouped.
Figure 13B:
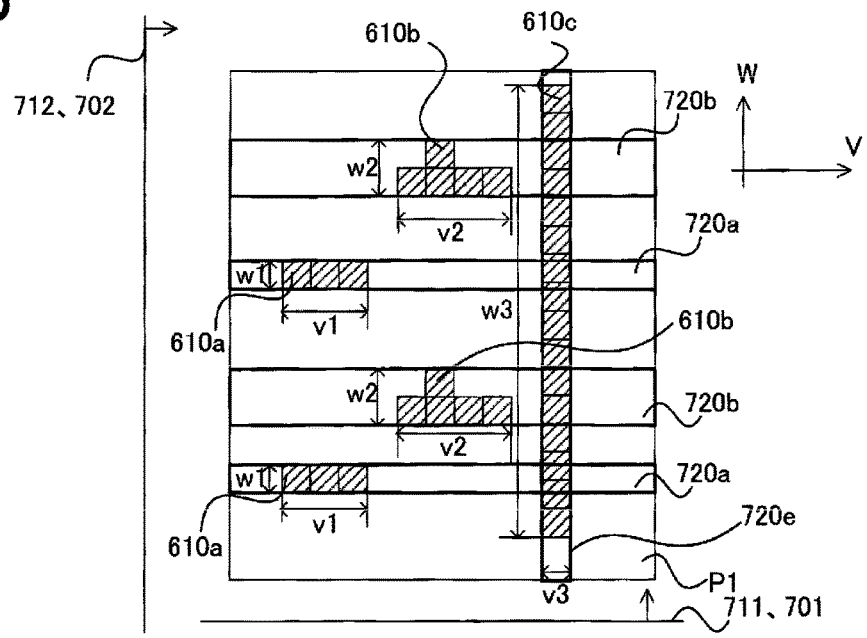

(5) A Case where Evaluation Regions are Grouped According to the Direction of Extension of the Evaluation Region A description will be performed using a conceptual drawing illustrated in FIGS. 13A and 13B. FIG. 13A schematically illustrates the projection plane P1 in a case where a plurality of first gridified evaluation regions 610a with the V direction as the longitudinal direction and a plurality for second gridified regions 610b with the V direction as the longitudinal direction are distributed. In the case illustrated in FIG. 13A, the amount of displacement displaced in the W direction and the amount of displacement displaced in the V direction are compared. That is, by performing processing in accordance with the various procedures described above, the sliced plane 700 displacing in the W direction is set, and sliced ranges 720a, 720b are set as illustrated in the drawing.

FIG. 13B schematically illustrates a case in which, in addition to the first gridified evaluation region 610a and second gridified evaluation region 610b scattered as illustrated in FIG. 13A, a third gridified evaluation region 610c is set with the W direction as the longitudinal direction. In FIG. 13B, the third gridified evaluation region 610c has a size corresponding to one lattice grid 650 in the V direction, and has a size corresponding to 16 lattice grids 650 in the W direction. The size of the third gridified evaluation region 610 in the W direction will be described as being nearly equivalent to the size of the specimen S in the W direction.

As illustrated in FIG. 13B, in a case where first, second and third gridified evaluation regions 610a, 610b and 610c are distributed, when the sliced plane 700 is displaced along the W direction, it becomes an amount of displacement of the number of lattice grids 650 (in the example in FIG. 13B, 16) along the W direction configuring the third gridified evaluation region 610c, substantially requiring similar inspection time to a case where a full scan is performed. That is, in a case where the sliced plane candidate 701 is selected as the sliced plane 700, the amount of displacement of the sliced plane 700 increases, which leads to an increase in inspection time compared to the amounts of displacement for the first gridified evaluation region 610a and the second gridified evaluation region 610b described above.

The third gridified evaluation region 610c has one lattice grid 650 in the V direction. For this reason, in a case where the sliced plane candidate 702 is displaced in the V direction as the sliced plane 700 and the third gridified evaluation region 610c is inspected, the amount of displacement is small compared to a case where the sliced plane 701 is displaced in the W direction. Thus, when a sliced plane 700 is displaced in the V direction for the third gridified evaluation region 610c and a sliced plane 700 is displaced in the W direction for the first and second gridified evaluation regions 610a and 610b, as described above, the amounts of displacement of the sliced plane displaced in the W direction (hereinafter called the first sliced plane 711) and the sliced plane displaced in the V direction (hereinafter called the second sliced plane 712) can be made smaller respectively. In this case, the first and second gridified evaluation regions 610a and 610b are grouped into a first group G1, and the third gridified evaluation region 610c is grouped into another second group G2. That is, a plurality of gridified evaluation regions 610 are grouped according to their size in the longitudinal direction of each gridified evaluation region 610, and the sliced plane 700 and the sliced region 720 whose amount of displacement of each group becomes smaller are selected.

Figure 14A:
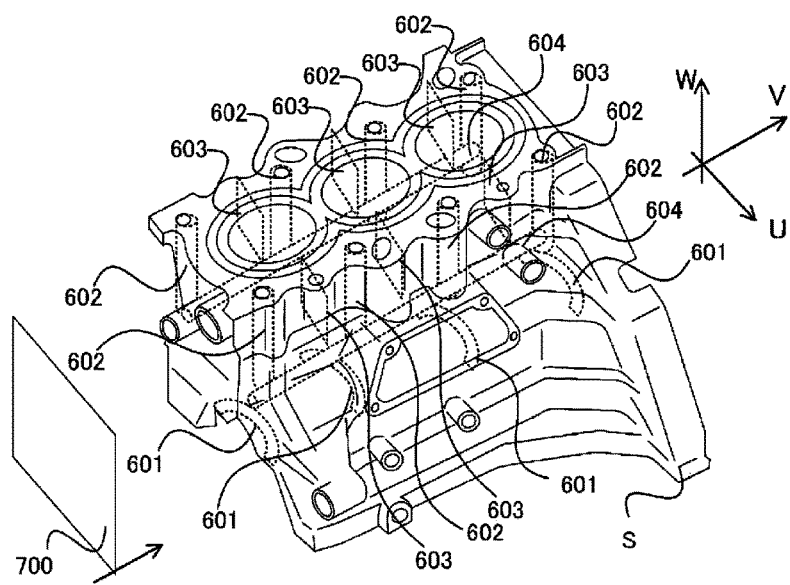
FIGS. 14A and 14B are figures illustrating an example of a sliced plane and a sliced range selected when inspecting a cylinder block for an engine as the specimen.
Figure 14B:
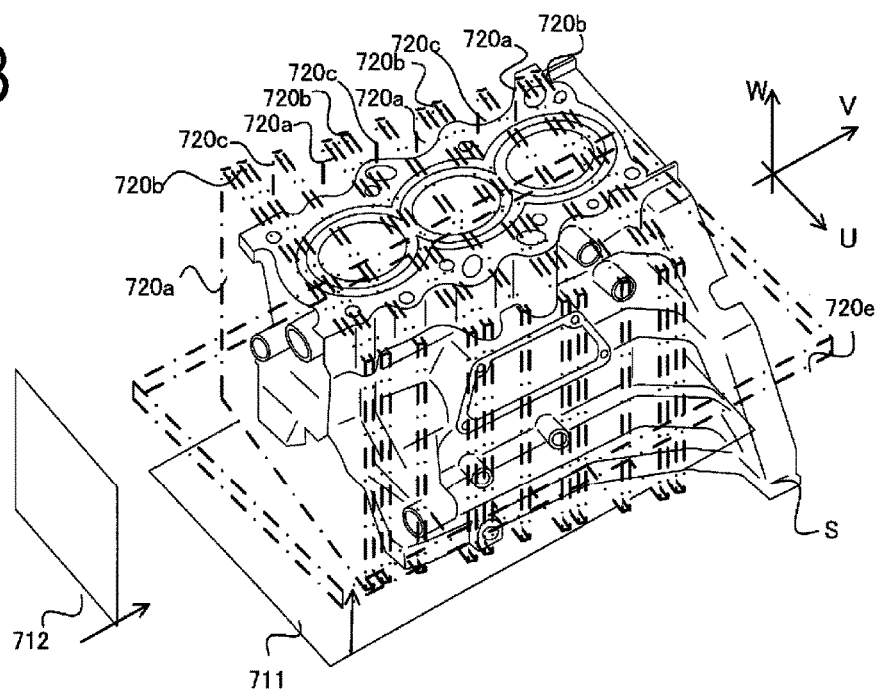

Below, particular processing will be described with reference to FIGS. 14A and 14B. FIGS. 14A and 14B illustrate a case where, in addition to the evaluation regions 601, 602, 603 set on a cylinder block of an engine as the specimen S illustrated in FIG. 3, each of two cooling channels is additionally set as an evaluation region 604. The evaluation region 604, which is a cooling channel, extends, for example, 300 mm in the V direction. As is illustrated in FIG. 14A, when the specimen S is placed on the placement stage 30 and inspected, the amount of displacement of the sliced plane 700 to inspect the evaluation region 604, which is a cooling channel, is at least 300 mm. For this reason, the inspection time increases.

The individual evaluation regions 601, 602, 603 for the crankshaft journal, cast pull pin, and liner illustrated in FIG. 14A generally extend in the W direction, generally are distributed being included in the WU plane, and are aligned discretely in the V direction. Meanwhile, the evaluation region 604, which is a cooling channel, extends in the V direction, and is included in the UV plane. The grouping unit 565 uses, for example, cluster analysis to group each of the evaluation regions 601, 602, 603, 604.

One example representing the variables for each of the evaluation regions 601, 602, 603, 604 by using cluster analysis is illustrated in FIG. 15. As is illustrated in FIG. 15, the individual characteristics for each of the evaluation regions 601, 602, 603, 604 (for example, thickness, direction of thickness, direction of extension, and extension length) and the alignment characteristics for a plurality of them (for example, alignment direction plane, number in plane, direction of alignment, and aligned number) are displayed as parameters. The grouping unit 565 quantifies three-dimensional information in UVW coordinates of the position and size of the evaluation region 600 set by the evaluation region setting unit 562, extracts them as parameters. The sliced plane setting unit 560 classifies these variables by the individual characteristics and alignment characteristics.

FIG. 15 illustrates a state where three-dimensional information about the evaluation regions 601 is classified in a case where a plane parallel to the WU plane is the alignment plane in the upper row of the column for the evaluation regions 601 for the crankshaft journal. That is, it illustrates that the individual evaluation regions 601 are 2 mm in thickness in the V direction and 70 mm in thickness in the U direction, one evaluation region 601 is included in one plane parallel to the WU plane, and four rows of planes of this sort are need in the V direction. On the lower row of the column for the evaluation regions 601, three-dimensional information about the evaluation regions 601 in a case where a plane parallel to the VW plane is the alignment plane is illustrated. Other evaluation regions 602, 603, 604 also have three-dimensional information similarly illustrated.

Figure 16A:
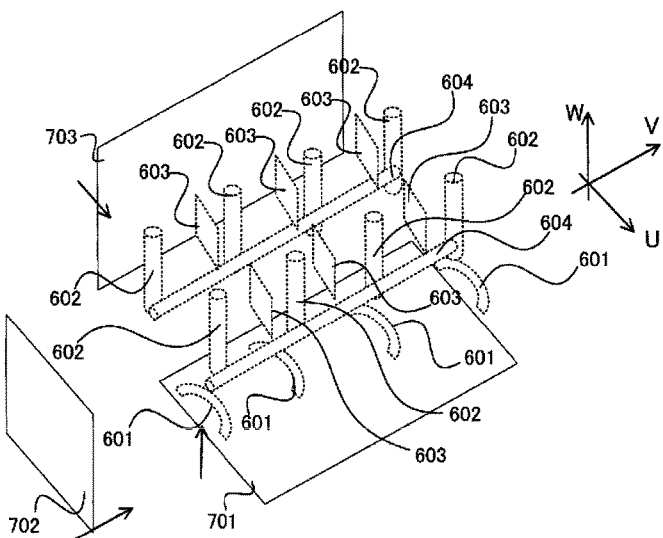
FIGS. 16A to 16C are figures schematically illustrating the processing at the time of cluster analysis.
Figure 16B:
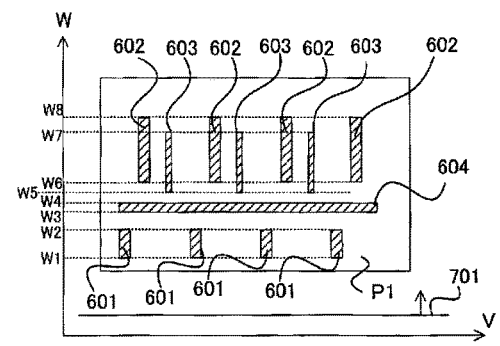
Figure 16C:
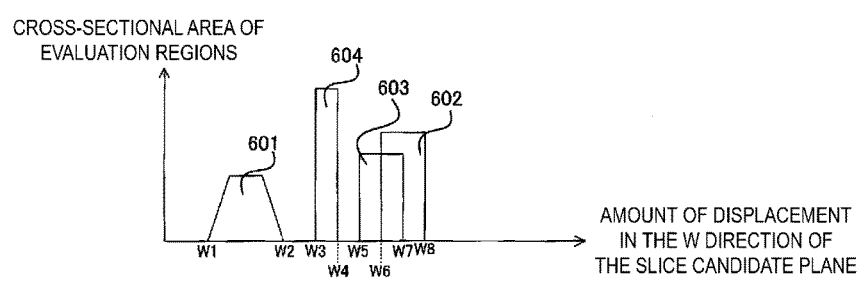

Grouping performed by the grouping unit 565 based on the results of the cluster analysis illustrated in FIG. 15 will be described with reference to FIGS. 16A to 16C. FIG. 16A is a diagram illustrating the evaluation regions 601, 602, 603, 604 and the sliced plane candidates 701, 702, 703 with UVW coordinates within the engine block, which is the specimen S illustrated in FIGS. 14A and 14B. FIG. 16B illustrates a state wherein gridified evaluation regions 610a, 610b, 610c, 610c each corresponding to evaluation regions 601, 602, 603, 604 are projected onto a projection surface P1 parallel to the VW plane. FIG. 16C illustrates a change in the cross-sectional area on the sliced plane candidate 701 for the gridified evaluation regions 610a, 610b, 610c, 610c that change according to the displacement of the sliced plane candidate 701 when the sliced plane candidate 701, which is parallel to the UV plane, is displaced in the W direction. Note that FIG. 16C illustrates the amount of displacement of the sliced candidate plane 701 in the W direction as the horizontal axis, and the cross-sectional area of the gridified evaluation regions 610a, 610b, 610c, 610c as the vertical axis.

The sliced plane candidate 701 is displaced to from the W direction-side to the +side, the W position of the sliced plane candidate 701 intersects with the gridified evaluation region 610a corresponding to the evaluation region 601 during displacing from W1 to W2 illustrated in FIG. 16B. Thus, the cross-sectional area of the gridified evaluation region 610a intersecting with the sliced plane candidate 701 while the position of the sliced plane candidate 701 from W1 to W2 in the W direction, as is illustrated in FIG. 16C, changes according to the shape of the gridified evaluation region 610a. In addition, when the sliced plane candidate 701 displaces to the W direction+side, the sliced plane candidate 703 and the gridified evaluation region 610d corresponding to the evaluation region 604 intersect in the W3 to W4 range (see FIG. 16B), and the cross-section area intersecting the sliced plane candidate 701 changes according to the gridified evaluation region 610d shape as is illustrated in FIG. 16C. When the sliced plane candidate 701 displaces to the W direction+side, as is illustrated in FIG. 16B, the sliced plane candidate 701 and the gridified evaluation region 610c corresponding to the evaluation region 603 intersect in the W5 to W7 range, the sliced plane candidate 701 and the gridified evaluation region 610b corresponding to the evaluation region 602 intersect in the W6 to W8 range, and the cross-sectional areas for the gridified evaluation regions 610c and 610b intersecting with the sliced plane candidate 701 change as is in FIG. 16C. Thus, the amount of displacement of the sliced plane candidate 701 necessary to inspect the gridified evaluation regions 610a, 610b, 610c, 610c will be (W2-W1)+(W4-W3)+(W8-W5).

Figure 17A:
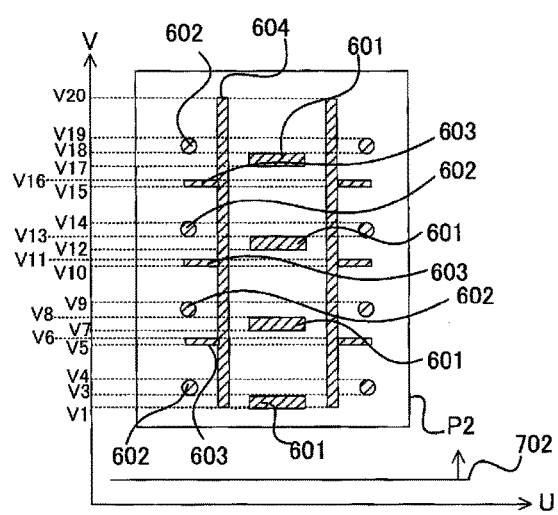
FIGS. 17A and 17B are figures schematically illustrating the processing at the time of cluster analysis.
Figure 17B:
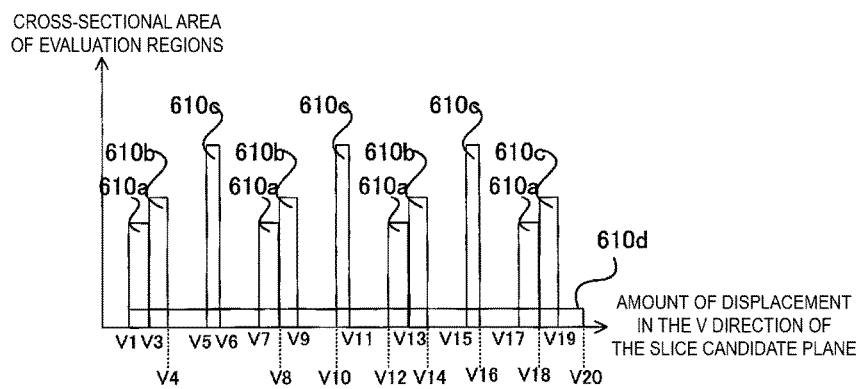

Next, in FIGS. 17A and 17B, a change in the cross-sectional area in which the gridified evaluation regions 610a, 610b, 610c, 610c each corresponding to the evaluation regions 601, 602, 603, 604 and the sliced plane candidate 702 intersect accompanying the displacement of the sliced plane candidate 702 when the sliced plane candidate 702, which is parallel to the WU plane, is displaced in the U direction. In this case, as is illustrated in FIG. 17B, the gridified evaluation region 604 corresponding to the evaluation region 604 continues to intersect with the sliced plane candidate 702 while the sliced plane candidate 702 displaces from V1 to V20. Thus, the amount of displacement of the sliced plane candidate 702 necessary to inspect the gridified evaluation regions 610a, 610b, 610c, 610c will be (V20-V1).

Figure 18A:
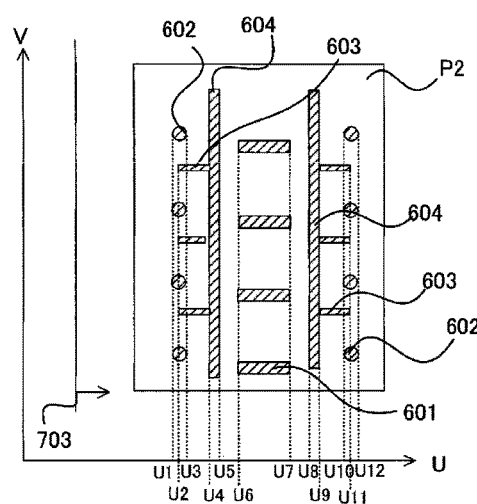
FIGS. 18A and 18B are figures schematically illustrating the processing at the time of cluster analysis.
Figure 18B:
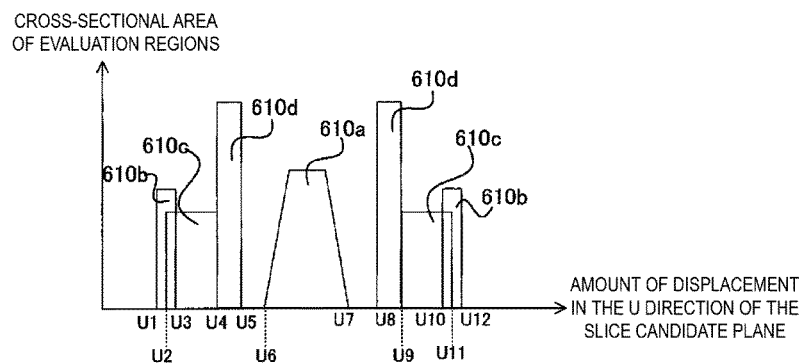

Next, in FIGS. 18A and 18B, a change in the cross-sectional area in which the gridified evaluation regions 610a, 610b, 610c, 610c each corresponding to the evaluation regions 601, 602, 603, 604 and the sliced plane candidate 703 intersect accompanying the displacement of the sliced plane candidate 703 when the sliced plane candidate 703, which is parallel to the VW plane, is displaced in the U direction. In this case, as is illustrated in FIG. 18B, the sliced plane candidate 703 intersects with any of the gridified evaluation regions 610b, 610c, 610d each corresponding to the evaluation regions 602, 603, 604 while the sliced plane candidate 703 displaces from U1 to U5. The sliced plane candidate 703 intersects with the gridified evaluation region 610a corresponding to the evaluation region 601 while the sliced plane candidate 703 displaces from U6 to U7. The sliced plane candidate 703 one again intersects with any of the gridified evaluation regions 610b, 610c, 610d each corresponding to the evaluation regions 602, 603, 604 while the sliced plane candidate 703 displaces from U8 to U12. Thus, the amount of displacement of the sliced plane candidate 703 necessary to inspect the gridified evaluation regions 610a, 610b, 610c, 610c will be (U5-U1)+(U7-U6)+(U12-U8).

The grouping unit 565 and the sliced plane selection unit 563 simulate how to group each of the gridified evaluation regions 610a, 610b, 610c, 610c and select the sliced plane to be able to reduce the amount of displacement based on the results described above, and group the gridified evaluation region 610, which has the smallest amount of displacement, and select a sliced plane that applies to each group. In this case, the grouping unit 565 and the sliced plane selection unit 563 group the gridified evaluation regions 610a, 610b, 610c each corresponding to the evaluation regions 601, 602, 603 into a first group G1, and the gridified evaluation region 610d corresponding to the evaluation region 604 into a second group G2, select the sliced plane candidate 702 as the first sliced plane 712 for the first group G1, and select the sliced plane candidate 701 as the second sliced plane 711 for the second group G2. The sliced range of the first group G1 is selected for 720a, 720b, 720c as is illustrated in FIG. 14B, and the sliced range of the second group G2 is selected for 720e as is illustrated in FIG. 14D.

Note that a case will be described wherein, as a result of the cluster analysis, two or more group divisions are candidates. That is, it is a case where as a result of grouping and calculating the total of each of the amounts of displacement, a similar amount of displacement is obtained in both groupings. In such a case, the grouping to be selected is decided by determining by adding together the cross-sectional area and the amount of displacement for the evaluation region. For example, in FIG. 16C, the total surface area of the regions illustrated as portions corresponding to the evaluation regions 601, 602, 603, 604 are obtained by each of both groupings, and the grouping with the smaller total surface area is selected. This leads to the selection of the grouping with less inspection data, which leads to a reduction in the processing burden of the inspection data.

(6) A Case where Evaluation Regions are Grouped According to the Magnification of the Transmission Image The placement stage 30 of the x-ray inspection apparatus 100 moves in the X direction, the Y direction, and the Z direction, in addition to rotation turning on the rotation axis Yr via the manipulator unit 36. The closer the placement stage 30 moved to the Z direction—side, that is toward the x-ray source 2, the more the magnification of the transmission image of the specimen S increases. Furthermore, by moving the placement stage 30 in the X direction, position matching is performed to fit the desired place on the specimen S into the irradiation range of the x-rays.

First, the procedures for position matching when performing an inspection on the set evaluation region 600 will be described.

Figure 9A:
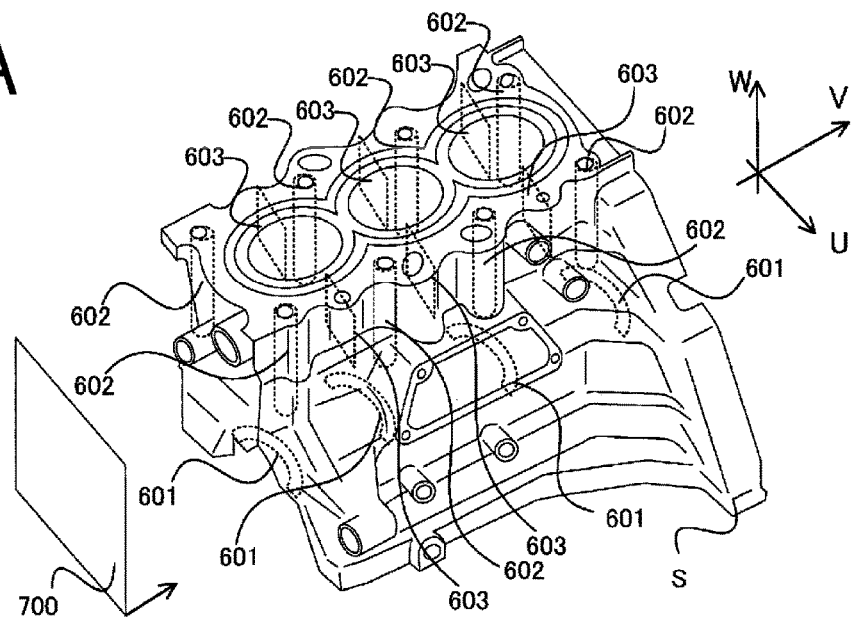
FIGS. 9A and 9B are figures illustrating an example of a sliced plane and a sliced range selected when inspecting a cylinder block for an engine as the specimen.
Figure 19A:
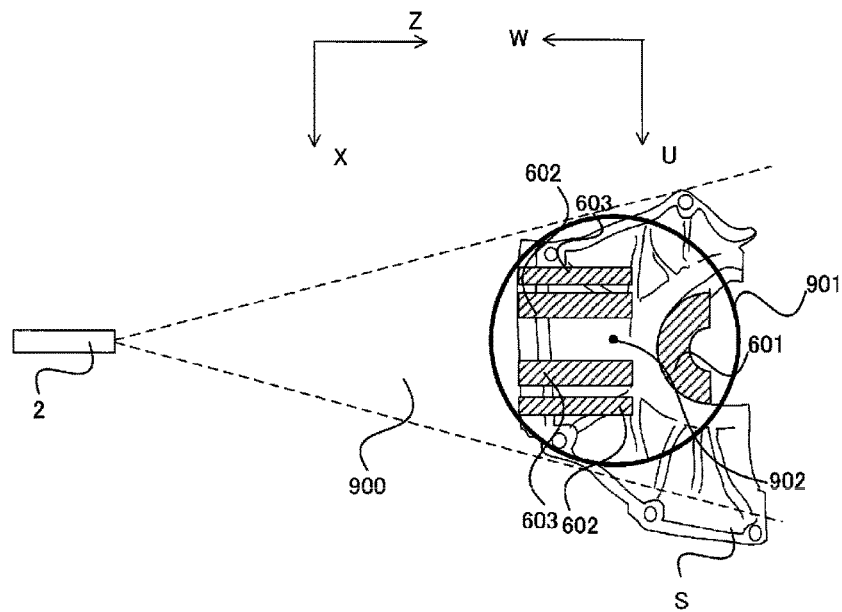
FIGS. 19A and 19B are figures schematically illustrating the position matching of a specimen and a placement table.
Figure 19B:
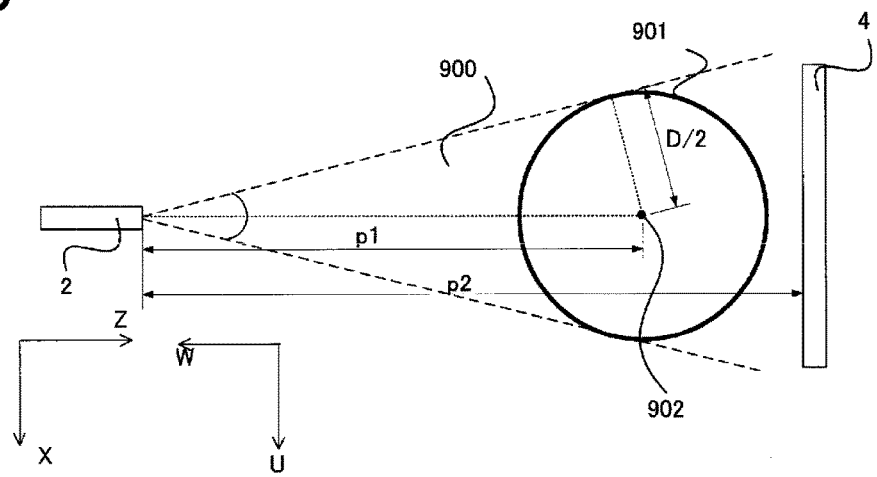

FIG. 19A illustrates a state where the evaluation regions 601, 602, 603 are projected onto the projection plane P2, which is parallel to the WU plane, in a case where a sliced plane 700 displacing in the V direction is selected for the cylinder block of the engine that is the specimen S, as is illustrated in FIG. 9A. In FIGS. 19A and 19B, x-rays are radiated by an x-ray source 2 in an irradiation range 900 on a plane parallel to the XZ plane. When performing an inspection, the V direction of the specimen S is placed so that it matches the Y direction of the x-ray inspection apparatus 100. That is, the rotation axis Yr of the placement stage and the V direction of the specimen S are made to match. As a result, the projection plane P2, which is parallel to the WU plane, is parallel to the placement stage 30, which is parallel to the XZ plane, and the sliced plane 700 displaces in the Y direction in a state parallel to the XZ plane. The position of the placement stage 30 in the X direction and the Z direction is set so that all of the evaluation regions 601, 602, 603 projected on the projection plane P2 are included in the irradiation range 900 of the x-rays. That is, by fixing the position of the placement stage 30 in the X direction and the Z direction during inspection though the sliced plane 700, the increase in inspection time accompanying movement in the X direction or the Z direction can be inhibited.

Here, a circular region 901 including all the evaluation regions 601, 602, 603 inside and a center 902 of the circular region 902 are assumed. The center 902 corresponds to the rotation axis Yr in a case where the specimen S is placed on the placement stage 30, and the evaluation regions 601, 602, 603 inside the circular region 901 are irradiated by x-rays accompanying the rotation of the placement stage 30. Thus, if the position of the placement stage 30 is set in the X direction and the Z direction so that the circular region 901 is included in the irradiation range 900 of the x-rays, inspection can be performed through the sliced plane 700 in a state wherein the position of the placement stage 30 in the XZ directions is fixed.

FIG. 19A illustrates a case where the circular region 901 is set so that the distance between the x-ray source 2 and the center 902 in the irradiation range 900 by x-rays is as small as possible. In this case, inspection of the entire specimen S is no longer possible, but it becomes possible to obtain a transmission image of all the evaluation regions 601, 602, 603 at a high magnification from among the acquirable transmission images. Note that in FIG. 19A it is omitted from the drawing, but it is preferable that the positions of the circular region 901 and the center 902 are decided in the irradiation range 900 by x-rays so that the specimen S and the configuration of the x-ray inspection apparatus 100 do not interfere.

A magnification calculation unit 568 performs processing to position match according to the above procedure. The magnification calculation unit 568 reads coordinates of the set evaluation region 600 out from the data accumulation unit 58, and calculates the coordinates of the center 902 and the diameter or radius of the circular region 901.

A concept for the magnification calculation unit 568 to calculate the position of the center 902 of the circular region 901 will be described using FIG. 19B. The irradiation range 900 by x-rays radiated from the x-ray source 2, that is, the angle θ illustrated in FIG. 19B, is a known value. Thus, the magnification calculation unit 568 calculates a distance p1 from the x-ray source 2 to the center 902 as D/2 sin(θ/2), using the diameter D of the calculated circular region 901, as is illustrated in FIG. 19B. As is described above, when inspecting the specimen S, because the specimen S is placed so that the center 902 and the rotation axis Yr of the placement stage 30 match, the distance p1 from the x-ray source 2 to the center 902 is the distance from the x-ray source 2 to the placement stage 30 on the XZ plane. The magnification calculation unit 568 calculates the magnification of the transmission image using p2/p1, as is publicly known, from the calculated distance p1 and a distance p2 from the x-ray source 2 to the detector 4.

Next, position matching in a case where inspection is performed at different magnifications according to the size of the evaluation region 600 will be described with reference to FIGS. 20A and 20B. In the description below, a case will be illustrated wherein a new evaluation region 605 is set to monitor the occurrence and cause of cavities in the cylinder block of the engine that is the specimen S. Shape grasping for cavities is one method of identifying drawn cavities or gas cavities. It can roughly be discerned that the cavity surface being a ragged shape means a drawn cavity due to constriction, and a smooth shape means a gas cavity, but for this discernment, being able to distinguish as little as 0.1 mm is desirable. For this reason, in the present embodiment, inspection of the evaluation region 600 is performed at a high magnification. Thus, the number of voxels configuring the evaluation region 600 in the inspection results can be increased compared to a case where an inspection of the evaluation region 600 is performed at a low magnification. Thus, by inspecting the evaluation region 600 at a high magnification, shape grasping of the cavities in the evaluation region 600 can be distinguished with high resolving power.

Figure 20A:
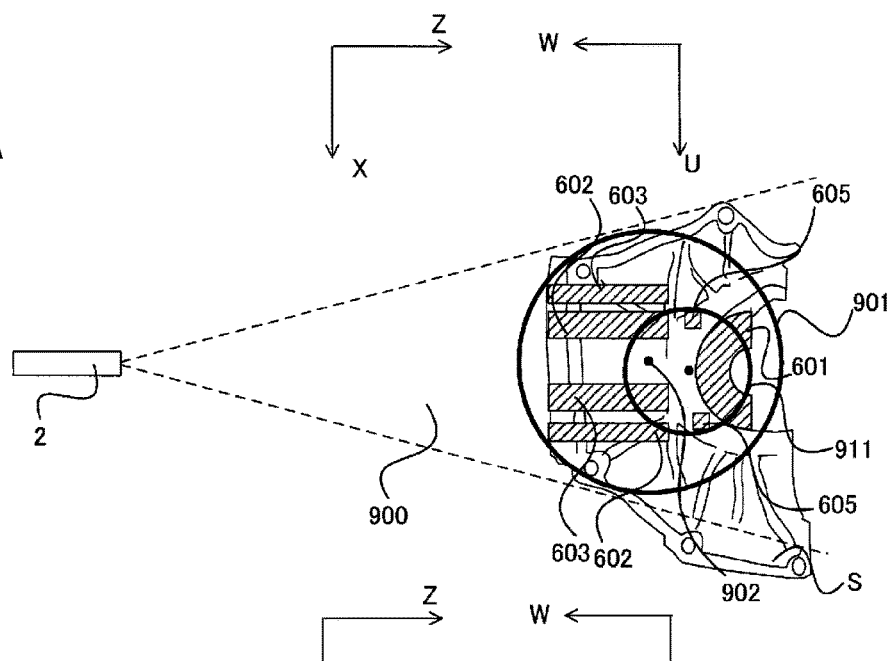
FIGS. 20A and 20B are figures illustrating grouping of evaluation regions according to the ratio of their transmission image.
Figure 20B:
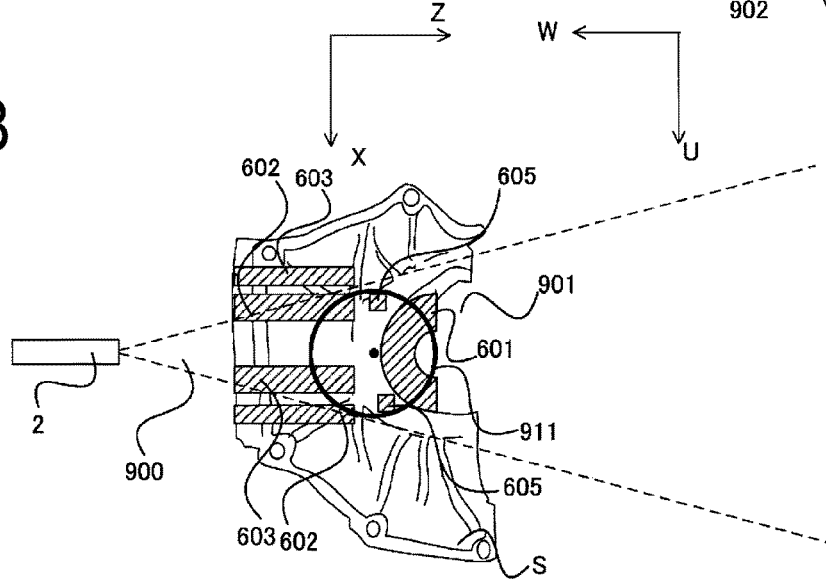

FIG. 20A illustrates a state wherein the evaluation regions 601, 602, 603, 605 are projected on the projection plane P2, which is parallel to the WU plane, for a cylinder block of and engine that is the specimen S, similarly to FIG. 19A. Note that in FIG. 20A as well, the specimen S is placed on the placement stage 30 so that a plane parallel to the WU plane of the specimen S is parallel to the XZ plane. As is described above, the evaluation region 605 is set as a small region. For this reason, when the position of the placement stage 30 in the X direction and the Z direction is decided so that the circular region 901 including the evaluation regions 601, 602, 603, 605 is included in the irradiation range 900 by x-rays, a transmission image of the evaluation region 605 at a high magnification can no longer be obtained.

In such a case, the circular region 901 is set for the evaluation regions 601, 602, 603 similarly to the case in FIG. 19A, and a circular region 911 including the evaluation region 605 is set for the evaluation region 605. That is, a circular region 911 that is smaller than the circular region 901 is set. Then, the position of the placement stage 30 in the X direction and the Z direction is decided so that the circular region 911 is included in the irradiation range 900 by x-rays. Thus, as is illustrated in FIG. 20B, the circular region 911 is set on the side closer to the x-ray source 2 than the circular region 901.

When described in particular, the grouping unit 565 determines whether the size on the plane parallel to the XZ plane is greater than a predetermined value for each of a plurality of gridified evaluation regions 610 using coordinate values in the UVW directions. The grouping unit 565 classifies gridified evaluation regions 610 larger than a predetermined value into a third group G3, and classified gridified evaluation regions 610 smaller than a predetermined value into a fourth group G4, based upon the results of the determination. The magnification calculation unit 568 calculates the position of the placement stage 30 and the magnification of the transmission image for each of the third group G3 and the fourth group G4 set by the grouping unit 565.

Note that one configuration in which information acquiring a transmission image at a high magnification is beforehand settable when setting the evaluation region 605 is included in one aspect of the present invention. In this case, the grouping unit 565 should classify the evaluation region 605 having set information into a group that is different from the evaluation regions 601, 602, 603.

(7) A Case Based on Simulation Results

Figure 21A:
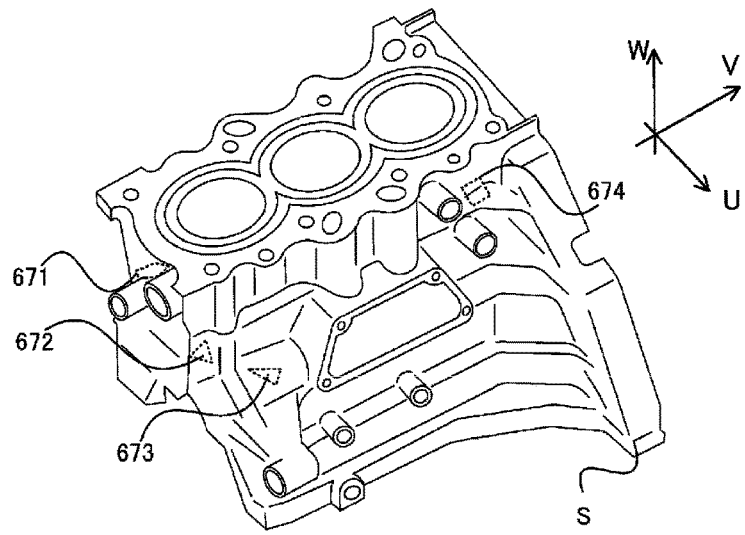
FIGS. 21A and 21B illustrate a sliced plane and a sliced range selected when inspecting a cylinder block based on the results of a simulation.
Figure 21B:
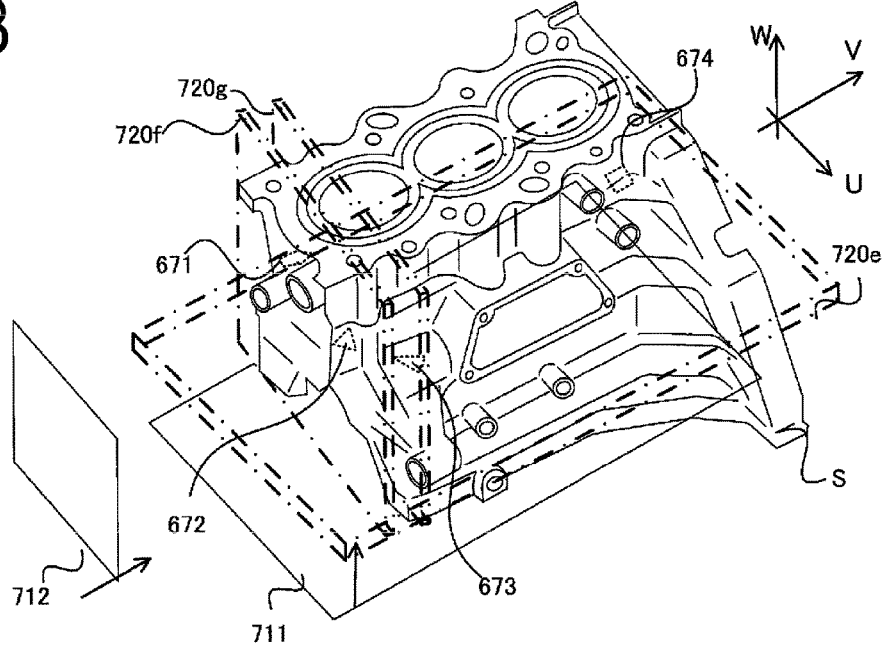

One example of regions 671 through 674 wherein occurrence of a drawn cavity is predicted (hereinafter called predicted occurrence regions) in a case where a cylinder block of an engine is used as the specimen S is illustrated in FIGS. 21A and 21B. The crankshaft journal, cast pull pin, liner, cooling channel, and the like, which are handled as sites that are functionally important to manage, are the evaluation region 600, which is a geometric shape with directions and places set in a design. Conversely, the predicted occurrence regions 671 through 674 derived in a simulation have irregular shapes in three-dimensional space, and in many cases, the predicted occurrence regions 670 do not have planarity or directionality. Note that in FIGS. 21A and 21B, the shape of the predicted occurrence regions 671 through 674 is schematically expressed.

In a case wherein the sliced plane 700 including the evaluation region 600 is decided from predicted occurrence regions 671 through 674 derived in a simulation, the sliced plane selection unit 563 selects the sliced plane 700 as follows. First, the sliced plane selection unit 563 selects the sliced plane 700 decided at the evaluation region 601 for the crankshaft journal, the evaluation region 602 for the cast pull pin, the evaluation region 603 for the liner, the evaluation region 604 for the cooling channel, and the like, which are handled as sites that are functionally important to manage. That is, the sliced plane 700 and the sliced range 720 are selected as is illustrated in FIG. 14B.

Afterwards, the sliced plane selection unit 563 resets the sliced range 720 so that the predicted occurrence regions 671 through 674 are included in a range identical to the sliced range 720 selected as illustrated in FIG. 14B, or in a range stretching the sliced range 720 in a direction orthogonal to the displacement direction of the sliced plane 700. That is, the sliced plane selection unit 563 shares the sliced range 720 by including the predicted occurrence regions 671 through 674 into a sliced range 720 that has already selected, or into a sliced range 720 expanded in a direction wherein the amount of displacement of the sliced plane 700 does not increase, which leads to prevent inspection time from increasing. However, in a case where the sliced range 720 that has already been selected cannot be made to be shared, the sliced plane selection unit 563 newly selects a sliced range 720 using the aforementioned method for predicted occurrence regions.

In FIG. 21B, the reselected or newly selected sliced range 720 and predicted occurrence regions 671 through 674 are illustrated. Note that in FIG. 21B, sliced ranges 720 other than the reselected or newly selected sliced range 720 are omitted for the convenience of drawing.

In the example illustrated in FIGS. 21A and 21B, the predicted occurrence regions 671, 672 are made to share with the sliced range 720*b* illustrated in FIG. 14B, and a new sliced plane 720*f* is reselected, as is illustrated in FIG. 21B. The sliced plane selection unit 563 makes the predicted occurrence region 674 included in the sliced range 720*e* illustrated in FIG. 14B. Because the predicted occurrence region 673 has no selected sliced range 720 that can be shared, the sliced plane selection unit 563 selects a new sliced plane 720*g* including the predicted occurrence region 674.

The evaluation region 600 set as is described above, and the selected sliced plane 700 and the sliced region 720 are stored and saved in the data accumulation unit 58 as three dimensional data from the reference position. In a case where classification is performed by the grouping unit 565, the evaluation region 600 and the group G in which the evaluation region 600 is included are associated and stored and saved in the data accumulation unit 58. Note that the storage place for each of the above described data may be external to the inspection processing device 1, and can be incorporated in three dimensional CAD data, or can be incorporated in three dimensional shape data measured with an x-ray CT device or a three dimensional coordinate measurement instrument.

Figure 22:
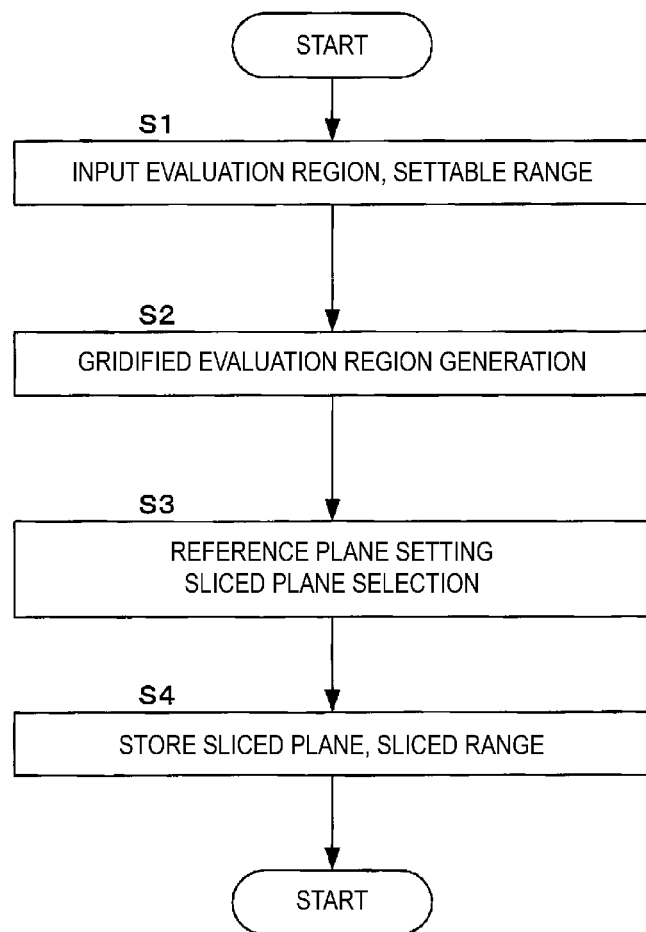
FIG. 22 is a flow chart illustrating the processing performed prior to inspection.
Figure 23:
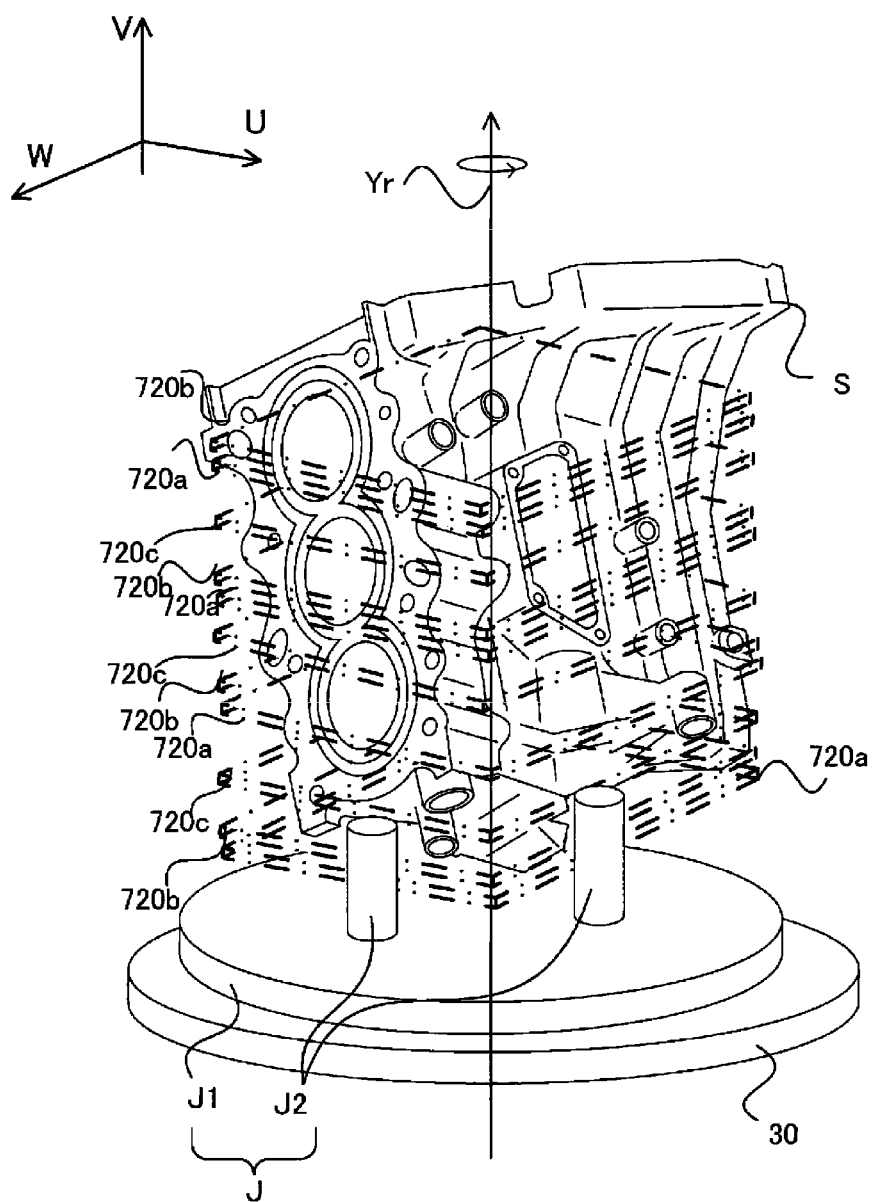
FIG. 23 is a figure illustrating an example of a jig for placement prepared at the time of inspection.

The setting processing for the evaluation region 600 by the inspection control unit 56, the setting processing for information for a lattice grid, and sliced plane and reference plane setting processing will be described with reference to the flowchart in FIG. 22. A program to execute each processing illustrated in the flowchart in FIGS. 19A and 19B is stored beforehand in memory (not shown in the drawing), and is read out and executed by the inspection control unit 56.

In step S1, the evaluation region setting unit 561 sets the position and range of the evaluation region 600 based on information input manually by an operator based on design information from three dimensional CAD or the like, information from simulation results, information based on measurement data performed in the past, and the like; sets a settable range R in a case where the evaluation region 600 has a settable range R, and stores the coordinate values in the data accumulation unit 58, and the flow proceeds to step S2.

In step S2, the lattice grid setting unit 562 divides the evaluation region 600 by lattice grid 650, as is described above and generates gridified evaluation regions 610, and the flow proceeds to step S3. In step S3, the sliced plane selection unit 563 sets a plane to be a reference when partially scanning the specimen S (reference plane). Then, the sliced plane selection unit 563 selects a sliced plane 700 displacing in the shortest direction of the gridified evaluation regions 610 from among the XYZ directions for the gridified evaluation regions 610 of the specimen S, selects a sliced range 720 that will be inspected through the sliced plane 700, and the flow proceeds to step S4. Note that in step S3, grouping of the gridified evaluation regions 610 is performed by the grouping unit 565 according to the shape, distribution direction, and the like of the plurality of distributed gridified evaluation regions 610. In step S4, the selected sliced plane 700 and sliced range 720 are stored in the data accumulation unit 58 as three dimensional data from the reference plane, and the processing ends. Note that in a case where grouping is performed in step S3, the evaluation region 600 and the group G in which the evaluation region 600 is included are associated and stored.

2.4. X-Ray CT Inspection Processing

An inspection unit 564 causes the x-ray inspection device 100 to perform a partial scan on the specimen S in the slice range 720 via the sliced plane 700 selected by a sliced plane and reference plane selection processing. During the x-ray CT inspection, a range containing the evaluation region 600 is inspected, and position matching is performed by inspecting a range containing a reference plane.

Note that because the inspection error of the range containing the reference plane is directly connected to the position error of the evaluation region 600, the inspection may be performed in increased resolution, for example, by increasing the number of data acquired Nr for one rotation of the CT, so as to reduce the reference plane calculation error in the range containing the reference plane.

Note that the means for measuring the reference plane is not limited to the x-ray device. For example, when setting the reference plane based on surface information of the specimen S, measurement results from a non-contact measurement means or a contact-type measurement means may be used. A non-contact measurement means may be a light-cutting measurement method that utilizes line light. A contact measurement means may use a touch probe.

A description of the procedure of inspection preparation and inspection processing is given below.

(1) Inspection Preparation

Prior to starting inspection, the inspection unit 564 controls a manipulator unit 36 via the movement control unit 52 to move the mounting stage 30, and positions the center of the mounting stage 30 at the position p2 calculated by the magnification calculation unit 568. The inspection unit 564 causes the display monitor 6 to perform displaying for placing the specimen S on the mounting stage 30 so that the center 902 calculated by the magnification calculation unit 568 matches the center of the mounting stage 30 that has completed moving, that is, the rotation axis Yr. In this case, the inspection unit 564 causes the display monitor 6 to display the shape image of the specimen S based on design information such as 3-dimensional CAD and the evaluation region 600 superimposed on a background image showing a space on the interior of the housing of the x-ray inspection device 100 and the irradiation range 900 of x-rays irradiated from the x-ray source 2. Alternatively, if the housing ceiling part of the x-ray inspection device 100 is configured such that the vicinity of the mounting stage 30 is imageable via an imaging unit having an imaging element composed of a CCD, CMOS, or the like, display like the following may be performed. The inspection unit 564 causes the display monitor 6 to display an image showing the set evaluation region 600 and an image of the circular region 901 and the center 902 calculated by the magnification calculation unit 568, superimposed on an image of the specimen S acquired by imaging the plane on the positive side of the Y direction of the specimen S placed on the mounting stage 30 via an imaging unit. That is, an image corresponding to FIG. 19A is displayed on the display monitor 6. In the aforementioned manner, an operator can place the specimen S so that the center 902 matches the center of the mounting stage 30, that is, the rotation axis Yr, while confirming the image displayed on the display monitor 6.

Note that it is desirable to provide a jig for placement so it is possible to reproduce the positioned state for other specimens S to be inspected sequentially. FIGS. 20A and 20B illustrate an example having a plate-shaped member J1 placed on the mounting stage 30 and a frame member J2 formed matching the shape of the specimen S for preventing offset of the position of the specimen S on the mounting stage 30 by supporting the specimen S, as a jig J. Such a jig J is preferably not only prepared matching the shape of the specimen S, but is prepared considering cases wherein the same specimen S is inspected a plurality of times with different placement orientations. The jig J can improve work efficiency of inspection if it is processed and prepared at the step where the placement orientations and position of the specimen S have been determined via information from when the evaluation region 600 was set.

(2) Inspection Processing

First, the case wherein the grouping of the evaluation regions 600 by the grouping unit 565 has not been performed is described.

Figure 9B:
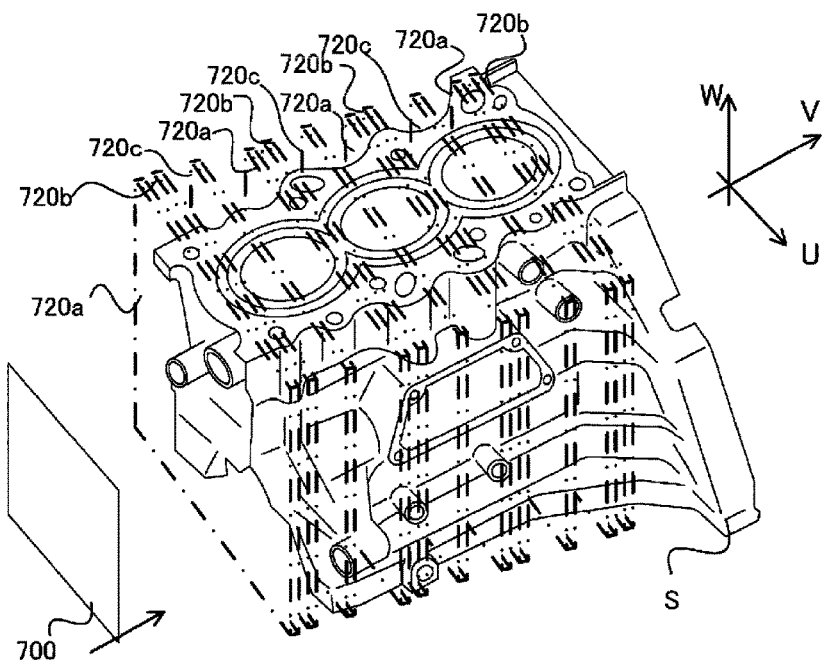
Figure 24:
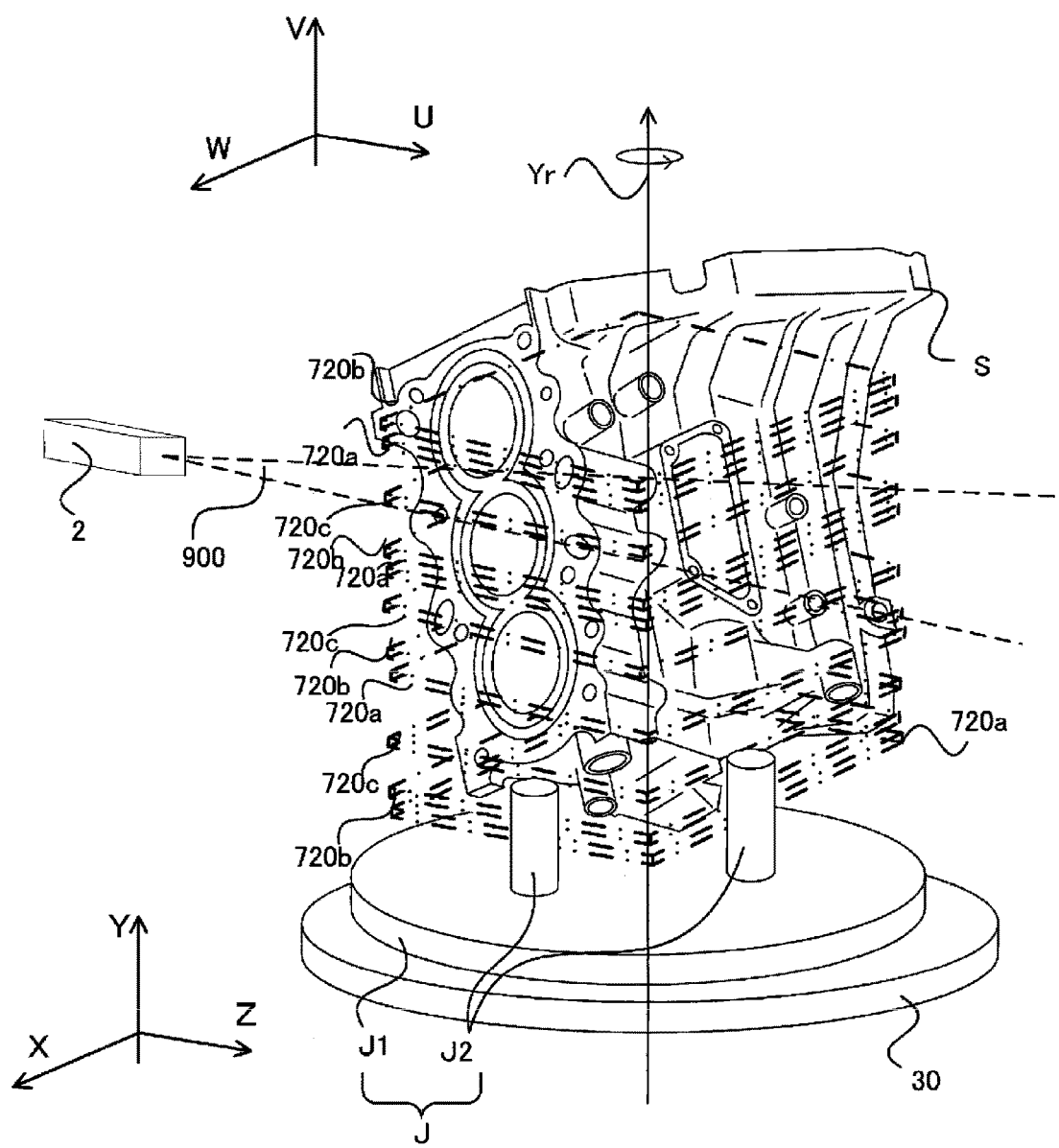
FIG. 24 is a figure illustrating the condition at the time of inspection of the cylinder block for an engine.

FIG. 24 is a figure which illustrates a case wherein an inspection is performed on a specimen S, for which the sliced plane 700 and the sliced range 720 have been selected as illustrated in FIG. 9B. The inspection unit 564 controls the manipulator unit 36 via the movement control unit 52 to rotationally drive and move in the Y direction the mounting stage 30, so that the transmission image for generating a reconstructed image at the sliced ranges 720a, 720b, 720c for inspecting the evaluation regions 601, 602, 603 become obtainable. That is, the inspection unit 564 displaces the sliced plane 700 in the sliced ranges 720a, 720b, 720c according to the movement of the mounting stage 30 in the Y direction.

As illustrated in Form. (1), the amount of displacement of the sliced plane 700 corresponds to the inspection time. The evaluation region 601 of the crankshaft journal unit of the specimen S has a thickness of 2 mm in the Y direction, and four of them are arranged in the Y direction. The evaluation region 602 of the core pin has a thickness of 10 mm in the Y direction, and four of them are arranged in the Y direction. The evaluation region 603 of the liner unit has a thickness of 2 mm in the Y direction, and three of them are arranged in the Y direction. That is, the amount of displacement relative to the evaluation region 601 of the sliced plane 700 is 8 mm (=2 mm×4 arranged), the amount of displacement relative to the evaluation region 602 is 40 mm (=10 mm×4 arranged), and the amount of displacement relative to the evaluation region 603 is 6 mm (=2 mm×3 arranged). Thus, when partially scanning the specimen S, the sliced plane 700 must be displaced a total of 54 mm. As described above, because two minutes of inspection time are needed for every 1 mm, the inspection time for the entire partial scan is 1 hour 48 minutes; compared to the inspection time of 13 hours or so when performing a full scan, the inspection time can be greatly reduced.

The case wherein the grouping of the evaluation regions 600 by the grouping unit 565 has been performed is described next.

Figures 25A, 25B:
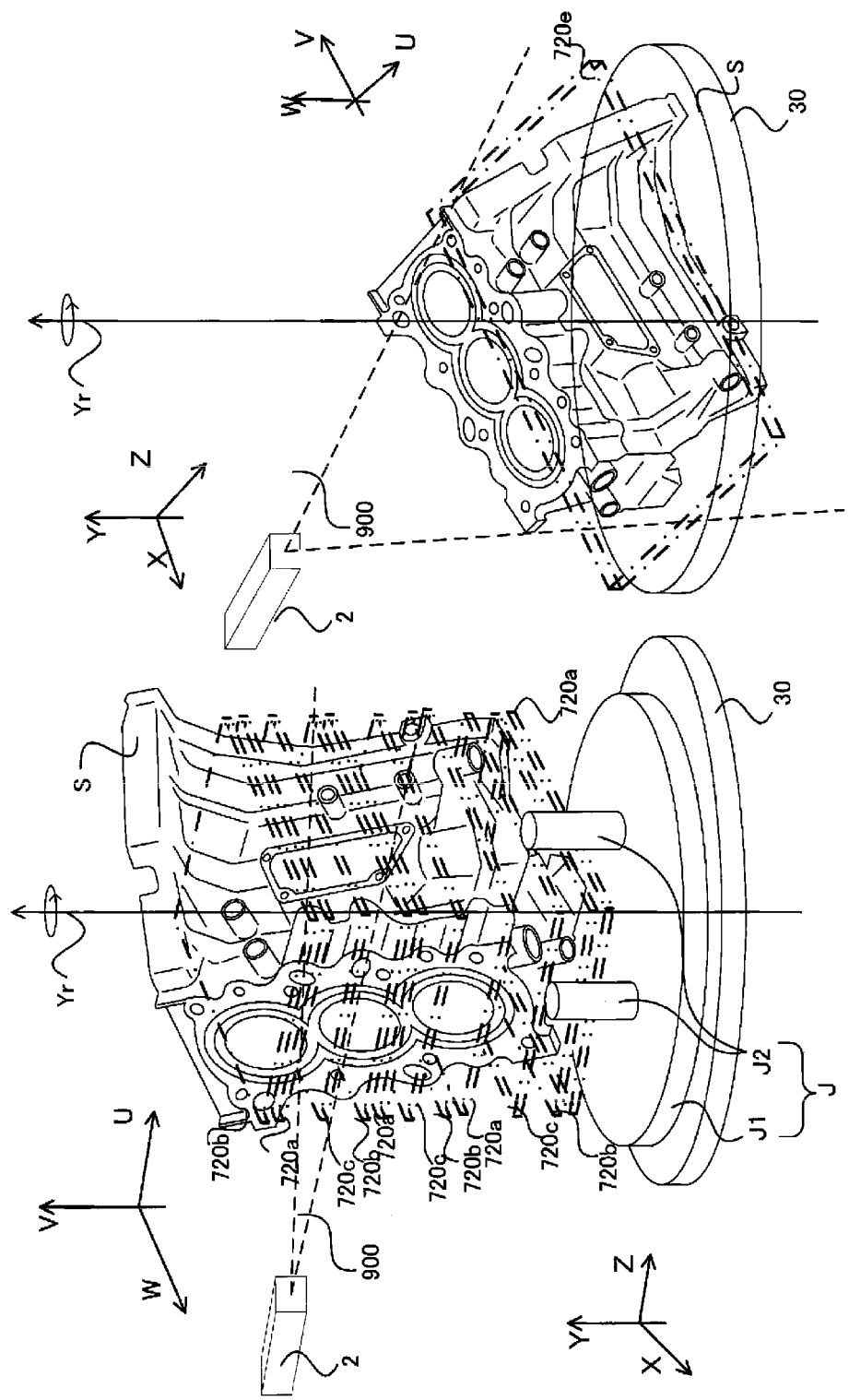
FIGS. 25A and 25B are figures illustrating the condition at the time of inspection of the cylinder block of an engine accompanying changes of the placement orientation.

First, the inspection processing in the case that the evaluation regions 600 have been grouped into a first group G1 and a second group G2 according to the direction that the evaluation regions 600 extend are described next. FIGS. 25A and 25B are drawings illustrating a case wherein a specimen S, for which a first sliced plane 700a, a second sliced plane 700b, and a sliced range 720 have been selected, is inspected, as illustrated in FIG. 14B. FIG. 25A illustrates a case where a partial scan is performed on the evaluation regions 601, 602, 603 which have been grouped into the first group G1, and the inspection is performed in the same manner as in FIG. 24 described above. Thus, when partially scanning the specimen S, the first sliced plane 700a is displaced a total of 54 mm, and an inspection is performed in an inspection time of approximately 1 hour and 48 minutes.

When the inspection of the evaluation regions 601, 602, 603 included in the first group G1 is finished, the placement orientation of the specimen S is changed, as illustrated in FIG. 25B. Changing the placement orientation may be performed via human power by the operator, or may be performed using a manipulator such as a robot arm, which is not pictured. When changing the placement orientation finishes, the inspection unit 564 controls the manipulator unit 36 via the movement control unit 52 to rotationally drive and move in the Y direction the mounting stage 30, so that a transmission image is obtainable in the sliced range 720e for scanning the evaluation region 604 included in the second group G2. That is, the scanning unit 564 displaces the second sliced plane 700b in the sliced range 720d according to the movement of the mounting stage 30 in the Y direction. The evaluation region 604 of the cooling channel of the specimen S has a thickness of 10 mm in the Z direction, and because there is one of them arranged in the Z direction, when the specimen S is partially scanned, the second sliced plane 700b is displaced 10 mm, and the inspection is performed in an inspection time of approximately 20 minutes. If it takes approximately 5 minutes of time to change the placement orientation of the specimen S, the total inspection time is approximately 2 hours and 13 minutes, which reduces greatly the inspection time compared to performing a full scan. When inspecting a plurality of evaluation planes 600 with different extension directions obtained in this manner, the inspection is performed after the placement of the specimen S is changed, and the acquired inspection data for which the position matching is performed is synthesized.

Note that the time needed for changing the placement orientation of the specimen S may be input by the operator. Also, the time needed for changing the orientation of the specimen S of the size, weight, and the like of the specimen S may be estimated, and the time needed for changing the orientation may be calculated. Also, the time needed for changing the orientation may be calculated from the time needed for changing the placement orientation in the past.

Note that in the above description, the inspection by the second sliced plane 700b was performed after the inspection by the first sliced plane 700a, but the inspection by the first sliced plane 700a may be performed after the inspection by the second sliced plane 700b.

As in the case illustrated in FIGS. 12A and 12B, when the evaluation region 601 and the evaluation region 602 having a settable range R are standardized and a sliced range 720d is set, the amount of displacement of the first sliced plane 700a relative to one sliced range 720d becomes 100 mm, which is the thickness in the Y direction of the evaluation region 602 of the core pin. The sliced range 720d is selected at four locations, and totals 40 mm. As described above, the total thickness in the Y direction of the evaluation region 603 is 6 mm; thus, when the specimen S is partially scanned, the first sliced plane 700a is displaced in total 46 mm, and an inspection is performed in an inspection time of approximately 1 hour and 32 minutes. Thus, totaling the time needed for changing the placement orientation of the sample S (approximately 5 minutes) and inspecting the second sliced plane 700b (approximately 20 minutes), the inspection can be finished in approximately 1 hour and 57 minutes.

The inspection processing in the case that the evaluation regions 600 are grouped into a third group G3 and a fourth group G4 according to the magnification of the transmission image is described next.

In this case, a partial scan is performed on the evaluation regions 601, 602, 603 grouped into the third group G3, as illustrated in FIG. 20A described above. When the inspection of the third group G3 finishes, the inspection unit 564 controls the manipulator unit 36 via the movement control unit 54 and moves the mounting stage 30. The mounting stage 30 is moved so that the circular region 911 containing the evaluation region 605 grouped into the fourth group G4 is contained in the irradiation range 900 of the x-ray. Thus, as illustrated in FIG. 20B, because the inspection for the evaluation region 605 is performed on the side closer to the x-ray source 2 than the evaluation regions 601, 602, 603 grouped into the third group G3, a high-magnification transmission image can be obtained. That is, though some time is needed for movement of the mounting stage 30, highly detailed shape information about cavities of specific parts can be obtained, and it can be used for the purpose determining from the shape of the cavity whether it is a shrinkage cavity or a gas cavity.

Note that in the above description, an inspection was performed from the evaluation region 600 grouped into the third group G3, but the inspection may be performed from the evaluation region 600 grouped into the fourth group G4.

The case in which the evaluation regions 600 are grouped into the first to the fourth regions according to the difference in extension direction of the evaluation regions 600 and the magnification of the transmission image will be described.

In this case, the inspection unit 564 executes a partial scan by either a first style or a second style below. As for whether the inspection is performed in the first style or the second style, it is configured to be able to be set by an operator. Note that the x-ray inspection device 100 performing measurement by one style of either the first style or the second style is included as one aspect of the present invention.

—First Style—

In the first style, an inspection is performed such that grouped results are given priority according to the extension direction of the evaluation regions 600. The inspection unit 564 performs an inspection on the evaluation regions 600 that belong in the third group G3, from among the evaluation regions 600 of the first group G1. When the inspection of the evaluation regions 600 of the third group G3 finish, the inspection unit 564 controls the manipulator unit 36 via the movement control unit 54 and moves the mounting stage 30, and performs an inspection of the evaluation regions 600 of the fourth group G4. That is, an inspection is performed by the first sliced plane 700a on the evaluation regions 600 of the third group G3 and the evaluation regions 600 of the fourth group G4.

Afterward, the placement orientation of the specimen S is changed, and the inspection unit 564 performs an inspection of the evaluation regions 600 that belong to the fourth group G4, from among the evaluation regions 600 of the second group G2. When the inspection of the evaluation regions 600 of the fourth group G4 finish, the inspection unit 564 controls the manipulator unit 36 via the movement control unit 54 and moves the mounting stage 30, and performs an inspection of the evaluation regions 600 of the third group G3. That is, an inspection is performed by the second sliced plane 700b on the evaluation regions 600 of the third group G3 and the evaluation regions 600 of the fourth group G4.

—Second Style—

In the second style, an inspection is performed such that grouped results are given priority according to the magnification of the transmission image. The inspection unit 564 performs an inspection on the evaluation regions 600 that belong in the first group G1, from among the evaluation regions 600 of the third group G3. When the inspection of the evaluation regions 600 of the first group G1 finish, and after the placement orientation of the specimen S is changed, the inspection unit 564 performs an inspection of the evaluation regions 600 of the second group G2. That is, the inspection unit 564 causes an inspection to be performed by the first sliced plane 700a and the second sliced plane 700b on the evaluation regions 600 contained in the circular region 901.

Afterward, the inspection unit 564 controls the manipulator unit 36 via the movement control unit 54 and moves the mounting stage 30, and performs an inspection of the evaluation regions 600 contained in the circular region 911. The inspection unit 564 performs an inspection on the evaluation regions 600 that belong in the second group G2, from among the evaluation regions 600 of the fourth group G4. When the inspection of the evaluation regions 600 of the second group G2 finish, and after the placement orientation of the specimen S is changed, the inspection unit 564 performs an inspection of the evaluation regions 600 of the first group G1. That is, the inspection unit 564 causes an inspection to be performed by the first sliced plane 700a and the second sliced plane 700b on the evaluation regions 600 contained in the circular region 911.

Note that the evaluation regions 600 of the fourth group G4 are set to have the objective of inspecting small cavities, as described above. Letting the possibility be low that the shape of the cavities will tend toward a predetermined direction, the inspection unit 564 may cause the evaluation regions 600 of the fourth group G4 to be inspected by one of either the first sliced plane 700a or the second sliced plane 700b.

Figure 26:
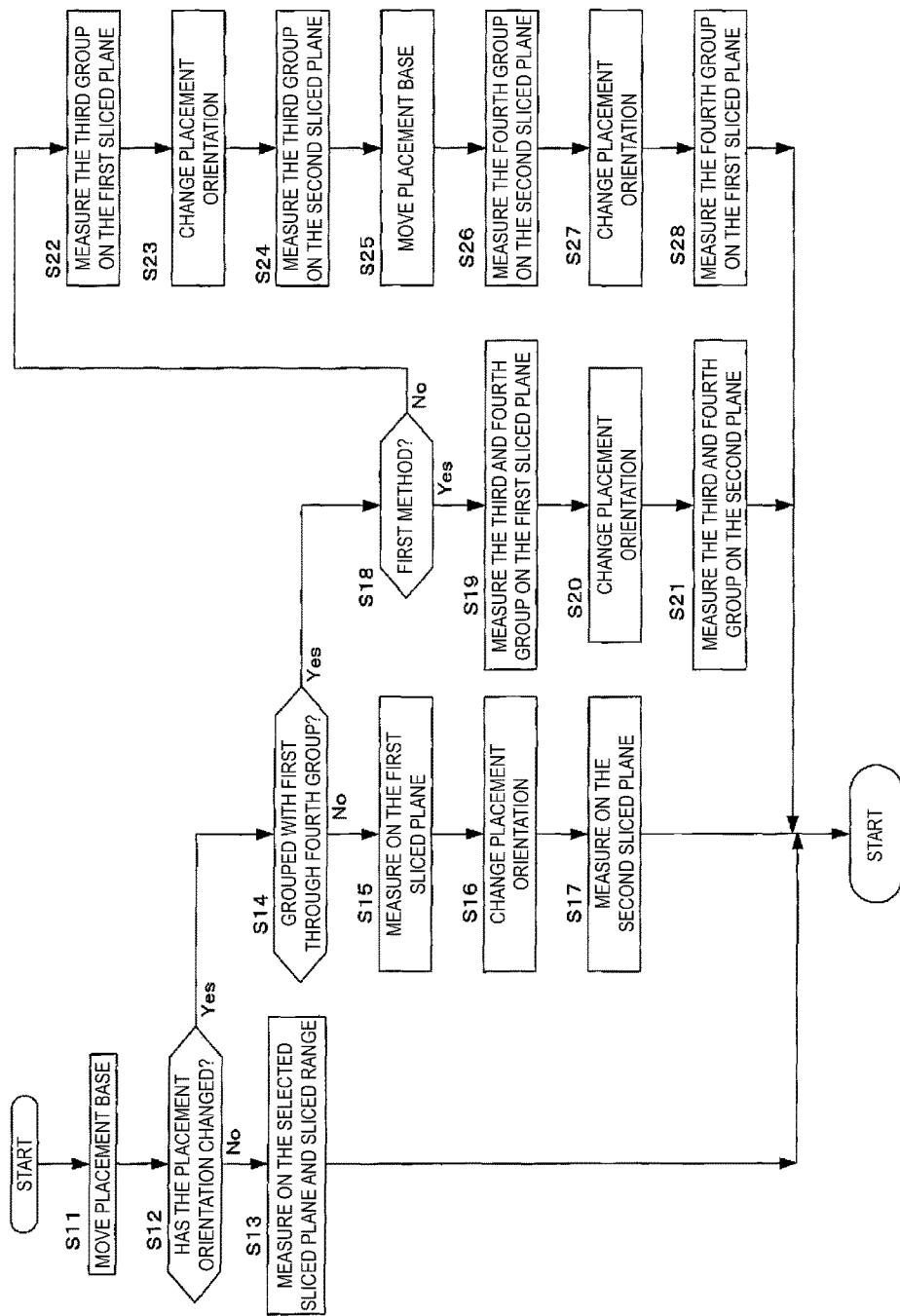
FIG. 26 is a flowchart illustrating the behavior in inspection processing.

The x-ray CT inspection processing of the evaluation regions 600 by the inspection control unit 56 is described with reference to the flowchart of FIG. 26. The program for executing each processing illustrated in the flowchart of FIG. 26 is stored beforehand in memory (not illustrated), is read and executed by the inspection control unit 56.

At step S11, the inspection unit 564 controls the manipulator unit 36 via the movement control unit 52, moves the mounting stage 30 to a predetermined inspection position; the flow then proceeds to step S12. At step S12, it is determined whether there is a change in the placement orientation of the specimen S during inspection. When there is a change in the placement orientation, that is, when a plurality of sliced planes 700 with different directions of displacement are selected by the sliced plane selection unit 563, an affirmative determination is made at step S12; the flow then proceeds to step S14. When there is no change in the placement orientation, that is, when a sliced plane 700 with one direction of displacement is selected by the sliced plane selection unit 563, a negative determination is made at step S12; the flow then proceeds to step S13. At step S13, the manipulator unit 36 is controlled via the x-ray source 2 and the movement control unit 52 to inspect the specimen S on the selected sliced plane 700 and in the sliced range 720; the processing then ends.

At step S14, it is determined whether the gridified evaluation region 610 is grouped into the first to fourth groups G1, G2, G3, G4. In the case that it is grouped into the first to fourth groups G1, G2, G3, G4, an affirmative determination is made at step S14; the flow then proceeds to step 18, described hereinafter. When it is grouped into the first group G1 and the second group G2, a negative determination is made at step S14; the flow then proceeds to step S15. At step S15, the manipulator unit 36 is controlled via the x-ray source 2 and the movement control unit 52, the specimen S is inspected at the selected first sliced plane 711; the flow then proceeds to step S16.

At step S16, it is on standby until the work of changing the placement orientation of the specimen S finishes; then, the flow proceeds to step S17. At step S17, the manipulator unit 36 is controlled via the x-ray source 2 and the movement control unit 52, the specimen S is inspected at the selected second sliced plane 712; the processing then ends.

At step S18, it is determined whether the inspection according to the first style is set. In the case that the inspection is performed according to the first style, an affirmative determination is made at step S18; the flow then proceeds to step S19. At step S19, the manipulator unit 36 is controlled via the x-ray source 2 and the movement control unit 52, the specimen S is inspected at the selected first sliced plane 711 in the evaluation regions 600 of the third group G3. Afterward, the manipulator unit 36 is controlled via the movement control unit 52 and the mounting stage 30 is moved in the Z direction; then, the manipulator unit 36 is controlled via the x-ray source 2 and the movement control unit 52, the specimen S is inspected at the selected first sliced plane 711 in the evaluation regions 600 of the fourth group G4; then, it proceeds to step S20.

At step S20, in the same manner as in step S16, it is on standby until the work of changing the placement orientation of the specimen S finishes; then, the flow proceeds to step S21. At step S21, the manipulator unit 36 is controlled via the x-ray source 2 and the movement control unit 52, the specimen S is inspected at the selected second sliced plane 712 in the evaluation regions 600 of the fourth group G4. Afterward, the manipulator unit 36 is controlled via the movement control unit 52 and the mounting stage 30 is moved in the Z direction; then, the manipulator unit 36 is controlled via the x-ray source 2 and the movement control unit 52, the specimen S is inspected at the selected second sliced plane 712 in the evaluation regions 600 of the third group G3; then, processing is finished.

When the first style is not set, a negative determination is made at step S18; the flow then proceeds to step S22. At step S22, the manipulator unit 36 is controlled via the x-ray source 2 and the movement control unit 52, the specimen S is inspected at the selected first sliced plane 711 in the evaluation regions 600 of the third group G3, and the flow proceeds to step S23. At step S23, it is on standby until the work of changing the placement orientation of the specimen S finishes; then, the flow proceeds to step S24. At step S24, the specimen S is inspected at the selected second sliced plane 712 in the evaluation regions 600 of the third group G3; then, the flow proceeds to step S25.

At step S25, the manipulator unit 36 is controlled via the movement control unit 52 and the placement platform 30 is moved in the Z direction; then, the flow proceeds to step S26. At step S27, the manipulator unit 36 is controlled via the x-ray source 2 and the movement control unit 52, the specimen S is inspected at the selected second sliced plane 712 in the evaluation regions 600 of the fourth group G4, and the flow proceeds to step S27. At step S27, it is on standby until the work of changing the placement orientation of the specimen S finishes; then, the flow proceeds to step S28. At step S24, the specimen S is inspected at the first sliced plane 711 in the evaluation regions 600 of the fourth group G4; then, processing is finished.

Processing relating to the reconstructed image generated based on the transmission image obtained by the inspection of the specimen S is described next. As for processing relating to the reconstructed image, artifact removal processing and evaluation region update processing is performed. Each processing is described below.

—Artifact Removal Processing—

The image processing unit 59 performs artifact removal processing on the reconstructed image of the specimen S obtained from a full scan or a partial scan as described above.

For reconstructed images obtained by performing x-ray CT inspection processing on a thick specimen S made of a low-density material or a specimen S composed of a composite material, artifacts (images generated in two dimensions that are not an actual substance) are generated due to differences of transmission energy density when x-rays are transmitted through the specimen S. These artifacts have a large impact on generation of artificial defects and inspection errors of boundary planes during inspection and inspection processing. The image processing unit 59 removes artifacts generated in the reconstructed image via image processing.

Figure 27A:
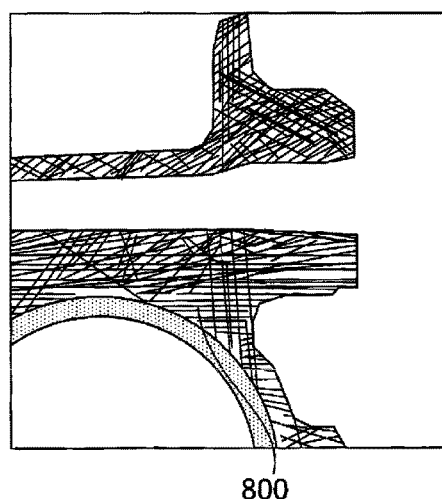
FIGS. 27A to 27D are figures schematically illustrating an example of an artifact and artifact removal processing.
Figure 27C:
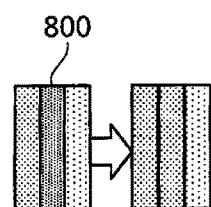
Figure 27B:
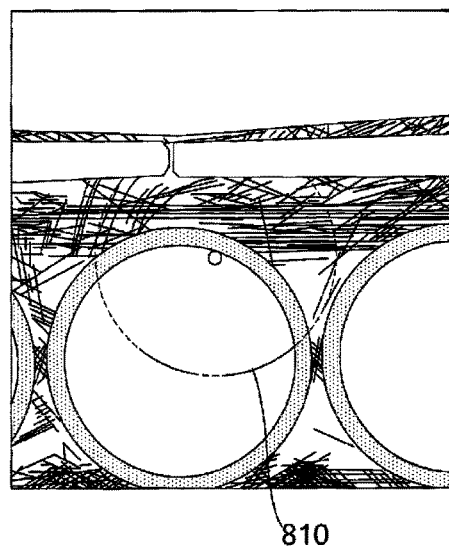

FIGS. 27A to 27D illustrate a streak artifact, which is line-shaped and is a noise factor generated frequently (see FIG. 27A) and a ring artifact, which is ring-shaped (see FIG. 27B). The image processing unit 59 reduces noise elements by filling these two types of artifacts with the average value of the brightness of the surrounding area, using the characteristics of their shapes. This can greatly reduce the image editing operation needed before analysis, which is described hereinafter. As for the removal method for streak artifacts illustrated in FIG. 27A, the image processing unit 59 uses the characteristic that the artifact is line-shaped to perform image processing. As illustrated in FIG. 27C, the image processing unit 59 extracts a line-shaped region 800 composed of straight line elements from the reconstructed image, finds the average value of the brightness of pixels neighboring on both sides in the direction of the line width for each line-shaped region 800 of the extracted straight line elements, and applies and replaces the pixel of the extracted line-shaped region 800 with that brightness value. In FIG. 27C, for convenience in illustration, it is shown such that the lower the brightness value of the line-shaped region 800 is, the more densely packed the dots are placed. Note that the threshold value of the boundary conditions of the line-shaped region 800 to be extracted may be set, as they differ for each pixel of the reconstructed image. Also, in reality, the width direction of the line-shaped region 800 is composed of a plurality of pixels.

Figure 27D:
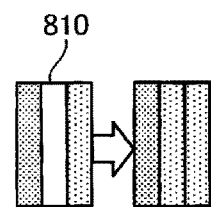

As for the removal method for ring artifacts illustrated in FIG. 27B, the image processing unit 59 uses characteristics in which the artifacts are ring-shaped and are generated by darkness levels, scans in the radial direction from the rotational center, and extracts circular pixel groups where ring-shaped singular points of difference are detected. The image processing unit 59 finds the average value of the brightness of pixels neighboring on both sides in the direction of the diameter of the extracted circular pixel group 810, and applies and replaces the circular pixel group 810 with that brightness value. In FIG. 27D, for convenience in illustration, it is shown such that the lower the brightness value of the circular pixel group 810 is, the more densely packed the dots are placed. Note that the threshold value of the boundary conditions of the roundness and the like to be extracted may be set, as they differ for each image. Also, in reality, the circular pixel group is composed of a plurality of pixels. As described above, because the relationships between the rotation axis Yr of the mounting stage 30 and the placement position of the specimen S are determined, the image processing unit 59 can easily perform identification of the center of the ring artifact by using information relating to the rotation axis Yr relative to the sample S.

By removing artifacts like those described above, the quantitative properties such as volume ratio of cavities per thickness or unit volume can be increased. That is, the precision of the inspection of the thickness and the cavity volume ratio can be increased. When the evaluation regions 600 are narrowed down, the time for data processing of the thickness, cavities, and the like can be reduced. Regarding ring artifacts, when the center of the ring artifact is outside the range of the evaluation region 600, it is desirable to perform data processing for the thickness, cavity, and the like regarding the evaluation regions 600 after performing artifact removal processing in a range containing the center.

Note that the generation of artifacts depends largely on the shape and structure of the specimen in the evaluation region 600, as described above. That is, streak artifacts tend to be generated when the shape or structure of the specimen in the evaluation region 600 is a straight line shape, and ring artifacts tend to be generated when the shape or structure of the specimen in the evaluation region 600 is circular. When setting the evaluation regions 600 for the specimen S, it is desirable to relate information relating to artifact removal image processing suitable for the evaluation regions 600 to the data relating to the evaluation regions 600, so as to carry out removal image processing suitable for removing noise artifacts for the transmission image relating to the evaluation region 600.

As a result of the inspection of the specimen S, shape information of the specimen S is generated with such an artifact removal processing. The generated shape information of the specimen S is determined to be good or bad for each lattice grid unit based on non-defect factor parameters, which are described later; then, the non-defect determination result is displayed at the lattice grid unit. At this time, shape model data (for example, CAD data) of the specimen S or shape data of the specimen S obtained from artifact removal processing may be displayed overlapping the lattice grid. Also, the non-defect level calculation may be performed for each evaluation region instead of lattice grid units, and the results thereof may be performed. In this case, the non-defect level of the evaluation regions 600 can be calculated according to the average value or dispersion value of the non-defect level of the lattice grid set in the evaluation regions 600.

—Evaluation Region Update Processing—

Evaluation region update processing is performed by the inspection analysis unit 57 based on inspection results of the specimen S inspected by a full scan, or on inspection results of the specimen S inspected by a partial scan, in the manner described above. In evaluation region update processing, the shape information generated based on the plurality of transmission images of the specimen S obtained from a full scan or partial scan is analyzed, and based on the history of analysis results, it is determined whether an update for the evaluation regions 600 such as a shape change, position change, deletion, or new addition of the evaluation regions 600 set in the aforementioned manner should be performed. The determined result is displayed on the display monitor 6, and when the update execution of the evaluation regions 600 is permitted by an operator who has checked the determined result, the update of the evaluation regions 600 is performed based on the history of the analysis results. In the present embodiment, updating the evaluation regions 600 means changing the shape (region expansion, region contraction, or region deletion) of the evaluation regions 600 based on inspection results of shape information obtained from a partial scan, or a new addition of the evaluation region 600 based on the inspection result of shape information obtained from a full scan.

As illustrated in FIG. 2, the inspection analysis unit 57 is provided with a lattice gridifying unit 570, a volume ratio analysis unit 571, a thickness analysis unit 572, a non-defect analysis unit 573, a non-defect determination unit 574, a region correction unit 575, a region addition unit 576, a region resetting unit 577, and a display control unit 578. The lattice gridifying unit 570 performs lattice gridifying on a region corresponding to the evaluation region 600, from among the shape information of the specimen S generated from a partial scan, then displays shape information from the same position as the evaluation region 600 overlapped in a gridified evaluation region. Also, the lattice gridifying unit 570 performs position matching for the shape information of the specimen S obtained from the full scan and a lattice grid. In particular, during a partial scan, because shape information for the specimen S is generated only for parts set in the evaluation regions 600, a lattice grid which matches places with the generated shape information is extracted, a measurement of volume ratio and thickness of the lattice grid unit, which is a non-defect inspection parameter, is performed relating to the extracted lattice grid, and non-defect analysis is performed. Because one string of analysis processing is performed relating only to lattice grids on which the evaluation region 600 is set, setting beforehand the evaluation regions 600 can not only reduce the time for scanning, but prevent the analysis processing time from increasing unnecessarily, which is described later.

The volume ratio analysis unit 571 calculates a volume ratio of internal defects such as cavities for each lattice grid 650 on the shape information of the specimen S obtained from a partial scan, and provides a volume ratio non-defect level according to the volume ratio. The volume ratio analysis unit 571 calculates the volume ratio of internal defects such as cavities for each lattice grid 650 relating to all lattice grids 650 in which shape information exists, for shape information of the specimen S obtained from a full scan, and provides a volume ratio non-defect level according to the volume ratio. The thickness analysis unit 572 calculates the thickness of the specimen S for each lattice grid 650 applicable to positions corresponding to the evaluation regions 600, relating to shape information of the specimen S obtained from a partial scan, and provides a thickness defect level according to the thickness. The thickness analysis unit 572 calculates the thickness of the specimen S for each lattice grid 650, relating to all lattice grids 650 in which shape information exists, for shape information of the specimen S obtained from a full scan, and provides a thickness defect level according to the thickness.

The non-defect analysis unit 573 sets the non-defect level, which shows the non-defect of each lattice grid 650, based on the volume ratio calculated by the volume ratio analysis unit 571 and the thickness calculated by the thickness analysis unit 572. When obtaining shape information for a plurality of the specimen S that was manufactured by the same process and has substantially the same shape, the non-defect analysis unit 573 calculates an evaluation indicator relating to the lattice grid 650 according to the history of non-defect levels relating to each lattice grid 650 acquired from the shape information. The non-defect determination unit 574 determines whether a change, deletion, or new addition of an evaluation region 600 is necessary based on the evaluation indicator calculated by the non-defect analysis unit 573. When it is determined by the non-defect determination unit 574 that a change of an evaluation region 600 is necessary, the region correction unit 575 creates corrected evaluation region data for the changed evaluation region 600, and the display control unit 578 displays an image corresponding to the corrected evaluation region data on the display monitor 6.

When it is determined that the new addition of an evaluation region 600 is necessary, the region addition unit 576 creates data for the evaluation region 600 to be added, and the display control unit 578 displays an image corresponding to the data for the additional evaluation region, which is the evaluation region 600 to be added, on the display monitor 6. When an operation of the input operation unit 11 is received from the operator, who has checked the image of the corrected evaluation region or the added evaluation region displayed on the display monitor 6, the region resetting part 577 sets the corrected evaluation region or the added evaluation region as a new evaluation region 600, and stores it in the data accumulation unit 58.

A detailed description is given below.

Figure 28:
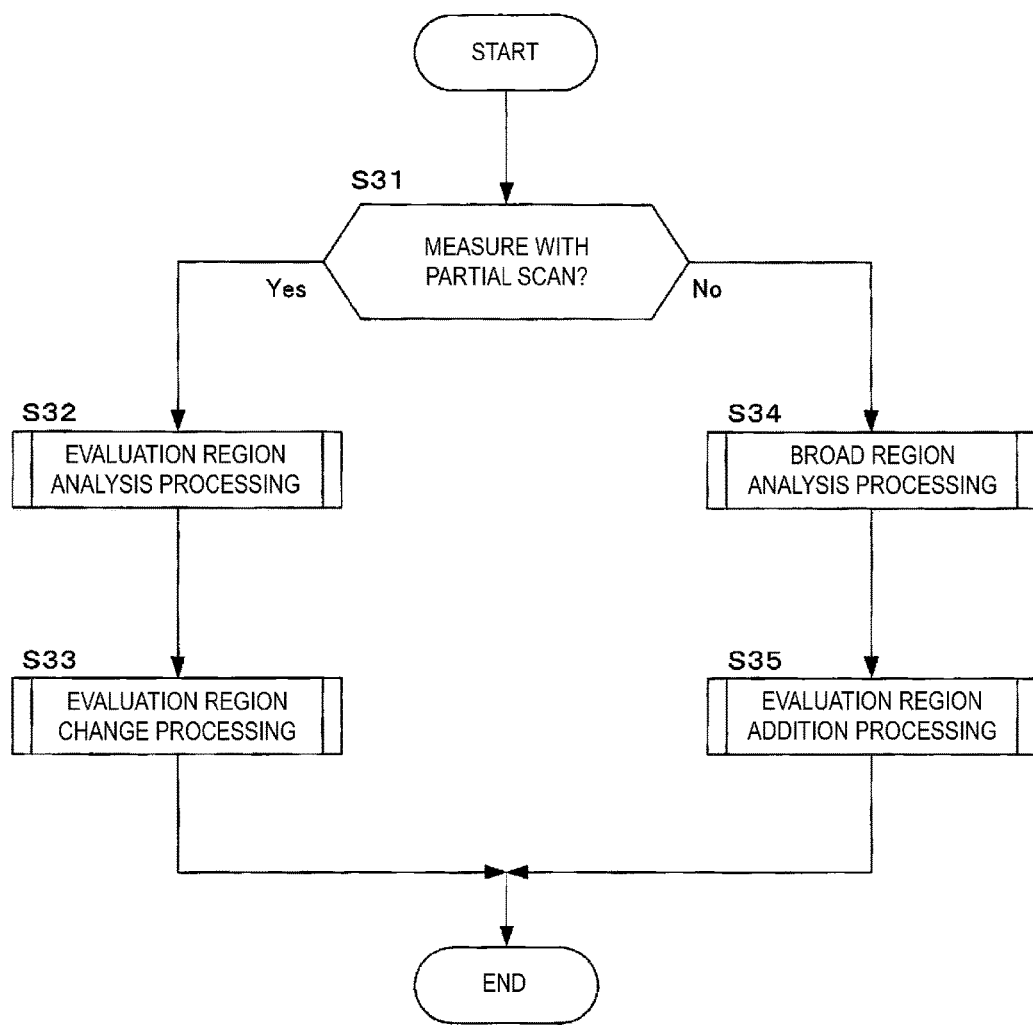
FIG. 28 is a flowchart illustrating the behavior in evaluation region update processing.

The update processing of evaluation regions of the specimen S on which an inspection is performed by the x-ray inspection device 100 using the results from performing successive non-defect determination for specimens S that have been manufactured by the same process and have substantially the same shape is described with reference to the flow chart of FIG. 28, The program for executing each processing illustrated in the flowchart of FIG. 28 is stored beforehand in memory (not illustrated), is read and executed by the inspection analysis unit 57.

At step S31, it is determined whether the obtained shape information of the specimen S has been acquired from a partial scan or from a full scan. In the case of shape information acquired from a partial scan, an affirmative determination is made at step S31; the flow then proceeds to step S32; in the case of shape information acquired from a full scan, a negative determination is made at step S31; the flow then proceeds to step S34. Note that as described above, inspections of the specimen S by shape information acquired from a full scan are performed with a very low frequency. This is because a full scan requires a very long time to obtain a reconstructed image of the entire specimen S. The inspection time for obtaining a reconstructed image is very long compared to the cycle time on a manufacturing line on which the specimen S is manufactured. Thus, most of the inspections of the specimen S are performed via a partial scan. A partial scan may be performed relating to all of the specimens S manufactured in a large quantity, or may be performed for every few (for example, five or ten) from among the specimens S manufactured in a large quantity.

At step S32, the inspection analysis unit 57 performs evaluation region analysis processing relating to the shape information of the specimen S positioned in the evaluation region 600 acquired from a partial scan; the flow then proceeds to step S33. At step S33, the inspection analysis unit 57 performs the evaluation region change processing; the processing then ends. Note that the details of the evaluation region analysis processing and the evaluation region change processing are described hereinafter. At step S34, the inspection analysis unit 57 performs broad region analysis processing on shape information of a broad region (called broad region shape information hereinafter) of the specimen S acquired from a full scan; the flow then proceeds to step S35. At step S35, the evaluation region addition processing is performed; the processing then ends. Note that in the case of a full scan, because shape information is acquired for regions set as an evaluation region, non-defect determination may be performed based on shape information already set on evaluation regions, and the deletion or change processing for the evaluation region may be performed. Details for the broad region analysis processing and evaluation region addition processing are described hereinafter.

In the description below, the description is given divided into evaluation region analysis processing, evaluation region change processing, broad region analysis processing, and evaluation region addition processing.

—Evaluation Region Analysis Processing—

In evaluation region analysis processing, internal defects such as cavities and the thickness are detected from the shape information positioned at the evaluation region 600 of the specimen S obtained from a partial scan and an analysis relating to the non-defectiveness of the specimen S is performed, such as a high possibility of the specimen S being a defective product due to the detected cavities, a possibility of strength insufficiency, a possibility of a leak occurring, and the like. A detailed description is given below.

When performing evaluation region analysis processing, simplification of processing is achieved by performing processing on lattice grid units relating to the shape information of the evaluation region 600. Because of this, the lattice gridifying unit 570 extracts a lattice grid corresponding to the evaluation region 600. Then, shape information of the specimen S corresponding to the extracted lattice grid (called evaluation region shape information hereinafter) is extracted, and each lattice grid and shape information are associated. In this case, the lattice gridifying unit 570 reads the coordinate value of the evaluation region 600 stored on the data accumulation unit 58 and identifies the lattice grid corresponding to the coordinate value of the evaluation region 600. Further, the lattice grid extracts the lattice grid corresponding to the reference plane set on the specimen S. Meanwhile, the shape information of the specimen S includes shape information corresponding to the position of the reference plane, in addition to shape information corresponding to the position of the reference region 600. Further, because the positional relationship of the shape information of both can be grasped, by causing the lattice grid corresponding to the shape information of the reference plane and the position of the reference plane to match, the lattice grid identified on the evaluation region 600 and the shape information of the specimen S in the same position can be made to correspond. In this manner, the lattice grid is identified as a target of analysis processing.

Next, the volume ratio analysis unit 571 detects the existence of cavities in each lattice grid 650 identified in the above manner, and in the case that a cavity is detected, calculates the volume ratio of the cavity in the lattice grid 650. The volume ratio analysis unit 571 uses known methods to recognize the polygon groups other than the polygon groups applicable to the boundary plane with the exterior (outside air) of the specimen S as the boundary plane with the hollow portions of the internal defects of the specimen S from a created polygon surface model, and creates a blowhole model encompassing these polygons. The volume ratio analysis unit 571 finds the volume of cavities for each lattice grid 650 relating to this blowhole model, and calculates the volume ratio by dividing it by the volume of the lattice grid 650.

The lattice grid 650 includes those which partially overlap with the cavity model, and those which entirely overlap with the cavity model. Thus, the volume ratio of cavities is different for each lattice grid 650. The volume ratio analysis unit 571 sets the volume ratio non-defect level, which shows the non-defectiveness according to the volume ratio calculated for each lattice grid 650. In this case, for example, it may be set such that when the volume ratio is 0 percent to 20 percent, the volume ratio non-defect level is 4; when 20 percent to 40 percent, the volume ratio non-defect level is 3; when 40 percent to 60 percent, the volume ratio non-defect level is 2; when 60 percent to 80 percent, the volume ratio non-defect level is 1; and when 80 percent to 100 percent, the volume ratio non-defect level is 0. Note that in this case, it is expressed that as the value of the volume ratio non-defect level declines, the higher the possibility of bringing about a major defect in the specimen S. The set volume ratio non-defect level is related to a coordinate value of the lattice grid 650 and stored in the data accumulation unit 58. Note that concerning the value of the volume ratio non-defect level relating to the volume ratio, configurations which allow setting by the operator are also included in one aspect of the present invention.

The thickness analysis unit 572 calculates the thickness for each lattice grid 650 relating to the gridified evaluation region transmission image. The thickness analysis unit 572 uses known polygon surface models to calculate the thickness based on the distance in the direction of the normal line set from each position of the boundary plane with the hollow portion of an internal defect. The thickness analysis unit 572 sets a thickness non-defect level showing the non-defectiveness according to the degree of difference between the thickness calculated at each lattice grid 650 and shape information of the specimen S that is the ideal model (for example, shape information such as CAD, shape information obtained by the x-ray inspection device 100 of a specimen S determined to be non-defective in the past, and the like). In this case, for example, relating to shape information of the specimen S that is the ideal model, it may be set such that the thickness non-defect level is 0 when the difference in thickness of the obtained specimen S exceeds the allowable tolerance range in the direction of being thin; the thickness non-defect level is 1 when the difference in thickness is within the allowable tolerance range in the direction of being thin, but is at least 80 percent of the allowable tolerance range; and the thickness non-defect level is 2 when the difference in thickness is within the allowable tolerance range in the direction of being thin and is less than 80 percent of the allowed tolerance range. Note that in this case, it is expressed that as the value of the thickness non-defect level declines, the higher the possibility of bringing about a major defect in the specimen S. The set volume ratio non-defect level is related to a coordinate value of the lattice grid 650 and stored in the data accumulation unit 58. Note that concerning the value of the thickness non-defect level relating to the thickness, configurations which allow setting by the operator are also included in one aspect of the present invention.

The non-defect analysis unit 573 sets the non-defect level showing the non-defectiveness of each lattice grid 650 from the volume ratio non-defect level set by the volume ratio analysis unit 571 and the thickness non-defect level set by the thickness analysis unit 572. The non-defect analysis unit 573 sets a non-defect level of 0 to 4 for each lattice grid 650, for example. When the non-defect level is 0, it shows that the possibility of bringing about a defect to the specimen S is very high; when it is 4, the possibility of bringing about a defect to the specimen S is very low.

An example of the non-defect level set from the volume ratio non-defect level and the thickness non-defect level is illustrated in FIG. 29. Note that a configuration which has the relationship illustrated in FIG. 29 able to be set by an operator is included in one aspect of the present invention.

The non-defect analysis unit 573 associates the non-defect level set for each shape information measured from each specimen S with the lattice grid 650, and stores it in the data accumulation unit 58. By performing measurements on a plurality of specimens S, a history of a plurality of non-defect levels is stored for the same lattice grid 650. When the history count reaches or exceeds a predetermined number, that is, when the number of times of the measurements on the specimen S reaches or exceeds a predetermined number of times, the history of the plurality of non-defect levels is used to calculate an evaluation indicator for each lattice grid 650. The non-defect analysis unit 573 calculates, for example, the average or standard deviation of the non-defect level of lattice grids 650 in the same position as an evaluation coefficient. The ratio of change in time of the non-defect level or the like may also be used as the evaluation coefficient. This evaluation coefficient corresponds to each lattice grid 650 and is updated each time it is measured.

When the evaluation coefficient of the lattice grid 650 calculated by the non-defect analysis unit 573 is greater than or equal to a first threshold, or when the evaluation coefficient exceeds a first predetermined range, the non-defect determination unit 574 determines that the region on the specimen S corresponding to that lattice grid 650 has a high possibility of generating a defect on the specimen S. Further, in a case where the evaluation coefficient for the lattice grid 650 calculated by the non-defect analysis unit 573 is less than the second threshold (< the first threshold), or when it is in a second predetermined range (a range such as one where the evaluation coefficient illustrates a higher direction of non-defectiveness compared to the first predetermined range), the non-defect determination unit 574 determines that the probability that the region of the specimen S corresponding to the lattice grid 650 will generate defects is low, and can be deleted from the evaluation region 600. Evaluation region update processing, which is described hereinafter, is performed based on the determination result of the non-defect determination unit 574.

Evaluation region analysis processing of step S32 of FIG. 28 is described with reference to the flowchart of FIG. 30.

At step S40, the lattice gridifying unit 570 sets a lattice grid 650 on the evaluation region 600; the flow then proceeds to step S41. At step S41, in the case of a partial scan, the lattice gridifying unit 570 position matches the shape information of the specimen S created based on the transmission image with the lattice grid, extracts shape information of the specimen S matching the lattice grid position matched on the evaluation region 600; the flow then proceeds to step S42. Also, in the case of a full scan, the lattice gridifying unit 570 simply position matches the shape information of the specimen S with the lattice grid 650. At step S42, the volume ration analysis unit 571 calculates the volume ratio for each extracted lattice grid 650, sets a volume ratio non-defect level; the flow then proceeds to step S43.

At step S43, the thickness analysis unit 572 calculates a thickness for each extracted lattice grid 650, sets a thickness non-defect level; the flow then proceeds to step S44. At step S44, the non-defect analysis unit 573 sets a non-defect level for the lattice grid 650 from the volume ratio non-defect level and the thickness non-defect level set to the same lattice grid 650, stores the following information for each lattice grid 650; the flow then proceeds to step S45. The stored information is given below. It is information relating to the number of inspection analyses by the inspection analysis unit 57, the volume ratio and the difference of the thickness for each inspection analysis, and whether it was set to an evaluation region for each inspection.

At step S45, the inspection analysis unit 57 adds 1 to a count N of a counter which counts the number of inspection analyses of the specimen S; the flow then proceeds to step S46. At step S46, the inspection analysis unit 57 determines whether the number of inspection analyses of the specimen S is greater than or equal to a predetermined number of times. When the number of inspection analyses is greater than or equal to a predetermined number of times, that is, when the count N of the counter is greater than or equal to a threshold Nth, an affirmative determination is made at step S46; the flow then proceeds to step S47. When the number of inspection analyses is less than a predetermined number of times, that is, when the count N of the counter is less than the threshold Nth, a negative determination is made at step S46; the processing then ends.

At step S47, the non-defect analysis unit 573 calculates the evaluation coefficient of the lattice grid 650; the flow then proceeds to step S48. At step S48, the non-defect determination unit 574 determines whether the calculated evaluation coefficient is greater than or equal to the first threshold (or if it exceeds the first predetermined range). When the evaluation indicator is greater than or equal to the first threshold (or exceeds the first predetermined range), an affirmative determination is made at step S48; the flow then proceeds to evaluation region change processing in step S33, the details of which are described hereinafter. Note that in this case, an addition change flag which shows that it is desirable to add a region of the specimen S corresponding to the lattice grid 650 to the evaluation region 600 is set to ON.

When the evaluation coefficient is less than the first threshold (or does not exceed the first predetermined range), a negative determination is made at step S48; the flow then proceeds to step S49. At step S49, the non-defect determination unit 574 determines whether the evaluation coefficient is less than a second threshold (or is in a second predetermined range). When the evaluation coefficient is less than the second threshold (or is in the second predetermined range), an affirmative determination is made at step S49; the flow then proceeds to evaluation region change processing in step S33, the details of which are described hereinafter. Note that in this case, a possible deletion flag showing that it is possible to delete a region of the specimen S corresponding to the lattice grid 650 from the evaluation region 600 is set to ON. When the evaluation coefficient is greater than or equal to the second threshold (or exceeds the second predetermined range), a negative determination is made at step S49; the processing then ends.

—Evaluation Region Change Processing—

In evaluation region change processing, display for recommending changes for the evaluation region 600 to an operator based on the results of evaluation region analysis processing is performed on the display monitor 6. When an operation for performing a change to the evaluation region 600 is performed by an operator, a new evaluation region 600 that reflects the results of evaluation region analysis processing is set, and the coordinate values thereof are stored in the data accumulation unit 58. As a result, during measurement the following time and thereon, the selection of the sliced plane 700 and the sliced range 720 described above is performed based on the new evaluation region 600, and measurement of the specimen S is performed. A detailed description is given below.

Relating to the lattice grid 650 that has the addition change flag set to ON by the non-defect determination unit 574, when the lattice grid 650 exists on the outer periphery of the gridified evaluation region transmission image, the region correction unit 575 creates data for a corrected evaluation region. In this case, when there is a lattice grid 650 that has the addition change flag set to ON, the region correction unit 575 creates data for a corrected evaluation region. Note that in the following description, the lattice grid 650 that has the addition change flag set to ON is called the lattice grid 655 scheduled to be changed.

Figure 31A:
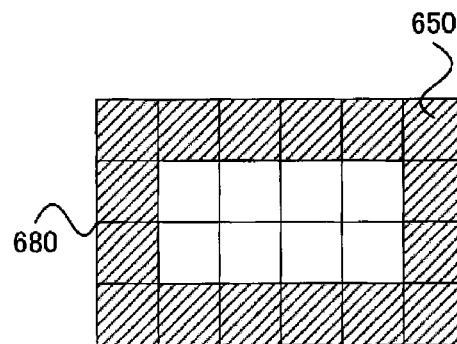
FIGS. 31A to 31D are figures schematically illustrating regarding generation of data for a corrected evaluation region.
Figure 31B:
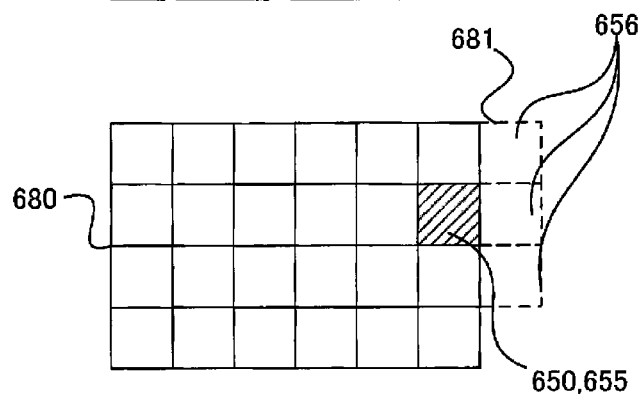
Figure 31C:
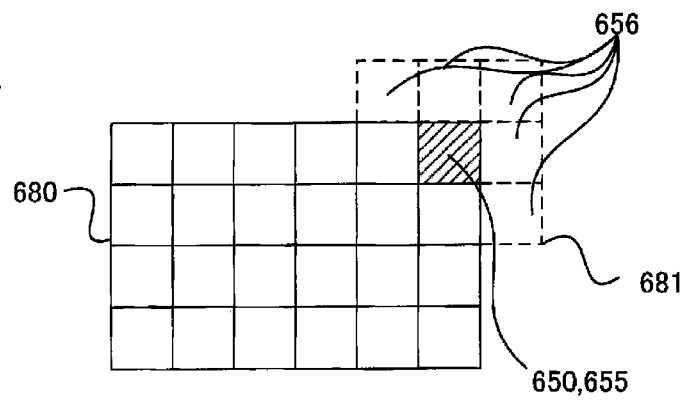
Figure 31D:
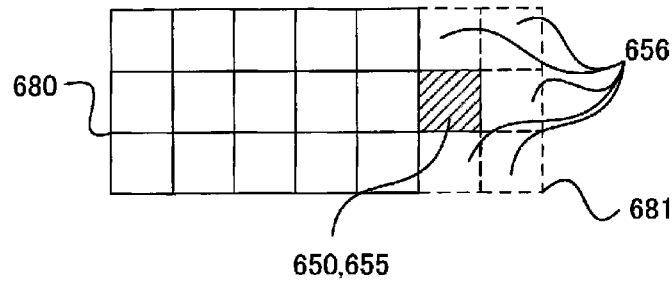

The creation of data for a corrected evaluation region is schematically illustrated in FIGS. 31A to 31D. Note that the actual processing is performed in three dimensions, though it is expressed in two dimensions to understand the invention in FIGS. 31A to 31D. When the outer periphery of the gridified evaluation region 680 illustrated in FIG. 31A, that is, one of the lattice grids 650 illustrated with a slanted line, exceeds the first threshold, the region correction unit 575 creates data for a corrected evaluation region. An example of data for a corrected evaluation region created by the region correction unit 575 is schematically illustrated in FIGS. 31B to 31D. In FIG. 31B, the lattice grid 650, which has slanted lines from among the gridified evaluation region 680, is the lattice grid 655 scheduled to be changed, and it is assumed that a lattice grid 650 exists on the exterior of the gridified evaluation region 680. At this time, the three regions 656 illustrated with a dotted line are the lattice grid 656 (below, the additional lattice grid) surrounding the lattice grid 655 scheduled to be changed. When the lattice grid 655 scheduled to be changed exists in the position illustrated in FIG. 31C, the five additional lattice grids 656 illustrated by the dotted line exist in the periphery. When the lattice grid 655 scheduled to be changed exists in the position of the gridified evaluation region 680 that protrudes having the shape illustrated in FIG. 31D, the five additional lattice grids 656 illustrated by the dotted line exist in the periphery. The region correction unit 575 adds the additional lattice grid 656 to the gridified evaluation region 680, and creates the corrected evaluation region data 681 so that it includes the region illustrated by the additional lattice grid 656 for the evaluation region 600. Relating to the lattice grid 650 that has the possible deletion flag set to ON by the non-defect determination unit 574, the region correction unit 575 deletes the lattice grid 650 that has the possible deletion flag set to ON from the gridified evaluation region 680, and creates corrected evaluation region data 681.

When the corrected evaluation region data 681 is created, the display control unit 578 displays an image corresponding to the corrected evaluation region data 681 on the display monitor 6. At this time, the display control unit 578 displays an image corresponding to the corrected evaluation region data 681 on an image illustrating the shape of the specimen S based on design information. In this case, the display control unit 578 causes the mode of display for locations of the corrected evaluation region data 681 that is changed from the gridified evaluation region 680 to differ from the mode of display for locations which is not changed. That is, when the additional lattice grid 656 is added by the region correction unit 575, the display control unit 578 causes the position corresponding to the additional lattice grid 656 to be displayed with, for example, red, and positions corresponding to other lattice grids 650 to be displayed with changed colors such as green. Also, when the lattice grid 650 that has the possible deletion flag set to ON by the region correction unit 575 is deleted, the display control unit 578 may display the positions corresponding to the lattice grid 650 to be displayed with, for example, blue, and the other lattice grids 650 to be displayed with changed colors such as green.

Note that without limiting to displaying with differing colors, changing the line thickness and the type of line (solid line, dotted line, dash-dot line) is also included in an aspect of the present invention. When displaying history data of the corrected evaluation region data 681 on the display monitor 6, history data for evaluation regions 600 with similar shapes may be displayed side by side. For example, when displaying history data for the corrected evaluation region data 681 for the evaluation region 601 of one crankshaft journal unit, by displaying the history data for the evaluation region 601 of another crankshaft journal unit, one can decide whether a casting plan is good or bad.

Also, for a non-defect level calculated by each lattice grid 650 of a gridified evaluation region contained in the same evaluation region 600, a possible deletion flag may be set for the entire evaluation region 600 according to the non-defect level average value and non-defect level distribution value for each evaluation region 600. In this case, for example, it may be displayed with differing colors to encourage deletion of one or the other from the gridified evaluation region or the evaluation region.

An operator can, by observing the display monitor 6 on which the above display has been performed, from a result of measurement, grasp how the evaluation region 600 should be corrected to be desirable for measuring the interior defects such as cavities of the specimen S. When adopting a correction of the gridified evaluation region transmission image 680 via the region correction unit 575, an operator performs the adoption operation by clicking on an "OK" button or the like displayed on the display monitor 6 using, for example, a mouse or the like composing the input operation unit 11. When an operation signal is output from the input operation unit 11 according to the adoption operation of the operator, the region resetting unit 577 sets a region on the specimen S corresponding to the corrected evaluation region data 681 created by the region correction unit 575 as the new evaluation region 600, and stores the coordinate values thereof in the data accumulation unit 58. At this time, the region resetting unit 577 stores the date and time when the new evaluation region 600 was set, information for identifying the operator who decided to adopt the new evaluation region 600 (name, ID, or the like), the position of the new evaluation region 600 (an index number or the like), notes or comments input by the operator, and the like as related information into the data accumulation unit 58.

Note that the display control unit 578 can display a variety of data on the display monitor 6 when displaying an image of the corrected evaluation region data 681 described above. As data to be displayed at this time, there is the non-defect level of the additional lattice grid 656 or the lattice grid 650 that has the possible deletion flag set to ON, the volume ratio and the difference of the thickness, which is a factor for determining non-defect level. Also, history data having been acquired from shape information or inspection analysis of the specimen S in the past as data to be displayed can be displayed. Also, a photograph acquired separately of the specimen S taken by an optical camera may be stored as a history data. In particular, when the position of the lattice grid 650 matches the surface region of the specimen S, it is desirable to include photograph data taken by an optical camera in the history data. As history data, there is a transition of non-defect level, volume ratio, and thickness. In this case, it should be displayed in a graph format wherein the number of inspection analyses is the horizontal axis and the frequency of the evaluation coefficient, the volume ratio, and the difference of the thickness is the vertical axis. Further, as history data, the transition of the shape change of the evaluation region 600 can also be displayed overlapping the image of the shape of the specimen S. In the case that a shape change was carried out on the evaluation region 600 a plurality of times, it is desirable to have the display mode (color, line thickness, line type, and the like) of the image of each evaluation region 600 be caused to differ.

Note that history data like that described above is not limited to the corrected evaluation region, and it is desirable to display it on the lattice grid 650 in an evaluation region that does not need correction. This is because knowing the change in determining factors of non-defectiveness is helpful in predicting defective products generated in the future. Also, in order to reduce the load on an inspector of mass-produced goods, the history data may be displayed in evaluation region units, instead of displaying history data in lattice grid units. In particular, concerning the non-defect level, even within the same evaluation region, it may differ between individual lattice grids 650. In such a case, the evaluation coefficient in the evaluation region should be set according to the average value, dispersion, or the like of the non-defect level calculated at each lattice grid 650 in the same evaluation region. Also, the display of history data by simply displayed to an operator regardless of the existence of a correction process of the evaluation region brings about an effect to save labor in the inspection process of quality assurance for the mass-produced good.

Figure 32:
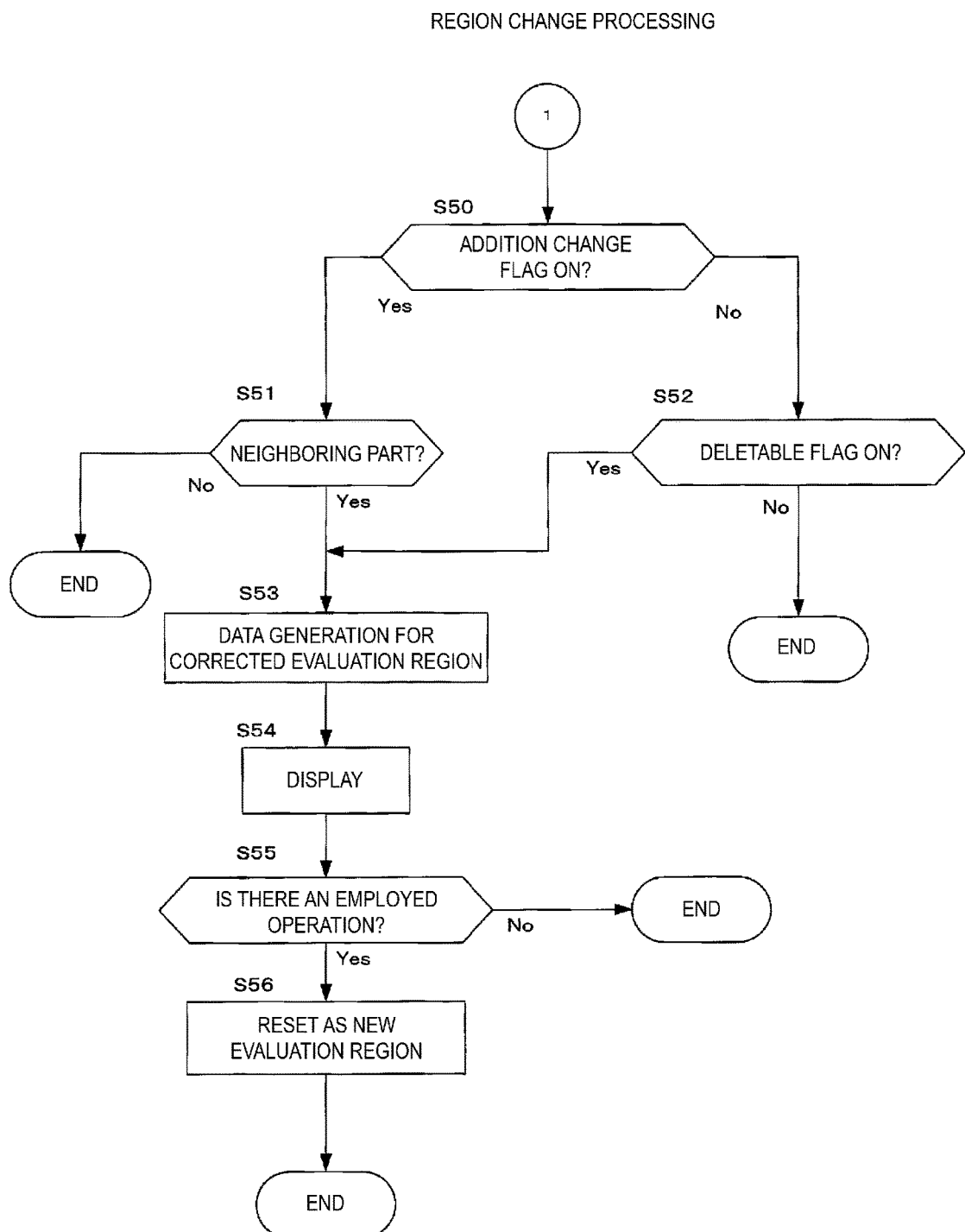
FIG. 32 is a flowchart illustrating the behavior in evaluation region change processing.

Evaluation region change processing of step S33 of FIG. 28 is described with reference to the flowchart of FIG. 32.

At step S50, the region correction unit 575 determines whether the addition change flag of the lattice grid 650 is set to ON. When the addition change flag is set to ON, an affirmative determination is made at step S50; the flow then proceeds to step S51. Step S51 determines whether the lattice grid 650 exists on the peripheral part of the gridified evaluation region 680. When it is not in the peripheral part of the gridified evaluation region 680, a negative determination is made at step S51; the processing then ends. When it is in the peripheral part of the gridified evaluation region 680, an affirmative determination is made at step S51; the flow then proceeds to step S53.

At step S50, when the addition change flag is set to OFF, a negative determination is made at step S50; the flow then proceeds to step S52. At step S521, it is determined whether the possible deletion flag of the lattice grid 650 is set to ON. When the possible deletion flag is set to OFF, a negative determination is made at step S52; the processing then ends. When the possible deletion flag is set to ON, an affirmative determination is made at step S52; the flow then proceeds to step S53. At step S53, the region correction unit 575 creates the corrected evaluation region data 681; the flow then proceeds to step S54.

At step S54, the display control unit 578 displays the image corresponding to the corrected evaluation region data 681 overlapping the image corresponding to the shape of the specimen S; the flow then proceeds to step S55. At step S55, it is determined whether an adoption operation has been performed by an operator. When an operation signal according to the adoption operation of the operator is input from the input operation unit 11, an affirmative determination is made at step S55; the flow then proceeds to step S56. When an operation signal according to the adoption operation is not input from the input operation unit 11, a negative determination is made at step S55; the processing then ends. At step S56, the region on the specimen S corresponding to the corrected evaluation region data 681 is set as a new evaluation region 600, the coordinate value is stored in the data accumulation unit 58; the processing then ends.

—Broad Region Analysis Processing—

In broad region analysis processing, internal defects such as cavities in the region other than the evaluation region 600 are detected from the transmission image of the specimen S obtained from a full scan, and analysis is performed relating to non-defectiveness of the specimen S, such as a high possibility of the specimen S being a defective product due to the detected cavities, a possibility of strength insufficiency, a possibility of a leak occurring, and the like. A detailed description is given below.

When performing broad region analysis processing, processing simplification is attained by performing processing on lattice grid 650 units for the obtained shape information of the specimen S. Because of this, the lattice gridified unit 570 compartmentalizes by lattice grid 650 the broad shape information containing regions other than the evaluation region 600 obtained from a full scan. Below, the volume ratio analysis unit 571, the thickness analysis unit 572, the non-defect analysis unit 573, and the non-defect determination unit 574 perform similar processing to the processing for each lattice grid 650 described in the evaluation region analysis processing described above. As a result, when, among the shape information of the grified broad region, the evaluation coefficient of the lattice grid 650 of the region different from the region corresponding to the evaluation region 600 is greater than or equal to the first threshold, the non-defect determination unit 574 determines that the region of the specimen S corresponding to that lattice grid 650 has a high possibility of generating a defect. In this case, the non-defect determination unit 574 sets a new addition flag to ON, showing that it is desirable to newly add the lattice grid 650 as a new evaluation region 600.

Figure 33:
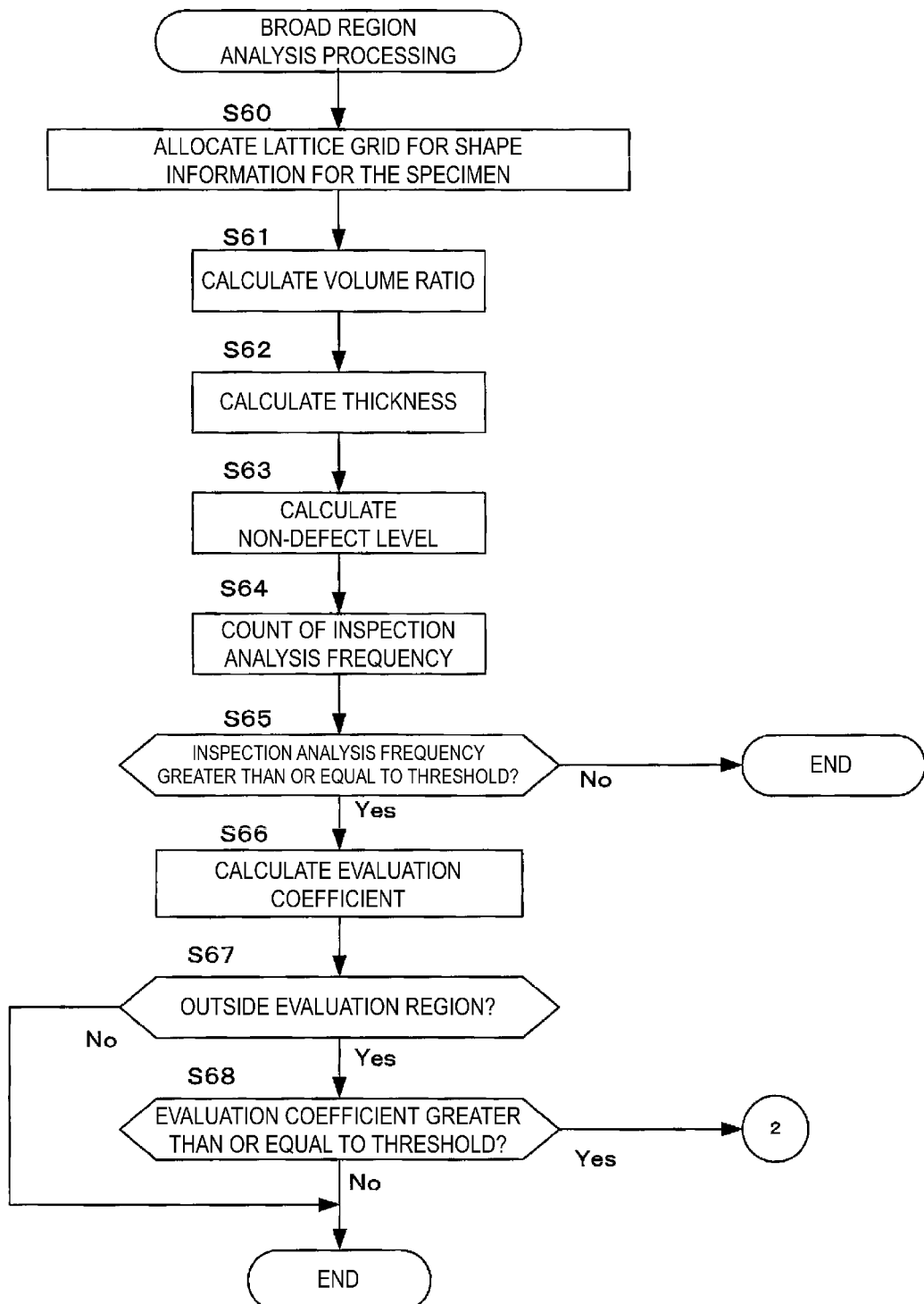
FIG. 33 is a flowchart illustrating the behavior in broad region analysis processing.

Broad region analysis processing of step S34 of FIG. 28 is described with reference to the flowchart of FIG. 33.

At step S60, the lattice gridified unit 570 sets the lattice grid 650 for the shape information of the entire specimen S created based on the transmission image obtained from a full scan; the flow then proceeds to step S61. Each processing from step S61 (volume ratio calculation) to step S67 (determining whether the evaluation coefficient is greater than or equal to a threshold) is the same as each processing from step S42 (volume ratio calculation) to step S47 (determining whether the evaluation coefficient is greater than or equal to a threshold) of FIG. 30. However, the above processing is performed for each lattice grid 650, even for regions outside the region corresponding to the evaluation region 600.

Step S68 determines whether region on the specimen S corresponding to the lattice grid 650 determined to have an evaluation coefficient that is greater than or equal to the first threshold (or exceeding the first predetermined range) is a region outside the evaluation region 600. When it is a region other than the evaluation region 600, an affirmative determination is made at step S68; the flow then proceeds to step 35 in FIG. 28. In this case, the new addition flag of the lattice grid 650 is set to ON. When the region corresponding to this lattice grid 650 is the evaluation region 600, a negative determination is made at step S68; the processing then ends.

Figure 30:
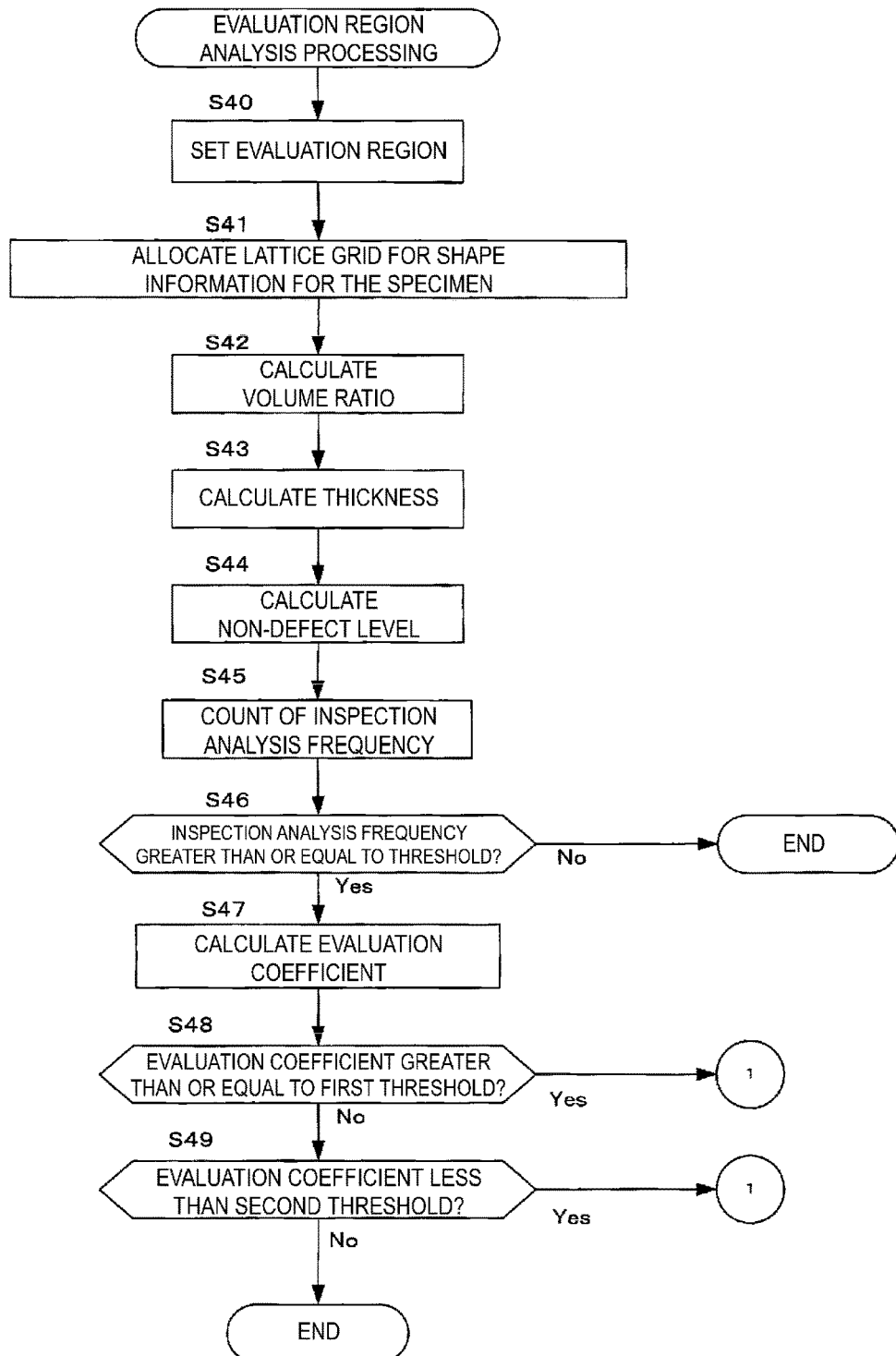
FIG. 30 is a flowchart illustrating the action in evaluation region analysis processing.

Note that in the broad region analysis processing, one may execute step S48 of FIG. 30 to the lattice grid 650 in the evaluation region 600. In this case, the aforementioned processing is performed after step S66.

—Evaluation Region Addition Processing—

In evaluation region addition processing, display for recommending to an operator the addition of a new evaluation region 600 is performed on the display monitor 6 based on the results of broad region analysis processing. When an operation for performing a new addition of the evaluation region 600 is performed by an operator, a new evaluation region 600 is added and set, and the coordinate values thereof are stored in the data accumulation unit 58. As a result, during measurement the following time and thereon, the selection of the sliced plane 700 and the sliced range 720 described above is performed based on the newly added evaluation region 600, and measurement of the specimen S is performed. A detailed description is given below.

The region addition unit 576 identifies the lattice grids 650 that have a new addition flag set to ON by the non-defect determination unit 574 as data for a newly added evaluation region. When data for the newly added evaluation region is created, the display control unit 578 displays an image corresponding to the data for the newly added evaluation region on the display monitor 6. At this time, the display control unit 578 displays an image corresponding to the data of the newly added evaluation region on an image illustrating the shape of the specimen S based on design information. Note that in this case also, the display control unit 578 can display various data and history data in the same manner as the case described for evaluation region correction processing.

An operator can, by observing the display monitor 6 on which the above display has been performed, from a result of measurement, grasp how the new evaluation region 600 should be added to be desirable for measuring the interior defects such as cavities of the specimen S. When adopting an addition of the data of the newly added evaluation region via the region addition unit 576, an operator performs the adoption operation by clicking on an "OK" button or the like displayed on the display monitor 6 using, for example, a mouse or the like composing the input operation unit 11. When an operation signal is output from the input operation unit 11 according to the adoption operation of the operator, the region resetting unit 577 sets a region on the specimen S corresponding to the data of the newly added evaluation region created by the region addition unit 576 as the new evaluation region 600, and stores the coordinate values thereof in the data accumulation unit 58. At this time, the region resetting unit 577 stores the date and time when the new evaluation region 600 was set, information for identifying the operator who decided to adopt the new evaluation region 600 (name, ID, or the like), the position of the new evaluation region 600 (an index number or the like), notes or comments input by the operator, pictures (image data) and the like illustrating the outer appearance of the specimen S at that time, and the like as related information into the data accumulation unit 58.

Figure 34:
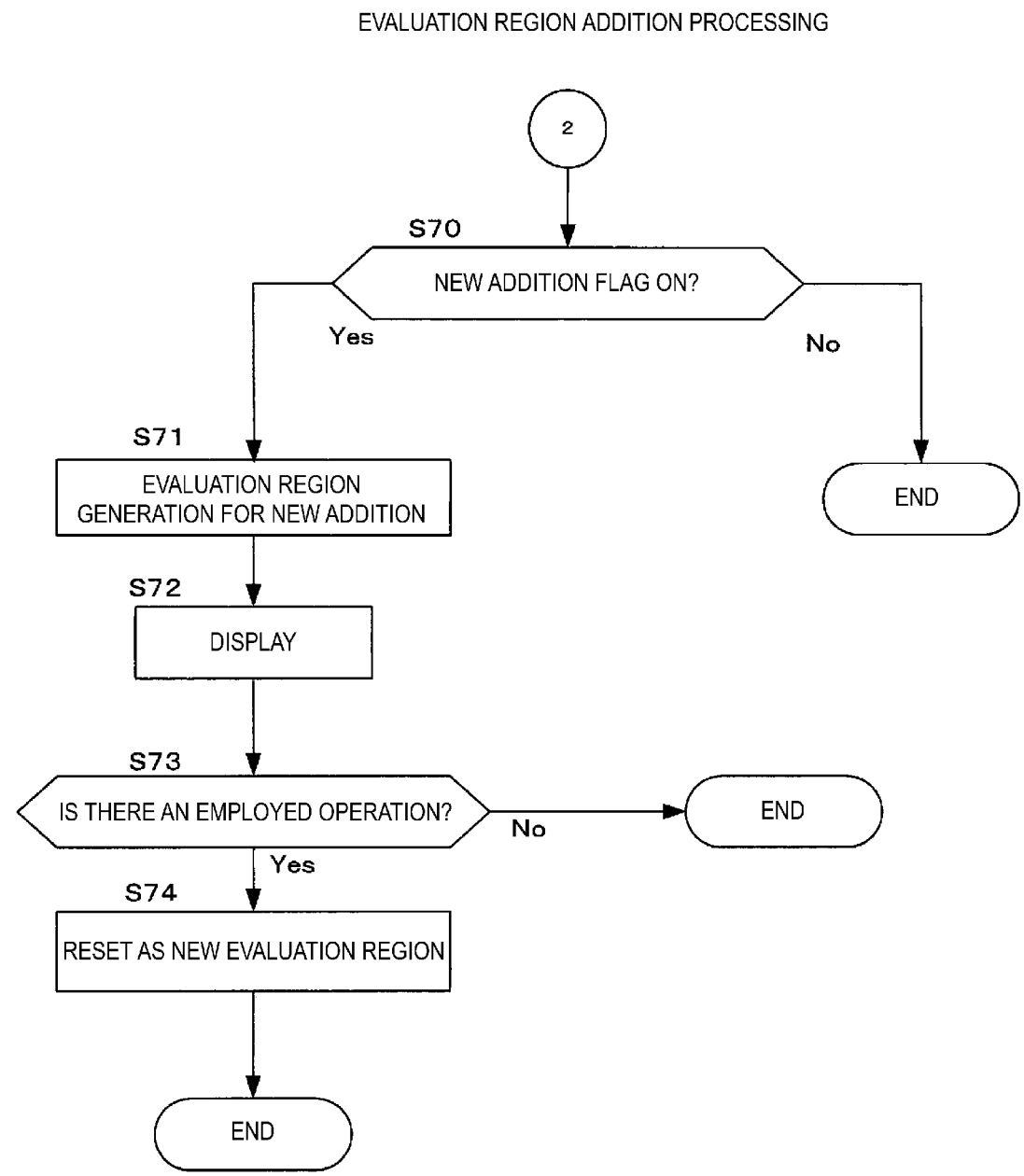
FIG. 34 is a flowchart illustrating the behavior in evaluation region addition processing.

Evaluation region addition processing of step S35 of FIG. 28 is described with reference to the flow chart of FIG. 34.

At step S70, the region addition unit 576 determines whether the new addition flag is ON for the lattice grid 650. When the new addition flag is set to OFF, a negative determination is made at step S70; the processing then ends. When the new addition flag is set to ON, an affirmative determination is made at step S70; the flow then proceeds to step S71.

At step S71, the region addition unit 576 identifies the lattice grid 650 as data for the newly added evaluation region; the flow then proceeds to step S72. At step S72, the display control unit 578 displays an image corresponding to data of the newly added evaluation region overlapping an image corresponding to the shape of the specimen S; the flow then proceeds to step S73. At step S73, it is determined whether or not an adoption operation was performed by an operator. When an operation signal according to the adoption operation of the operator is input from the input operation unit 11, an affirmative determination is made at step S73; the flow then proceeds to step S74. When an operation signal according to the adoption operation is not input from the input operation unit 11, a negative determination is made at step S73; the processing then ends. At step S74, regions on the specimen S corresponding to the data of the newly added evaluation region are set as the new evaluation regions 600, and the coordinate values thereof are stored in the data accumulation unit 58; the processing then ends.

An embodiment of the structure manufacturing system containing the x-ray inspection device 100 by embodiments of the present invention, discussed above, is described next. The structure manufacturing system creates molded component such as, for example, a door portion, an engine portion, or a gear portion of an automobile, or an electronic component that incorporates an electrical circuit board and the like.

Figure 35:
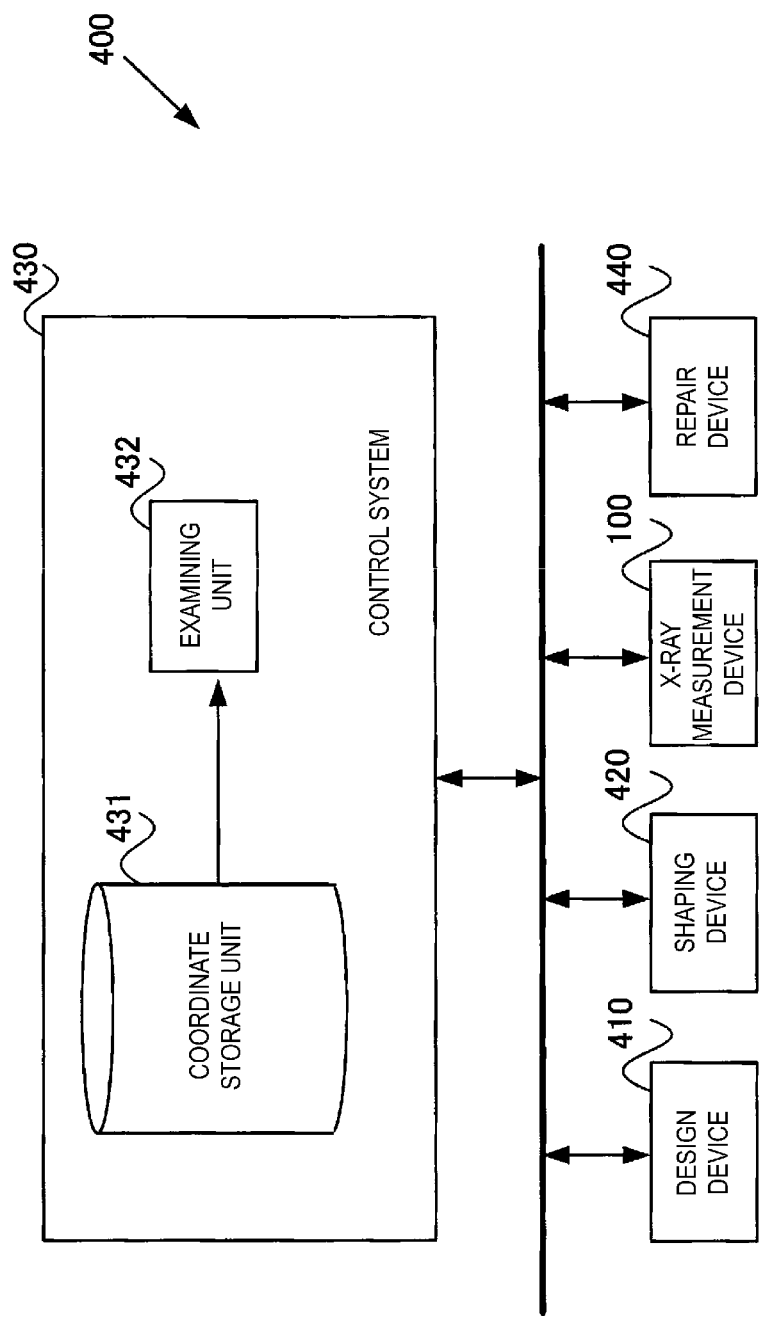
FIG. 35 is a block diagram illustrating an example of a configuration of a structure manufacturing system according to the embodiments.

FIG. 35 is a block diagram illustrating one example of a configuration of a structure manufacturing system 400 according to the present embodiment. The structure manufacturing system 400 is provided with the x-ray inspection device 100 described in the embodiment, a design device 410, a molding device 420, a control system 430, and a repair device 440.

The design device 410 is a device used by a user when creating design information relating to a shape of a structure and performs design processing for creating and storing the design information. The design information is information indicating coordinates of each position of the structure. The design information is output to the molding device 420 and the control system 430, which is described below. The molding device 420 performs molding processing for creating and molding the structure using the design information created by the design device 410. In this case, a molding device 420 that performs at least one of laminating which is representative in 3D-printer technology, casting, forging, and cutting is also included in one aspect of the present invention.

The x-ray inspection device 100 performs inspection processing for inspecting a shape of the structure molded by the molding device 420. The x-ray inspection device 100 outputs to the control system 430 information indicating coordinates of the structure ("shape information" hereinbelow), which is an inspection result of inspecting the structure. The control system 430 is provided with a coordinate storage unit 431 and an inspection unit 432. The coordinate storage unit 431 stores the design information created by the design device 410 described above.

The inspection unit 432 determines whether the structure molded by the molding device 420 is molded according to the design information created by the design device 410. In other words, the inspection unit 432 determines whether the molded structure is a non-defective product. In this case, the inspection unit 432 reads the design information stored in the coordinate storage unit 431 and performs inspection processing comparing the design information and the shape information input from the x-ray inspection device 100. For the inspection processing, the inspection unit 432 compares, for example, the coordinates indicated by the design information and the corresponding coordinates indicated by the shape information and determines that the molded structure is a non-defective product molded if the result of this inspection processing shows that the coordinates of the design information and the coordinates of the shape information match. When the coordinates of the design information and the corresponding coordinates of the shape information do not match, the inspection unit 432 determines whether a difference between the coordinates is within a predetermined range and determines that the molded structure is a repairable defective product if this difference is within the predetermined range.

When it determines that the molded structure is a repairable defective product, the inspection unit 432 outputs to the repair device 440 repair information indicating a defective area and a repair amount. The defective area is the coordinates of the shape information that do not match the coordinates of the design information, and the repair amount is the difference between the coordinates of the design information and the coordinates of the shape information at the defective area. The repair device 440 performs repair processing for re-machining the defective area of the structure based on the input repair information. In the repair processing, the repair device 440 performs again processing similar to the molding processing performed by the molding device 420.

Figure 36:
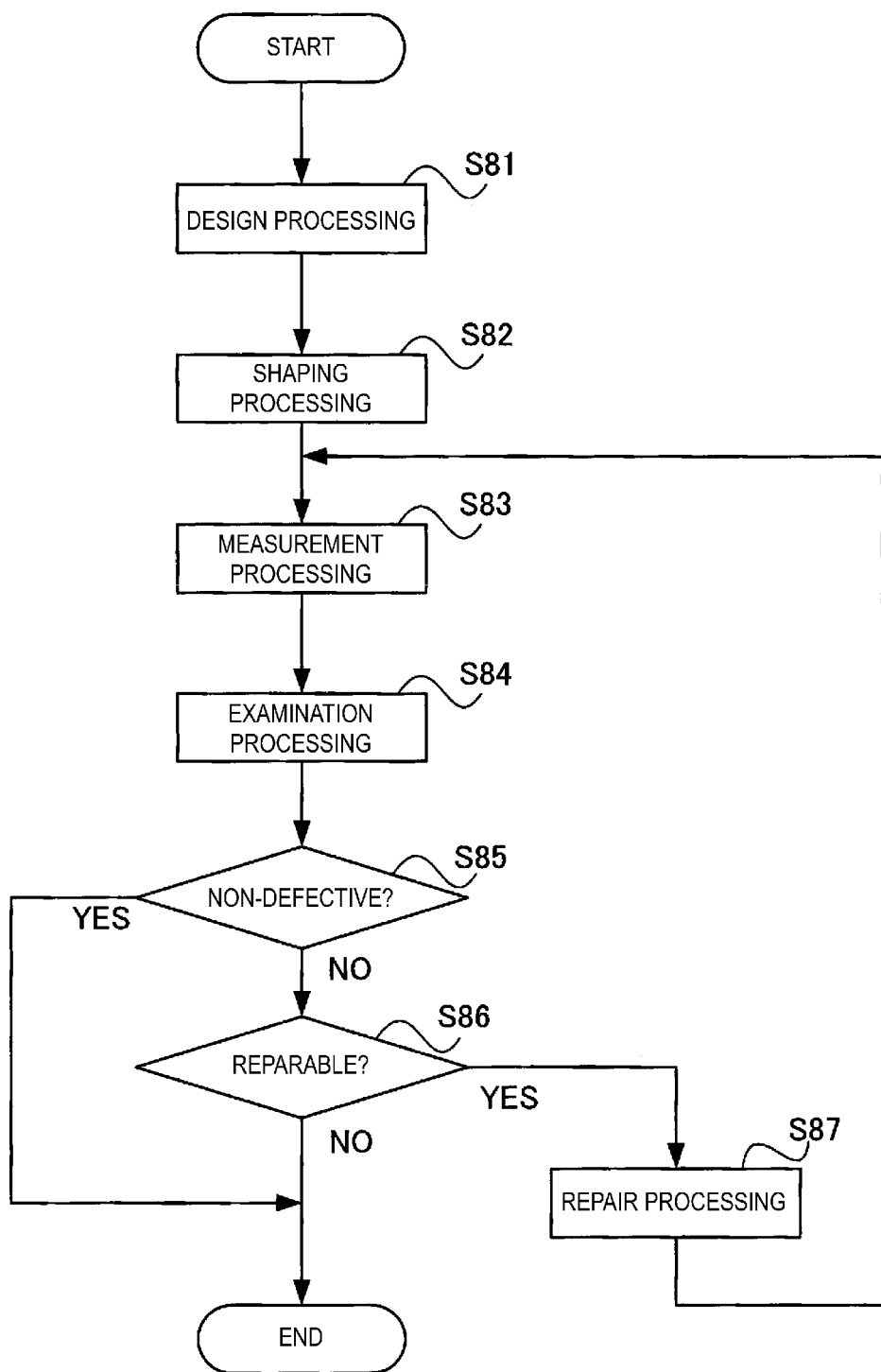
FIG. 36 is a flowchart illustrating the processing of a structure manufacturing system.

The processing performed by the structure manufacturing system 400 is described with reference to the flowchart illustrated in FIG. 36.

At step S81, the design device 410 is used when the user designs the structure and the design information relating to the shape of the structure is created and stored by the design processing; the flow then proceeds to step S82. Note that the present invention is not limited to only the design information created by the design device 410; when design information already exists, inputting this design information to acquire the design information is also included in one aspect of the present invention. At step S82, the molding device 420 creates and molds the structure based on the design information by the molding processing; the flow then proceeds to step S83. At step S83, the x-ray inspection device 100 performs the inspection processing to measure the shape of the structure and outputs the shape information; the flow then proceeds to step S84.

At step S84, the inspection unit 432 performs the inspection processing to compare the design information created by the design device 410 and the shape information inspected and output by the x-ray inspection device 100; the flow then proceeds to step S85. At step S85, the inspection unit 432 determines based on the result of the inspection processing whether the structure molded by the molding device 420 is a non-defective product. When the structure is a non-defective product, that is, when the coordinates of the design information and the coordinates of the shape information match, an affirmative determination is made at step S85; the processing then ends. When the structure is not a non-defective product, that is, when the coordinates of the design information and the coordinates of the shape information do not match or when coordinates that are not present in the design information are detected, a negative determination is made at step S85; the flow then proceeds to step S86.

At step S86, the inspection unit 432 determines whether the defective area of the structure is repairable. When the defective area is unrepairable, that is, when the difference between the coordinates of the design information and the coordinates of the shape information exceeds the predetermined range, a negative determination is made at step S86;

the processing then ends. When the defective area is repairable, that is, when the difference between the coordinates of the design information and the coordinates of the shape information is within the predetermined range, an affirmative determination is made at step S86; the flow then proceeds to step S87. In this case, the inspection unit 432 outputs the repair information to the repair device 440. At step S87, the repair device 440 performs the repair processing on the structure based on the input repair information; the flow then returns to step S83. Note that as described above, the repair device 440 performs again processing similar to the molding processing performed by the molding device 420 in the repair processing.

According to the embodiments described above, the following actions and effects are obtained.

(1) The sliced plane selection unit 563 calculates the respective amounts of displacement of the plurality of sliced regions selected by the sliced plane candidates 701, 702, 703 for the gridified evaluation region 610 corresponding to the three-dimensional evaluation region 600 set by the evaluation region setting unit 561 and selects the sliced plane 700 that is a sliced region from among the sliced plane candidates 701 to 703 based on the calculated amount of displacement. Therefore, because the sliced plane 700 that breaks the three-dimensional shape of the evaluation region 600 set on the specimen S can be determined automatically based on the amount of displacement in the y direction, compared to when the operator sets the sliced plane 700 based on an experiential determination according to the evaluation region 600, a more efficient sliced plane 700 from a viewpoint of measurement time can be selected. Particularly, when measuring the specimen S at a mass-production stage, efficiency improvement of the measurement time contributes effectively to improved productivity.

(2) The sliced plane selection unit 563 calculates the respective amounts of displacement of the plurality of sliced regions selected by the sliced plane candidates 701, 702, 703 for each of the gridified evaluation regions 610 corresponding to the plurality of evaluation regions 600 and selects the sliced plane 700 that is a sliced region from among the sliced plane candidates 701 to 703 based on the calculated amounts of displacement for each of the gridified evaluation regions 610 corresponding to the plurality of evaluation regions 600. Therefore, even when a plurality of evaluation regions 600 is set on the specimen S, it is possible to select a sliced plane 700 for the individual evaluation region 600 with favorable efficiency from the viewpoint of measurement time.

(3) The sliced plane selection unit 563 selects from among the amounts of displacement of the plurality of sliced regions selected by the sliced plane candidates 701, 702, 703 the sliced plane 700 that is a sliced region with the small amount of movement in moving the cross section of the specimen S by the slit beam to detect the evaluation region 600. Therefore, because a sliced plane 700 with a small amount of displacement can be selected, the measurement time of the evaluation region 600 can be shortened. Because shortening the measurement time enables early detection of a problem of the specimen S and an early countermeasure for the problem, particularly at the mass-production stage, productivity can be improved.

(4) The grouping unit 565 classifies the gridified evaluation regions 610 corresponding to the plurality of evaluation regions 600 into the first group G1 where the first sliced plane 711 is selected and the second group G2 where the second sliced plane 712 is selected. The inspection unit 564 controls the x-ray source 2, the detector 4, and the placing unit 3 to perform measurement by x-ray detection for each of the evaluation regions 600 corresponding to the gridified evaluation regions 610 belonging to the first group G1 and afterward perform measurement by x-ray detection for each of the evaluation regions 600 corresponding to the gridified evaluation regions 610 belonging to the second group G2. Therefore, by classifying a plurality of evaluation regions 600 extending in similar directions belongs to the same group, it can be prevented the amount of displacement of the sliced plane 700 from increasing due to an influence of evaluation regions 600 extending in different directions and the measurement time from increasing, which enables shortening of the measurement time. Moreover, by measuring a plurality of evaluation regions 600 belonging to the same group before performing measurement for the plurality of evaluation groups 600 belonging to another group, a change count of the placement orientation of the specimen S can be kept minimal and an increase in the measurement time, which accompanies a placement orientation change of the specimen S, can be suppressed.

(5) If a plurality of gridified evaluation regions 610 is present in the displaced position of at least one portion when the sliced plane 700 is displaced in a gridified evaluation region 610, the sliced plane selection unit 563 combines the gridified evaluation regions 610 into one gridified evaluation region 611. Therefore, compared to selection of the sliced plane 700 and the sliced region 720 for individual evaluation regions 600, more efficient selection of the sliced plane 700 and the sliced region 720 is possible. Moreover, because work requiring experience of combining a plurality of evaluation regions 600 into one in order to shorten the measurement time can be performed automatically, convenience can be improved.

(6) The grouping unit 565 classifies the plurality of gridified evaluation regions 610 belonging to the first group G1 into the third group G3 and the fourth group G4 with different transmission image magnifications and classifies the plurality of gridified evaluation regions 610 belonging to the second group G2 into the third group G3 and the fourth group G4. The measuring unit 564 causes measurement to be performed for each of the evaluation regions 600 corresponding to the gridified evaluation regions 610 belonging to the third group G3 among the first group G1 and causes measurement to be performed for each of the evaluation regions 600 corresponding to the gridified evaluation regions 610 belonging to the fourth group G4. Afterward, the measuring unit 564 causes measurement to be performed for each of the evaluation regions 600 corresponding to the gridified evaluation regions 610 belonging to the fourth group G4 among the second group G2 and causes measurement to be performed for each of the evaluation regions 600 corresponding to the gridified evaluation regions 610 belonging to the third group G3. Therefore, even when a large evaluation region 600 and a minute evaluation region 600 for measuring a cavity are in mixed distribution, grouping according to the displacement direction of the sliced plane 700 and the magnification of the transmission image is possible and the transmission image can be acquired at a large magnification from the minute evaluation region 600 while suppressing an increase in the measurement time.

(7) The grouping unit 565 classifies the grouping evaluation regions 610 corresponding to the plurality of evaluation regions 600 into the third group G3 and the fourth group G4 that measure at different transmission image magnifications. Therefore, even when a minute evaluation region 600 for measuring a cavity is included in the plurality of evaluation regions 600, a transmission image with a large magnification can be obtained for the minute evaluation region 600 and generation conditions and the like of the cavity can be analyzed in detail.

(8) The grouping unit 565 classifies the plurality of gridified evaluation regions 610 belonging to the third group G3 into the first group G1 where the first sliced plane 711 is selected and the second group G2 where the second sliced plane 712 is selected and classifies the plurality of gridified evaluation regions 610 belonging to the fourth group G4 into the first group G1 where the first sliced plane 711 is selected and the second group G2 where the second sliced plane 712 is selected. Therefore, even when a plurality of evaluation regions 600 extending in different directions and a minute evaluation region 600 are in mixed distribution, acquiring the transmission image at a large magnification for the minute evaluation region 600 is possible.

(9) The plurality of gridified evaluation regions 610 includes the gridified evaluation region 610 having the settable range R that is displacable within the predetermined range, and the region resetting unit 567 displaces in the predetermined range the gridified evaluation region 610 having the settable range R so that both the gridified evaluation region 610 having the settable range R and the other gridified evaluation regions 610 are included in the sliced plane 700 and resets the gridified evaluation regions 610. Therefore, evaluation regions 600 present in separated positions can be measured in combination to improve working efficiency.

(10) The region resetting unit 567 displaces within the predetermined range the gridified evaluation region 610 having the settable range R in order to increase positions where both the gridified evaluation region 610 having the settable range R and the gridified evaluation regions 610 not having the settable range R can be detected by the selected sliced plane 700. Therefore, the amount of displacement of the sliced plane 700 can be decreased to shorten the measurement time.

(11) The region resetting unit 567 moves within the predetermined range the gridified evaluation region 610 having the settable range R so that the gridified evaluation region 610 having the settable range R and the gridified evaluation regions 610 not having the settable range R overlap. Therefore, because a plurality of evaluation regions 600 can be measured at once in a measurement time required for one evaluation region 600, working efficiency can be improved.

(12) The magnification calculation unit 568 uses the information of the evaluation region 600 set by the region setting unit 561 to calculate the magnification when the evaluation regions 600 of the specimen S are measured. Therefore, because a plurality of evaluation regions 600 can be measured at once at a high magnification, measurement can be performed efficiently.

(13) The non-defect determination unit 574 uses the transmission image of the x-ray transmitted through an evaluation region 600 of the specimen S to determine the non-defectiveness of the evaluation region 600, the region correction unit 575 corrects the evaluation region 600 based on the determination result by the non-defect determination unit 574, and the display control unit 578 displays the image of the corrected evaluation region data 681 corrected by the region correcting unit 575. Therefore, because the operator can visually confirm whether the current evaluation region 600 is suited as a position for measuring an internal defect of the specimen S, the determination of whether to change the evaluation region 600 is facilitated.

(14) The display control unit 578 displays the image of the corrected evaluation region data 681 by varying the display mode of the corrected location thereof and the display mode of the other locations. That is, because the changed location of the evaluation region 600 become easy to confirm, the determination of whether to change the evaluation region 600 is facilitated.

(15) When the operation signal according to the adoption operation by the input operation unit 11 is input, the region resetting unit 577 resets the corrected evaluation region data 681 to a portion of the specimen S as a new evaluation region 600. That is, the evaluation region 600 being changed automatically contrary to an intent of the operator can be suppressed.

(16) A new evaluation region 600 is additionally set on a portion of the specimen S based on the shape information representing the shape of the broad region of the specimen S acquired after measurement of the plurality of evaluation regions 600 of the specimen S. In this case, the non-defect determination unit 574 determines the non-defectiveness of the regions other than the evaluation region 600 using the broad region shape information and a region whose non-defectiveness exceeds a predetermined tolerance among the regions other than the evaluation region 600. The region addition unit 576 additionally sets the region whose non-defectiveness exceeds the predetermined tolerance as the new evaluation region 600. Therefore, a location where an internal defect begins to appear in a location not predicted initially can be measured as the evaluation region 600, which contributes to early detection of a problem of the specimen S.

(17) The data accumulation unit 58 stores the history data relating to the evaluation region 600 reset by the region resetting unit 577, and the display control unit 578 displays the image of the corrected evaluation region data 681 superimposed on the image of the specimen S based on the historical data of the evaluation region 600 stored in the data accumulation unit 58. Therefore, because it is possible to confirm visually how the shape of the evaluation region 600 is changed on the specimen S, prediction of a future internal defect location and the like are facilitated.

(18) The data accumulation unit 58 stores the history data relating to the determination result of non-defectiveness by the non-defect determination unit 574, and the region correction unit 575 creates the corrected evaluation region data 681 based on the history data of the determination result of non-defectiveness stored by the data accumulation unit 58. Therefore, grasping what type of internal defect has a high tendency to arise in a certain evaluation region 600 is facilitated.

(19) When the lattice grid 650 where the non-defectiveness of the gridified evaluation region 680 is determined by the non-defect determination unit 574 to exceed the predetermined tolerance is present in the outer peripheral portion of the gridified evaluation region 680, the region correction unit 575 generates the corrected evaluation region data 681 so that the lattice grid 656 scheduled to be changed positioned around the additional lattice grid 655 in this outer peripheral portion is included in the gridified evaluation region 680. When a possibility is high of failure in the outer peripheral portion of the evaluation region 600, a possibility is high of an influence thereof reaching outside the evaluation region 600; therefore, setting of the evaluation region 600 according to conditions of the defect becomes possible.

(20) The region correction unit 575 deletes from the gridified evaluation region transmission image the lattice grid 650 where the non-defectiveness of the gridified evaluation region is determined by the non-defect determination unit 574 to be within the predetermined tolerance. Therefore, by removing from the evaluation region 600 a region where a possibility of a defect arising is low, performing unnecessary measurement is prevented.

(21) The data accumulation unit 58 stores the information relating to correction by the region correction unit 575. Therefore, the information can be shared between the operator who performs updating and new addition of the evaluation region 600 and another operator.

(22) The x-ray inspection device 100 of the structure manufacturing system 400 performs inspection processing for acquiring the shape information of the structure created by the molding device 420 based on the design processing by the design device 410, and the inspection unit 432 of the control system 430 performs inspection processing for comparing the shape information acquired in the inspection processing and the design information created in the design processing. Therefore, inspection of a defect in the structure and information about the inside of the structure can be acquired by a nondestructive inspection to determine whether the structure is a non-defective product created according to the design information, which contributes to quality management of the structure.

(23) The repair device 440 performs the repair processing that performs again molding processing on the structure based on the comparison result of the inspection processing. Therefore, processing similar to the molding processing can be applied again to the structure when the defective portion of the structure is repairable, which contributes to manufacturing a structure of a high quality approaching the design information.

Modifications such as below are also within the scope of the present invention, and it is also possible to combine one modified example or a plurality of modified examples with an embodiment described above.

(1) The x-ray inspection device 100 may have an x-ray source that emits a cone beam and a detector 4 that is not a line sensor and has a structure where pixels are arranged two-dimensionally. In this case, it is favorable to output a signal from the pixels lined up in a line according to the sliced plane 700 from the detector 4. By such a configuration, the sliced plane 700 can be displaced in a direction other than the y direction.

(2) A configuration may be such that the time required to change the placement posture of the specimen S when switching from measurement of the first group G1 to measurement of the second group G2 can be input from the input operation unit 11, and the sliced plane selection unit 563 may select the sliced plane 700 by also taking into consideration this input time. That is, the sliced plane selection unit 563 holds the required time for changing the placement posture of the specimen S and, when adding the necessary time increases an overall measurement time, selects the sliced plane 700 so that there is no accompanying change in the placement posture of the specimen S.

(3) Instead of changing the evaluation region 600 after the adopting operation of the operator is performed, it is preferable to change automatically the evaluation region 600, which is set as the new evaluation region 600 and is stored in the data accumulation unit 58.

(4) In inspecting another specimen of a shape similar to that of the specimen S, for example, a cylinder block of an engine of the same structure but with a different exhaust amount, a similar casting scheme, or the like, a tolerance of non-defectiveness in an evaluation region of the other specimen may be used as the tolerance when determining the non-defectiveness of the evaluation region 600 of the specimen S. As a result, the evaluation region 600 can be optimized in a short period. Moreover, a configuration may be such that the corrected evaluation region can be displayed using corrected historical information of the evaluation region set on the other specimen of the similar shape. Particularly, this facilitates determination by the operator concerning a validity of the corrected evaluation region presented by the evaluation region correction unit.

(5) Based on the history data of the setting value of the non-defect level, history data may be displayed for a lattice grid 650 where it is determined even once over a plurality of measurements that there is a high possibility of a failure. Alternatively, the history data of the lattice grid 650 may also be displayed for a lattice grid 650 whose non-defect level is worsened over time or whose non-defect level is indicated a value near the threshold for a long period although the non-defect level is not worsened.

(6) The display control unit 578 may display history data of the determination result of non-defectiveness stored in the data accumulation unit 58 and a replacement time of the mold used when manufacturing the specimen S. In this case, it is favorable to determine that degradation has occurred in the mold of the specimen S when cavity generation increases over time to exceed a predetermined count and display on the display monitor 6 that it is time to replace the mold.

(7) A size of the lattice grid 650 set on a surface model generated from the data acquired in the full scan may be set to be smaller than a size of the lattice grid 650 at the time of the partial scan. As a result, a processing load required at the time of the partial scan can be reduced and, because information does not become excessive, the operator can readily make various types of determinations (updating the evaluation region 600 and the like) from the display monitor 6.

Conversely, because an information amount of the data obtained in the full scan increases to be more than that of the partial scan, the operator can inspect in detail a cause of a defect arising.

(8) The size of the lattice grid 650 may be made changeable with each measurement. However, a size of the largest lattice grid 650 is preferably a size that is the least common multiple of the set sizes of the other lattice grids 650. Particularly, in the full scan, margins are anticipated in measurement and inspection time. In such a case, it is preferable to set a lattice grid 650 smaller than the lattice grid 650 set at the time of inspection by the partial scan. Moreover, regardless of a size of the scanning range, it is preferable for the operator to be able to set the size of the lattice grid 650 with each measurement. Note that the smaller the size of the lattice grid size 650 is made, the more a precision of defective product prediction can be increased whereby information relating to positional distribution of the non-defect level is acquired in detail.

(9) The shape of the lattice grid 650 is not limited to a cube. For example, with an article of a hollow shape such as a blade portion of a turbine blade, a transmission case, or a differential case, pitches of the lattice grid 650 necessary for inspection differ in a surface direction and a thickness direction of the structure. There is no need to make the lattice grid 650 very small in the surface direction. Meanwhile, there is a need to make the pitch of the lattice grid 650 small in the thickness direction. With such an article, it is preferable to set a lattice grid of a rectangular-parallelepiped shape.

A function of a portion of the inspection processing device 1 in the embodiments described above or the inspection processing device 1 in the modified examples, for example, the inspection control unit 56 or the inspection analysis unit 57, may be realized by a computer. In this case, this may be realized by recording a program for realizing this control function in a recording medium that can be read by a computer and causing a computer system to read and execute the program relating to the control described above. Note that a "computer system" referred to here includes an OS (operating system) and hardware such as a peripheral. Moreover, a "recording medium that can be read by a computer" refers to a portable recording medium such as a flexible disk, a magneto-optical disk, an optical disk, or a memory card or a storage device such as a hard drive that is built in with the computer system. Moreover, the "recording medium that can be read by a computer" may also include a medium that holds the program for a certain amount of time such as a medium that dynamically holds the program for a short time such as a communication line when sending the program via a network such as the Internet or a communication line such as a phone line or a volatile memory inside the computer system serving as a server or a client in this case. Moreover, the program above may be for realizing a portion of the function described above; the function described above may be realized by a combination of this program with a program already recorded in the computer system.

Figure 37:
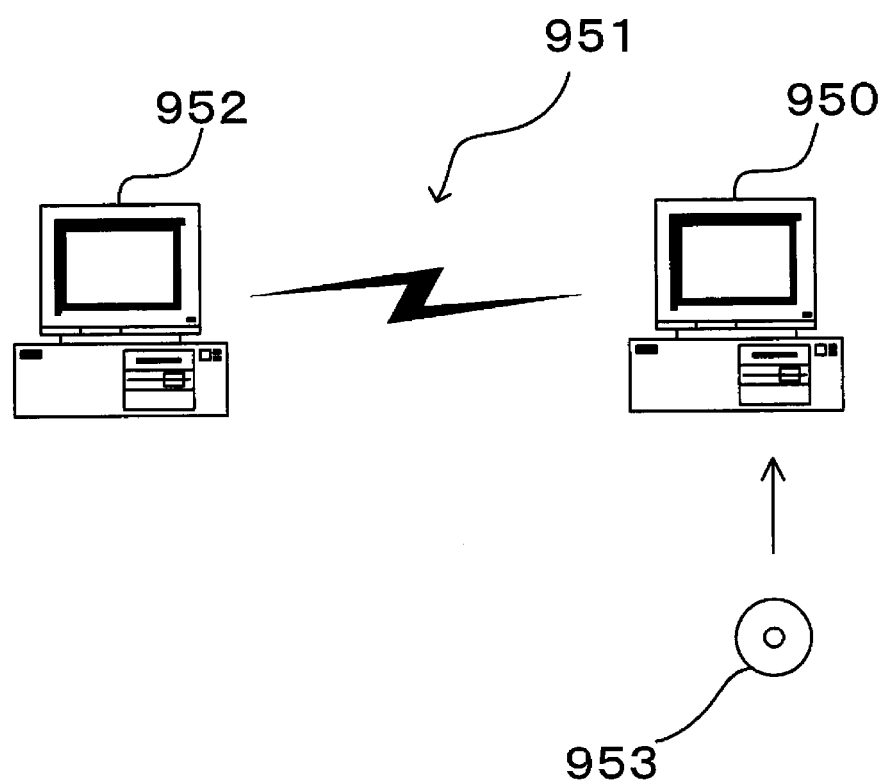
FIG. 37 is a figure illustrating the entire configuration of a mechanism used to provide a program product.

Furthermore, when being applied in a personal computer or the like, the program relating to the control described above can be provided through a recording medium such as a CD-ROM or a data signal such as the Internet. FIG. 37 is a diagram illustrating the above. A personal computer 950 receives the program provided via a CD-ROM 953. Moreover, the personal computer 950 has a connection function with a communication line 951. A computer 952 is a server computer that provides the above program and stores the program in a recording medium such as a hard disk. The communication line 951 is a communication line, such as the Internet or personal-computer communication; a dedicated communication line; or the like. The computer 952 reads the program using the hard disk and sends the program to the personal computer 950 via the communication line 951. That is, the program is conveyed by a carrier wave as a data signal and sent via the communication line 951. In this manner, the program can be provided as a computer-program product that can be read by a computer in various forms such as a recording medium or a carrier wave.

The present invention is not limited to the embodiments described above, and various modifications may be made without departing from the spirit of the present invention. Other embodiments that embody the technical concepts of the present invention are also included within the scope of the present invention.

What is claimed is:

1. A measurement processing device used for an x-ray inspection apparatus that detects an x-ray passing through a predetermined region of a specimen placed on a placement unit to perform an inspection on the shape of the predetermined region of the specimen, the measurement processing device comprising:
    a setting unit that sets a three-dimensional region to be detected on the specimen; and
    a slice selection unit that sets a plurality of sliced regions on the region to be detected, calculates, for each of the plurality of sliced regions, an amount of displacement of the predetermined region that is required to detect the region to be detect when the plurality of sliced regions are regarded as the predetermined region, and selects a sliced region for the inspection from among the plurality of sliced regions on the basis of each of the calculated amounts of displacement.

2. The measurement processing device according to claim 1, wherein:
    the setting unit sets a plurality of three-dimensional regions to be detected on the specimen; and
    the slice selection unit sets the plurality of sliced regions for each of the plurality of regions to be detected, calculates, for each of the plurality of sliced regions, the amount of displacement of the predetermined region that is required to detect the region to be detected when the plurality of sliced regions are regarded as the predetermined region, and selecting a sliced region for an inspection from among the plurality of sliced regions on the basis of each of the calculated amounts of displacement.

3. The measurement processing device according to claim 2, further comprising:
    a grouping unit that divides each of the selected sliced regions in the plurality of regions to be detected into a first group in which a first sliced region is selected and a second group in which a second sliced region is selected; and
    a control unit that performs x-ray detection on each region to be detected belonging to the first group, and afterwards performing x-ray detection on each region to be detected belonging to the second group.

4. The measurement processing device according to claim 3, wherein
    an orientation of the specimen placed on the placement unit differs between the x-ray detection in the region to be detected belonging to the first group and the x-ray detection in the region to be detected belonging to the second group.

5. The measurement processing device according to claim 4, further comprising
    a required time holding unit that keeps a required time necessary to switch from a state wherein the specimen is placed on the placement unit so as to detect an x-ray passing through the predetermined region belonging to the first group to a state wherein the specimen is placed on the placement unit so as to detect an x-ray passing through the predetermined region belonging to the second group; wherein
    the sliced region for the inspection is selected from among the plurality of set sliced regions by calculating for each of the plurality of sliced regions and by using each of the calculated amounts of displacement and the required time.

6. The measurement processing device according to claim 3, wherein
    respective regions to be detected are consolidated as one region to be detected in case that a plurality of regions to be detected exist in the predetermined region in at least a part of displacement position when the predetermined region is displaced to detect the regions to be detected from among the plurality of sliced regions set in the region to be detected.

7. The measurement processing device according to claim 3, wherein
    the grouping unit divides the plurality of regions to be detected belonging to the first group into a third group detected at a first magnification and a fourth group detected at a second magnification, as well as dividing the plurality of regions to be detected belonging to the second group into a fifth group detected at the first magnification and a sixth group detected at the second magnification; and the control unit performs x-ray detection at the first magnification for each of the regions to be detected belonging to the third group, as well as performing x-ray detection at the second magnification for each of the regions to be detected belonging to the fourth group, and performs x-ray detection at the first magnification for each of the regions to be detected belonging to the fifth group, as well as performing x-ray detection at the second magnification for each of the regions to be detected belonging to the sixth group.

8. The measurement processing device according to claim 2, further comprising a grouping unit that divides the plurality of regions to be detected into a first group to be detected at a first magnification, and a second group to be detected at a second magnification; and a control unit that performs x-ray detection at the first magnification for each of the regions to be detected belonging to the first group, and performs x-ray detection at the second magnification for each of the regions for detection belonging to the second group.

9. The measurement processing device according to claim 8, wherein the slice selection unit calculates the amount of displacement for each of the plurality of sliced regions set for each of the plurality of regions to be detected belonging to the first group, which the grouping unit divides into a third group in which a first sliced region is set and a fourth group in which a second sliced region is set;

the slice selection unit computes the amount of displacement for each of the plurality of sliced regions set for each of the plurality of regions to be detected belonging to the second group, which the grouping unit divides into a fifth group in which a first sliced region is set and a sixth group in which a second sliced region is set; and the control unit performs x-ray detection for each of the regions to be detected belonging to the third group and performs x-ray detection for each of the regions to be detected belonging to the fourth group, and afterwards performs x-ray detection for each of the regions to be detected belonging to the fifth group and performs x-ray detection for each of the regions to be detected belonging to the sixth group.

10. The measurement processing device according to claim 2, wherein the plurality of regions to be detected include a plurality of three-dimensional first regions to be detected and a second region to be detected wherein the region to be detected can be displaced within a predetermined range;

further comprising a resetting unit that displaces the second region to be detected in the predetermined range so as to include both the first and the second regions to be detected in at least one sliced region among the sliced regions set for the region to be detected, and for setting the second region to be detected.

11. The measurement processing device according to claim 10, wherein the resetting unit displaces the second region to be detected in the predetermined range to increase positions that are detectable in both the first and second regions to be detected in at least one sliced region among the sliced regions set for the region to be detected.

12. The measurement processing device according to claim 10, wherein the first region to be detected is fixed.

13. The measurement processing device according to claim 10, wherein the specimen is an engine block, and the second region to be detected is a crankshaft journal unit for the engine block.

14. The measurement processing device according to claim 2, wherein the plurality of regions to be detected includes a first plurality of three-dimensional regions to be detected and a second region to be detected wherein the region to be detected can be displaced within a predetermined range;

wherein the resetting unit moves the second region to be detected in the predetermined range so that first region to be detected and the second region to be detected overlap.

15. The measurement processing device according to claim 1, wherein the slice selection unit selects the sliced region with a small amount of movement for moving the sliced region to detect the region to be detected from among each of the calculated amounts of displacement.

16. The measurement processing device according to claim 1, wherein by moving the specimen on the placement unit in a direction orthogonal to a placement region on which the specimen is placed, the predetermined region on the specimen in which an x-ray can be detected is moved.

17. The measurement processing device according to claim 1, wherein the setting unit sets the region to be detected by using design information for the specimen.

18. The measurement processing device according to claim 1, wherein the setting unit sets the region to be detected by using simulation information in which information about the specimen is used.

19. The measurement processing device according to claim 1, wherein the setting unit sets the region to be detected by using the results of measurement information for the specimen.

20. The measurement processing device according to claim 1, wherein each of the plurality of sliced regions set for the region to be detected mutually intersect.

21. The measurement processing device according to claim 1, wherein the plurality of sliced regions include a sliced plane.

22. The measurement processing device according to claim 1, wherein the placement unit has a drive unit that moves in a predetermined direction; and a drive control unit that performs a first control for causing the drive unit to rotate the placement unit when the predetermined region exists in the region to be detected, and a second control for causing the drive unit to move the placement unit relatively when the predetermined region does not exist in the region to be detected.

23. The measurement processing device according to claim 1, further comprising a dividing unit that divides the region to be detected into a plurality of predetermined three-dimensional lattices; wherein the three-dimensional lattices are larger than a three-dimensional lattice prescribed by a resolution unit at the time of detection of the specimen.

24. The measurement processing device according to claim 1, comprising
a calculation unit that calculates a ratio at the time of inspection of the region to be detected on the specimen by using information for the region to be detected set by the setting part.

25. The measurement processing device according to claim 24, wherein
the calculation unit calculates a ratio at the time of inspection of the region to be detected on the specimen by using information for a placement plane of the placement unit relative to the specimen.

26. The measurement processing device according to claim 25, wherein
the calculation unit calculates the ratio at the time of inspection of the region to be detected on the specimen by using position information for the region to be detected on the specimen in a plane parallel to the placement plane.

27. A method for manufacturing structures, comprising:
creating design information regarding the shape of a structure;
creating the structure on the basis of the design information;
acquiring shape information by measuring the shape of the created structure by using the measurement processing device according to claim 1; and
comparing the acquired shape information and the design information.

28. The method for manufacturing structures according to claim 27, wherein
preforming refabrication of the structure by implementation on the basis of comparison results between the shape information and the design information.

29. The method for manufacturing structures according to claim 28, wherein
the refabrication of the structure comprises performing creation of the structure again on the basis of the design information.

30. An x-ray inspection apparatus that detects an x-ray passing through a predetermined region of a specimen to inspect the shape of the predetermined region of the specimen, the x-ray inspection apparatus comprising:
a setting unit that sets a plurality of three-dimensional regions to be detected on the specimen;
a grouping unit that divides the plurality of regions to be detected into a first group detected at a first magnification and a second group detected at a second magnification; and
a control unit that performs x-ray detection at the first magnification for each of the regions to be detected belonging to the first group, and thereafter performs x-ray detection at the second magnification for each of the regions to be detected belonging to the second group.

31. A measurement processing method, comprising:
setting a three-dimensional region to be detected on the specimen to perform an inspection on the shape of a predetermined region of the specimen by detecting an x-ray passing through the predetermined region of the specimen placed on a placement unit; and
setting a plurality of sliced regions for the region to be detected, calculating, for each of the plurality of sliced region, an amount of displacement of the predetermined region that is required to detect the region to be detect when the plurality of sliced regions are regarded as the predetermined region, and selecting a sliced region for the inspection from among the plurality of sliced regions on the basis of each of the calculated amounts of displacement.

32. An x-ray inspection method that detects an x-ray passing through a predetermined region of a specimen to inspect the shape of the predetermined region of the specimen, the x-ray inspection method comprising:
setting each of a plurality of three-dimensional regions to be detected on the specimen;
dividing the plurality of regions to be detected into a first group detected at a first magnification and a second group detected at a second magnification; and
performing x-ray detection at the first magnification for each of the regions to be detected belonging to the first group, and thereafter performing x-ray detection at the second magnification for each of the regions to be detected belonging to the second group.

33. A measurement processing program for causing a computer to execute, comprising:
setting processing for setting a three-dimensional region to be detected on a specimen to perform an inspection on the shape of a predetermined region of the specimen by detecting an x-ray passing through the predetermined region of the specimen placed on a placement unit; and
selection processing for setting a plurality of sliced regions for the region to be detected, calculating, for each of the plurality of sliced regions, an amount of displacement of the predetermined region that is required to detect the region to be detect when the plurality of sliced regions are regarded as the predetermined region, and selecting a sliced region for the inspection from among the plurality of sliced regions on the basis of each of the calculated amounts of displacement.

34. An x-ray inspection program for causing a computer to execute, comprising:
inspection processing for inspecting the shape of a predetermined region of a specimen by detecting an x-ray passing through the predetermined region of the specimen;
setting processing for setting each of a plurality of three-dimensional regions to be detected on the specimen;
division processing for dividing the plurality of regions to be detected into a first group detected at a first magnification and a second group detected at a second magnification; and
measurement processing for performing x-ray detection at the first magnification for each of the regions to be detected belonging to the first group, and thereafter performing x-ray detection at the second magnification for each of the regions to be detected belonging to the second group.

* * * * *